(12) United States Patent
Xu et al.

(10) Patent No.: US 9,949,927 B2
(45) Date of Patent: Apr. 24, 2018

(54) BIS-POLYMER LIPID-PEPTIDE CONJUGATES AND NANOPARTICLES THEREOF

(71) Applicant: The Regents of the University of California, Oakland, CA (US)

(72) Inventors: Ting Xu, Berkeley, CA (US); He Dong, Albany, CA (US); Jessica Shu, San Francisco, CA (US); Nikhil Dube, Berkeley, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/490,336

(22) Filed: Sep. 18, 2014

(65) Prior Publication Data

US 2017/0049901 A1 Feb. 23, 2017

Related U.S. Application Data

(63) Continuation-in-part of application No. PCT/US2013/035924, filed on Apr. 10, 2013.

(60) Provisional application No. 61/889,324, filed on Oct. 10, 2013, provisional application No. 61/880,068, filed on Sep. 19, 2013, provisional application No. 61/668,923, filed on Jul. 6, 2012, provisional application No. 61/622,330, filed on Apr. 10, 2012.

(51) Int. Cl.
| | |
|---|---|
| *A61K 38/00* | (2006.01) |
| *A61K 9/107* | (2006.01) |
| *A61K 31/704* | (2006.01) |
| *A61K 51/12* | (2006.01) |
| *A61K 31/436* | (2006.01) |
| *A61K 31/337* | (2006.01) |
| *A61K 47/62* | (2017.01) |
| *A61K 47/69* | (2017.01) |
| *A61K 47/42* | (2017.01) |

(52) U.S. Cl.
CPC .......... *A61K 9/1075* (2013.01); *A61K 31/337* (2013.01); *A61K 31/436* (2013.01); *A61K 31/704* (2013.01); *A61K 47/62* (2017.08); *A61K 47/6907* (2017.08); *A61K 51/1227* (2013.01); *A61K 47/42* (2013.01)

(58) Field of Classification Search
CPC ........... A61K 31/704; A61K 47/48176; A61K 47/48215; A61K 9/1075
See application file for complete search history.

(56) References Cited

U.S. PATENT DOCUMENTS 7,452,679 B2 11/2008 Stupp et al.
9,044,514 B2 * 6/2015 Xu ................. A61K 47/48038

2008/0299205 A1 12/2008 Mayer et al.
2010/0015173 A1 * 1/2010 Boato ................. A61K 39/015
  424/193.1
2010/0255311 A1 10/2010 Lee et al.
2011/0200527 A1 8/2011 Xu et al.
2013/0101628 A1 4/2013 Webber et al.
2016/0009770 A1 1/2016 Xu et al.

FOREIGN PATENT DOCUMENTS

| JP | 2011-520962 A | 7/2011 | |
|---|---|---|---|
| WO | WO-2003/022250 A2 | 3/2003 | |
| WO | WO-2003/022250 A3 | 3/2003 | |
| WO | WO-2008/068017 A1 | 6/2008 | |
| WO | WO-2009/142892 A1 | 11/2009 | |
| WO | WO-2011/066684 A1 | 6/2011 | |
| WO | WO2011/112999 * | 9/2011 | ............. C07K 14/47 |
| WO | WO-2011/112999 A2 | 9/2011 | |
| WO | WO-2011/112999 A3 | 9/2011 | |
| WO | WO-2013/100704 A1 | 7/2013 | |
| WO | WO-2013/155152 A1 | 10/2013 | |
| WO | WO-2015/042252 A1 | 3/2015 | |

OTHER PUBLICATIONS

Canalle et al. Polypeptide-polymer bioconjugates. Chem Soc Rev, 2010, vol. 39, pp. 329-353.*
Su et al. A synthetic method for peptide-PEG-lipid conjugates: Application of Octreotide-PEG-DSPE synthesis. Bioorganic and Medicinal Chemistry Letters. 2008. vol. 18, pp. 4593-4596.*
Zalipsky et al. Poly(ethylene glycol)-Grafted Liposomes with Oligopeptide or Oligosaccharide Ligands Appended to the Termini of the Polymer Chains. Bioconjugate Chem, 1997, vol. 8, pp. 111-118.*
Shu et al. Amphiphilic Peptide-Polymer Conjugates Based on the Coiled-Coil Helix Bundle. Biomacromolecules, 2010. vol. 11, pp. 1143-1452.*
Berendsen, H.J. (Oct. 23, 1998). "A glimpse of the Holy Grail?" *Science* 282(5359):642-643.
Betz, et al. (1995) "Design of Two-Stranded and Three-Stranded Coiled-Coil Peptides." *Philosophical Transactions: Biological Sciences*. 348 (1323): 81-88.
Branco, M.C. et al. (Mar. 2009, e-published Oct. 10, 2008). "Self-assembling materials for therapeutic delivery" *Acta Biomater* 5(3):817-831.
Bryson, et al. (Nov. 10, 1995) "Protein Design: A Hierarchic Approach." *Science*. 270: 935-941.
Burkhard, et al. (2000). "Design of a minimal protein oligomerization domain by a structural approach." *Prot. Sci.* 9, 2294-2301.
Cannon. "Pharmaceutics and drug delivery aspects of heme and porphyrin therapy," J. Pharma. Sci., vol. 82(5), pp. 435-446 (1993).
Chao, et al. (1996) "Kinetic Study on the Formation of a de Novo Designed Heterodimeric Coiled-Coil." *Biochemistry*. 35: 12175-12185.

(Continued)

*Primary Examiner* — Marcela M Cordero Garcia
(74) *Attorney, Agent, or Firm* — Mintz, Levin, Cohn, Ferris, Glovsky and Popeo, P.C.

(57) ABSTRACT

The present invention provides bis-polymer lipid-peptide conjugates containing a hydrophobic block and headgroup containing a helical peptide and two polymer blocks. The conjugates can self-assemble to form helix bundle subunits, which in turn assemble to provide micellar nanocarriers for drug cargos and other agents. Particles containing the conjugates and methods for forming the particles are also disclosed.

34 Claims, 33 Drawing Sheets

(56) References Cited

OTHER PUBLICATIONS

Chen, et al. "Determination of the secondary structures of proteins by circular dichroism and optical rotation dispersion," *Biochemistry*, vol. 11(22), pp. 4120-4131 (1972).
Chin, et al. (1992) "Self-assembling hexameric helical bundle forming peptides." *J. Am. Chem. Soc.* 114: 2279.
Cole et al. (2008) "Analytical Ultracentrifugation: Sedimentation Velocity and Sedimentation Equilibrium." Methods Cell Biol. 84: 143-179.
Creighton, T.E. (Apr. 9-15, 1987). "Protein structure. Stability of alpha-helices," *Nature* 326(6113):547-548.
Delorenzi, et al. (2002) "An HMM model for coiled-coil domains and a comparison with PSSM-based predictions." *Bioinformatics.* 18(4): 617-625.
Dong, H. et al. (Jun. 26, 2012, e-published May 4, 2012). "Long-circulating 15 nm micelles based on amphiphilic 3-helix peptide-PEG conjugates," *ACS Nano* 6(6):5320-5329.
Extended European Search Report dated Apr. 20, 2017 for EP Application No. 14845308.7, filed Sep. 18, 2014, 5 pages.
Extended European Search Report dated Jun. 16, 2014 for EP Application No. 13776184.7, filed Apr. 10, 2013, 7 pages.
Harbury, et al. (1993) "A Switch Between Two-, Three-, and Four-Stranded Coiled Coils in GCN4 Leucine Zipper Mutants." *Science* 262(5138): 1401-1407.
Harbury et al. (Sep. 1, 1994). "Crystal structure of an isoleucine-zipper trimer." *Nature* 371: 80-83.
Hennessey, et al. (1981) "Information Content in the Circular Dichroism of Proteins." *Biochemistry.* 20: 1085-1094.
Herringson, T.P. et al. (Jun. 15, 2011, e-published Apr. 4, 2011). "Effective tumor targeting and enhanced anti-tumor effect of liposomes engrafted with peptides specific for tumor lymphatics and vasculature," *Int J Pharm* 411(1-2):206-214.
Hiemenz, P.C. (1986). *Principles of colloid and surface chemistry*, Second Edition Revised and Expanded, Table 8.1, p. 432.
Ho, et al. (1987) "Design of a 4-helix bundle protein: synthesis of peptides which self-associate into a helical protein." *J. Am. Chem. Soc.* 109: 6751.
Immordino, M.L. et al. (2006). "Stealth liposomes: review of the basic science, rationale, and clinical applications, existing and potential," *Int J Nanomedicine* 1(3):297-315.
International Search Report and Written Opinion dated Oct. 18, 2011, issued in International Patent Application No. PCT/US11/28198, filed Mar. 11, 2011, 11 pages.
International Search Report dated Jul. 29, 2013, for PCT Application No. PCT/US2013/035924, filed Apr. 10, 2013, 4 pages.
International Search Report dated Dec. 19, 2014, for PCT Application No. PCT/US2014/056287, filed Sep. 18, 2014, 3 pages.
Kelly, et al. (2000) "The Use of Circular Dichroism in the Investigation of Protein Structure and Function." *Current Protein and Peptide Science.* 1: 349-384.
Kendrew, et al. (1958) "A three-dimensional model of the myoglobin molecule obtained by x-ray analysis." *Nature.* 181(4610): 662-6.
Kitakuni, et al. (1994) "Thermodynamic characterization of an artificially designed amphiphilic α-helical peptide containing periodic prolines." *Prot. Sci.* 3: 831-837.
Kohn et al. (1995) "The effects of interhelical electrostatic repulsions between glutamic acid residues in controlling the dimerization and stability of two-stranded a-helical coiled-coils." *J. Biol. Chem.* 270: 25495-25506.
Lau, DeGrado et al. (2010) "Oligomerization of fusogenic peptides promotes membrane fusion by enhancing membrane destabilization." *Biophysical Journal.* 99: 2299-2308.
Lombardi, et al. (2000) "Retrostructural analysis of metalloproteins: Application to the design of a minimal model for diiron proteins." *Proc Natl Acad Sci USA.* 97: 6298-6305.
Lovejoy, et al. (1993) "Crystal structure of a synthetic triple-stranded alpha-helical bundle." *Science.* 259 (5099): 1288-93.
Ludtke, S.J. et al. (Oct. 29, 1996). "Membrane pores induced by magainin," *Biochemistry* 35(43):13723-13728.

Lupas et al. (1991) "Predicting Coiled Coils from Protein Sequences." *Science.* 252:1162-1164.
Lupas, et al. (2005) "The structure of a-helical coiled coils." *Adv Protein Chem.* 70: 37-78.
Lutgring, et al. (1994) "General strategy for covalently stabilizing helical bundles: A novel five-helix bundle protein." *J. Am. Chem. Soc.* 116, 6451.
Matsuzaki. "Magainins as paradigm for the mode of action of pore forming polypeptides," Biochim. Biophys. Acta, vol. 1376, pp. 391-400 (1998).
Mittl, et al. (2000). "The retro-GCN4 leucine zipper sequence forms a stable three-dimensional structure." *Proc. Natl. Acad. Sci. USA.* 97: 2562-2566.
Moitra, J. et al. (Oct. 14, 1997). "Leucine is the most stabilizing aliphatic amino acid in the d position of a dimeric leucine zipper coiled coil," *Biochemistry* 36(41):12567-12573.
Nilsson, P.G. et al. (1983). "Water Self-Diffusion in Nonionic Surfactant Solutions. Hydration and Obstruction Effects," *J Phys Chem* 87:4756-4761.
O'Shea, et al. (1993) "Peptide 'Velcro': Design of a heterodimeric coiled coil." *Curr. Biol.* 3: 658-667.
Ogihara, N.L. et al. (Jan. 1997). "The crystal structure of the designed trimeric coiled coil coil-VaLd: implications for engineering crystals and supramolecular assemblies," *Protein Sci* 6(1):80-88.
Osapay, G. et al. (1992). *J Am Chem Soc* 114(18):6966-6973.
Pauling, et al. (1951) "The Structure of Proteins: Two Hydrogen-Bonded Helical Configurations of the Polypeptide Chain." *Proc. Natl. Acad. Sci. USA.* 37: 205-211.
Perkins, W.R. et al. (Apr. 25, 2000). "Novel therapeutic nanoparticles (lipocores): trapping poorly water soluble compounds," *Int J Pharm* 200(1):27-39.
Richter, A.W. et al. (1983). "Antibodies against polyethylene glycol produced in animals by immunization with monomethoxy polyethylene glycol modified proteins," *Int Arch Allergy Appl Immunol* 70(20):124-131.
Robertson D.E. et al. (Mar. 31, 1994) "Design and synthesis of multi-haem proteins." *Nature* 368: 425-432.
Shu, J.Y. et al. (Aug. 2008, e-published Jul. 16, 2008). "New design of helix bundle peptide-polymer conjugates," *Biomacromolecules* 9(8):2111-2117.
Sodek, et al. (1972) "Amino-Acid Sequence of Rabbit Skeletal Tropomyosin and Its Coiled-Coil Structure." *Proc. Nat. Acad. Sci. USA.* 96(12): 3800-3804.
Ugarenko et al. (Jan. 1, 2009). "Development of Pluronic Micelle-Encapsulated Doxorubicin and Formaldehyde-Releasing Prodrugs for Localized Anticancer Chemotherapy," *Oncology Research Featuring Preclinical and Clinical Cancer Therapeutics* 17(7):283-299.
Walshaw, et al. (2001) "SOCKET: A Program for Identifying and Analysing Coiled-coil Motifs Within Protein Structures." *J. Mol. Biol.* 307, 1427-1450.
Woolfson. (2005) "The Design of Coiled Coil Structures and Assemblies." *Adv Protein Chem.* 70: 79-112,
Woodle, M.C. (1995). "Sterically stabilized liposome therapeutics," *Advanced Drug Delivery Reviews* 16:249-265.
Written Opinion dated Jul. 29, 2013, for PCT Application No. PCT/US2013/035924, filed Apr. 10, 2013, 7 pages.
Written Opinion Report dated Dec. 19, 2014, for PCT Application No. PCT/US2014/056287, filed Sep. 18, 2014, 4 pages.
Yampolsky, L.Y. et al. (Aug. 2005, e-published Jun. 8, 2005). "The exchangeability of amino acids in proteins," *Genetics* 170(4):1459-1472.
Yano, A. et al. (Dec. 12, 2003). "RGD motif enhances immunogenicity and adjuvanicity of peptide antigens following intranasal immunization," *Vaccine* 22(2):237-243.
Zalipsky, S. et al. (1995). "Chemistry of polyethylene glycol conjugates with biologically active molecules," *Advanced Drug Delivery Reviews* 16:157-182.
Yakugaku Zasshi (2008). "Frontier Study of the Liposomes on DDS," *The Pharmaceutical Society of Japan* 128(2):185-186. (Partial English translation).

* cited by examiner

Fig. 27 cont'd.
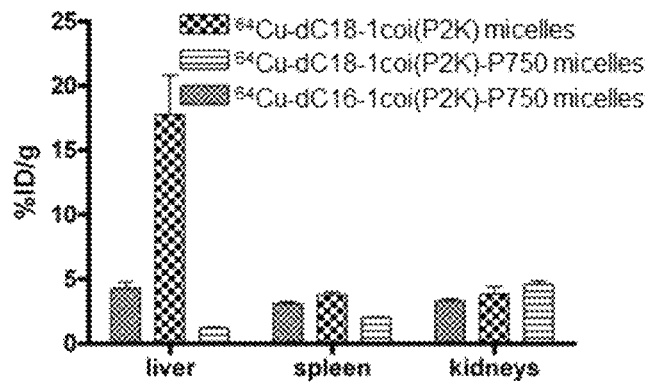
Fig. 27(C)
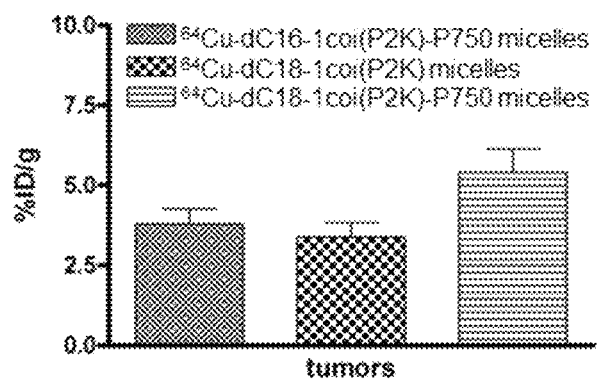
Fig. 27(D)
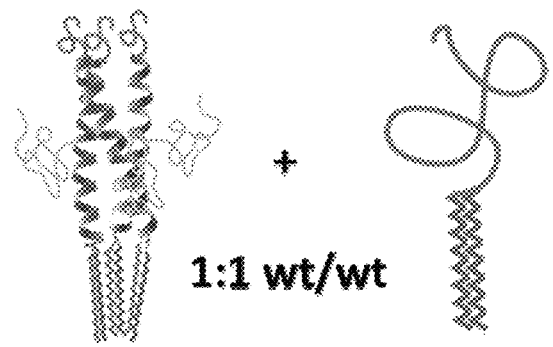
Fig. 28

BIS-POLYMER LIPID-PEPTIDE CONJUGATES AND NANOPARTICLES THEREOF

CROSS-REFERENCES TO RELATED APPLICATIONS

This application claims priority to U.S. Provisional Application Nos. 61/889,324, filed Oct. 10, 2013, and 61/880,068, filed Sep. 19, 2013, and is a continuation-in-part of PCT Application No. PCT/US2013/35924, filed Apr. 10, 2013, which claims priority to U.S. Provisional Application Nos. 61/668,923, filed Jul. 6, 2012, and 61/622,330, filed Apr. 10, 2012, each of which is incorporated in its entirety herein for all purposes.

STATEMENT AS TO RIGHTS TO INVENTIONS MADE UNDER FEDERALLY SPONSORED RESEARCH AND DEVELOPMENT

This invention was made with Government support under Grant No. W91NF-09-1-0374, awarded by the Office of the Army of the U. S. Department of Defense, Grant No. DE-AC02-05CH11231, awarded by the Office of Science, Office of Basic Energy Sciences, of the U.S. Department of Energy. The Government has certain rights in this invention.

REFERENCE TO A "SEQUENCE LISTING," A TABLE, OR A COMPUTER PROGRAM LISTING APPENDIX SUBMITTED AS AN ASCII TEXT FILE

The Sequence Listing written in file-103-1-1.TXT, created on Oct. 6, 2014, 4,096 bytes, machine format IBM-PC, MS-Windows operating system, is hereby incorporated by reference in its entirety for all purposes.

BACKGROUND OF THE INVENTION

It has been estimated that ~40% of emerging small molecule drugs have poor aqueous solubility and a short circulation half-life and require the development of effective drug formulations to improve their pharmacokinetics, biodistribution, toxicity profile and efficacy. When administrated intravenously, nanoscopic carriers offer the added advantage of concentrating in tumor tissues via the enhanced permeation and retention (EPR) effect defined by leaky vasculature and poor lymphatic drainage commonly seen in solid tumors. Studies have shown that following extravasation into tumor interstitium, a drug or drug-encapsulated vehicle should be capable of transport up to 100 μm away from the tumor vasculature in order to reach all cells within the tumor. There is increasing evidence that a drug's limited penetration and distribution within a tumor, which results in insufficient elimination of malignant cells, may contribute to tumor re-population after treatment. Current FDA approved DOXIL™ (~100 nm) and ABRAXANE™ (~130 nm), although highly promising, have provided only modest survival benefits. This is attributed to inefficient transport of the chemotherapeutic drug into the tumor due to their relatively larger size and drug leakage during blood circulation. Physiological factors, including the density and heterogeneity of the vasculature at the tumor site, interstitial fluid pressure, and transport of carriers in the tumor interstitium, impact the extent of extravasation of nanocarriers into tumors. Further, nanocarriers need to be below a certain size to achieve significant penetration where the range of nanocarrier diameter for efficient tumor penetration depends on the shape, hardness and architecture of the carrier. Recent studies using a human melanoma xenograft model in mice showed that smaller particles, i.e. 10-12 nm quantum dots, can more effectively penetrate the physiological barriers imposed by abnormal tumor vasculature and dense interstitial matrix than 60 nm nanoparticles. Using dendrimers, the physiologic upper limit of pore size in the blood-tumor barrier of malignant solid tumor microvasculature is approximately 12 nm. Organic nanoparticles based on elastin-like peptides, ~25 nm in size, produced a nearly complete tumor regression in a murine cancer model.

The effectiveness of a drug carrier also depends on its stability and drug retention in vivo. To ensure an improvement in the toxicity profile of the drug, the drug needs to be retained within micelles until reaching the target site. In addition to enhanced cargo stability and tumor penetration, an equally important requirement for effective nanocarriers is the balance of stable circulation and nanocarrier clearance. Nanocarriers initially must be larger than 6 nm to achieve extended circulation lifetime and subsequently need to disintegrate into materials smaller than ~6 nm or 50K Da in molecular weight to be eliminated from circulation by glomerular filtration in the kidney. The generation of organic nanocarriers in the size range of 10-30 nm which combine a long circulation half-life, effective tumor tissue penetration, minimal cargo leakage, and efficient subunit clearance remains a significant challenge.

Thermodynamically, the particle size is determined by the balance between interfacial interactions between the particle surface and the local medium and the cohesive energy stored in the particle. The surface area to volume ratio is inversely proportional to the particle size. As the particle size reduces down to the nanoscale, low surface tension of the particle surface and/or high cohesive energy density within nanoparticles are needed to stabilize individual nanoparticles. Depending on the amount of chemical energy involved in the formation and stabilization of nanoparticles, current organic nanoparticles can be divided into two categories. In one family of nanoparticles, including dendrimers, subunits are bound together via covalent bonds, with a typical energy of a few tens of kcal per mole. The second family of organic nanoparticles is stabilized via non-covalent bonds, typically a few kcal per mol. These nanoparticles often have very low interfacial interactions since the energy stored in the particle is relatively low.

The kinetic stability of organic nanoparticles determines the in vivo stability, circulation half-life and clearance pathway. Covalent nanoparticles are often stable under common biological conditions until chemical degradation of covalent bonds occurs via external stimuli such as pH, temperature, light and enzymes. For non-covalent nanoparticles, however, the subunit can exchange with local medium or among particles. The kinetic energy barrier of the exchange decreases as the micelle size reduces, especially when the size is below 20 nm. Small micelles are generally fluid, dynamic assemblies, where the subunit amphiphiles are constantly exchanging with the surrounding media and with other micelles. The presence of chemical traps in vivo that stabilize individual amphiphiles further reduces the stability of micelles and leads to undesirable cargo leakage and disassembly. Chemically crosslinking the headgroups and/or engineering multiple pairs of intermolecular interactions among the headgroups can be effective to obtain stable micelles. However, biodistribution studies indicated accumulation in the liver and spleen and raised concerns over the potential long term toxicity.

Accordingly, an unmet need exists for small (i.e. on the order of a few tens of nanometers), stable micelles that can be assembled from convenient materials and used for in vivo delivery of drugs and other cargo. Surprisingly, the present invention addresses this and other needs.

BRIEF SUMMARY OF THE INVENTION

In some embodiments, the present invention provides a conjugate including a peptide having from about 10 to about 100 amino acids, wherein the peptide adopts a helical structure. The conjugate also includes a first polymer covalently linked to an amino acid residue of the peptide other than the N-terminal and C-terminal amino acid residues, at least one second polymer covalently linked to the C-terminal amino acid residue of the peptide, and a hydrophobic moiety covalently linked to the N-terminus of the peptide wherein the hydrophobic moiety comprises a third polymer or a lipid moiety.

In some embodiments, the present invention provides a helix bundle having from 2 to 6 conjugates of the present invention.

In some embodiments, the present invention provides a particle having from about 20 to about 200 conjugates of the present invention.

In some embodiments, the present invention provides a particle having from about 20 to about 200 conjugates of the present invention. Each conjugate includes a first peptide having SEQ ID NO:1, a first polymer including polyethylene glycol with a molecular weight of about 2000 Da, a second polymer covalently linked to the C-terminal residue of the peptide and including polyethylene glycol with a molecular weight of about 750 Da, and a hydrophobic moiety having a lipid moiety which includes lysine and two $C_{18}$ acyl chains. The particle also includes a therapeutic agent selected from doxorubicin, paclitaxel, and rapamycin.

In some embodiments, the present invention provides a method of forming a particle of the present invention. The method includes contacting a plurality of conjugates of the present invention such that the conjugates self-assemble to form the particles.

In some embodiments, the present invention further provides a method for delivering a diagnostic or therapeutic agent to a subject comprising administering a particle to the subject. Thus, the particle includes from about 20 to about 200 conjugates of the present invention and the therapeutic agent.

In some embodiments, the present invention provides a method for treating a subject with a disease. The method includes administering a therapeutically effective amount of a particle to the subject, wherein the particle includes from about 20 to about 200 conjugates of the present invention and a therapeutic agent. Thus, the disease is treated.

In some embodiments, the present invention provides a method for treating cancer. The method includes administering to a human subject, a therapeutically effective amount of a particle of the present invention. The particle includes from about 20 to about 200 conjugates of the present invention and at least one therapeutic agent.

In some embodiments, the present invention further provides a method of treating a disease state in a human subject. The method includes administering to a human subject, a therapeutically effective amount of a particle of the present invention. The particle includes from about 20 to about 200 conjugates of the present invention and at least one therapeutic agent.

BRIEF DESCRIPTION OF THE DRAWINGS

FIG. 27 shows pharmacokinetics measurements and biodistribution data for $^{64}$Cu-dC18-1coi(PEG2K) micelles, $^{64}$Cu-dC18-1coi(PEG2K)-PEG750 micelles, and $^{64}$Cu-dC16-1coi(PEG2K)-PEG750 micelles; FIG. 27C shows concentration of the micelles in the liver, spleen and kidneys; and FIG. 27D shows concentration of the micelles in tumors with $^{64}$Cu-dC18-1coi(PEG2K)-PEG750 micelles showing a higher concentration.

FIG. 28 shows a schematic representation of a mixed micelle system.

DETAILED DESCRIPTION OF THE INVENTION

I. General

Figures 1A, 1B, 1C:
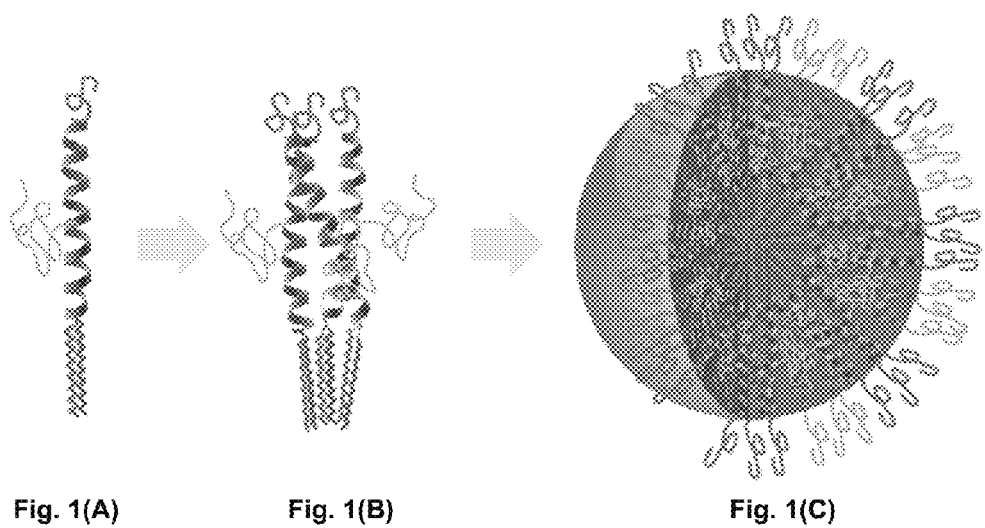
FIG. 1 shows the schematic assembly of (a) the bis-polymer lipid-peptide conjugate to form (b) 3-helix bundle subunits and (c) micelles with a shell composed of 3-helix bundles and a core composed of aliphatic chains.

The present invention provides micelle nanocarriers for in vivo delivery of drugs and other cargo. The nanoparticles can be targeted or untargeted. Suitable cargo that can be delivered by the nanocarriers of the present invention include, but are not limited to, vaccines, nucleic acids such as DNA or RNA, peptides, proteins, imaging agents, and drugs. The nanoparticles of the present invention are also useful for gene therapy, the administration of an expressed or expressible nucleic acid to a subject.

The nanocarriers are composed of bis-polymer lipid-peptide conjugates that self-assemble to form the micelles. The conjugates include a hydrophobic block and headgroup containing a helical peptide and two polymer blocks. Helix bundle formation by the peptides results in alignment of the hydrophobic block at the N-terminal end of the peptide bundle, with one polymer block covalently linked to the peptide along the length of the peptide, and the other polymer block covalently linked to the C-terminal end of the peptide. The micelles resulting from conjugate assembly contain a polymer shell on the micelle surface. The surface C-terminal polymer, in particular, contributes to the surprising stability and long circulation time of the micelle nanoparticles, as compared to micelles assembled from conjugates without a C-terminal polymer and other previously known self-assembled nanocarrier structures.

II. Definitions

"Conjugate" refers to a compound having a first polymer, a second polymer, a peptide and a hydrophobic moiety all linked together. The conjugates are capable of self-assembling to form helix bundles. The helix bundles include from 2 to 6 conjugates, typically 3 or 4.

"Polypeptide," "peptide," and "protein" are used interchangeably herein to refer to a polymer of amino acid residues. All three terms apply to amino acid polymers in which one or more amino acid residues is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds. The peptides of the present invention can be helical in structure and form a coiled-coil tertiary protein structure. The formation of coiled-coil tertiary structure provides a structural scaffold to position conjugated polymers and define the shape of individual sub-units for the nanoparticle. The helices also enhance the rigidity of the sub-unit and enable the geometric packing in a manner similar to that of virus particles.

"N-terminus" refers to the first amino acid residue in a protein or polypeptide sequence. The N-terminal residue contains a free α-amino group.

"C-terminus" refers to the last amino acid residue in a protein or polypeptide sequence. The C-terminal residue contains a free carboxylate group.

"Polymer" refers to a macromolecule having repeating units connected by covalent bonds. Polymers can be hydrophilic, hydrophobic or amphiphilic. Hydrophilic polymers are substantially miscible with water and include, but are not limited to, polyethylene glycol. Hydrophobic polymers are substantially immiscible with water and include, but are not limited to, polybutadiene and polystyrene. Amphiphilic polymers have both hydrophilic and hydrophobic properties and are typically block copolymers of a hydrophilic and a hydrophobic polymer. Polymers include homopolymers, random copolymers, and block copolymers. Specific polymers useful in the present invention include polyethylene glycol, N-isopropylacrylamide (NIPAM), polybutadiene and polystyrene, among others.

"Hydrophobic moiety" refers to polymers or small molecules that are hydrophobic. Examples of hydrophobic moieties include, but are not limited to, hydrophobic polymers such as polybutadiene and polystyrene, as well as the lipid moieties of the present invention.

"Lipid moiety" refers to a moiety having at least one lipid. Lipids are small molecules having hydrophobic or amphiphilic properties and are useful for preparation of vesicles, micelles and liposomes. Lipids include, but are not limited to, fats, waxes, fatty acids, cholesterol, phospholipids, monoglycerides, diglycerides and triglycerides. The fatty acids can be saturated, mono-unsaturated or poly-unsaturated. Examples of fatty acids include, but are not limited to, butyric acid (C4), caproic acid (C6), caprylic acid (C8), capric acid (C10), lauric acid (C12), myristic acid (C14), palmitic acid (C16), palmitoleic acid (C16), stearic acid (C18), isostearic acid (C18), oleic acid (C18), vaccenic acid (C18), linoleic acid (C18), alpha-linoleic acid (C18), gamma-linolenic acid (C18), arachidic acid (C20), gadoleic acid (C20), arachidonic acid (C20), eicosapentaenoic acid (C20), behenic acid (C22), erucic acid (C22), docosahexaenoic acid (C22), lignoceric acid (C24) and hexacosanoic acid (C26). The lipid moiety can include several fatty acid groups using branching groups such as lysine and other branched amines.

"Alkyl" refers to a straight or branched, saturated, aliphatic radical having the number of carbon atoms indicated. Alkyl groups can have up to 24 carbons atoms and include heptyl, octyl, nonyl, decyl, dodecyl, tridecyl, tetradecyl, pentadecyl, hexadecyl, heptadecyl, octadecyl, nonadecyl, icosyl, and the like. Alkyl can include any number of carbons such as $C_{6-20}$, $C_{6-18}$, $C_{6-16}$, $C_{8-24}$, $C_{8-22}$, and $C_{8-20}$. Alkyl groups can be substituted with substituents including fluorine groups.

"Acyl" refers to a carbonyl radical (i.e., C=O) substituted with an alkyl group as defined above. The number of carbon atoms indicated for an acyl group includes the carbonyl carbon and the alkyl carbons. Acyl groups can have up to 24 carbons atoms and include heptoyl, octoyl, nonoyl, decoyl, dodecoyl, tridecoyl, tetradecoyl, pentadecoyl, hexadecoyl, heptadecoyl, octadecoyl, nonadecoyl, icosoyl, and the like. Acyl can include any number of carbons such as $C_{6-20}$, $C_{6-18}$, $C_{6-16}$, $C_{8-24}$, $C_{8-22}$, and $C_{8-20}$. Acyl groups can be substituted with substituents including fluorine groups.

"Anthracycline" refers to natural products of *Streptomyces peucetius* and related derivatives. Anthracyclines are glycosides containing an amino sugar and a fused, tetracyclic aglycone. Many anthracyclines demonstrate antibiotic and antineoplastic activity. Examples of anthracyclines include, but are not limited to, daunorubicin, doxorubicin, epirubicin, and idarubicin.

"Macrolide" refers to compounds characterized by a large (typically 14-to-16-membered) lactone ring substituted with pendant deoxy sugars. Many macrolides demonstrate antibiotic and immunomodulatory activity. Examples of macrolides include, but are not limited to, rapamycin, clarithromycin, and erythromycin.

"Therapeutic agent" refers to an agent capable of treating and/or ameliorating a condition or disease. Therapeutic agents include, but are not limited to, compounds, drugs, peptides, oligonucleotides, DNA, antibodies, and others.

"Diagnostic agent" refers to an agent capable of diagnosing a condition or disease. Diagnostic agents include, but are not limited to, dyes and radiolabels.

"Nucleic acid," "oligonucleotide," and "polynucleotide" refer to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. The term nucleic acid is used interchangeably with gene, cDNA, and mRNA encoded by a gene.

"Contacting" refers to the process of bringing into contact at least two distinct species such that they can interact. In some cases, such interactions include non-covalent interactions such as ionic interactions and van der Waals interactions. In some cases, the interaction results in a covalent bond-forming reaction. In these cases, it should be appreciated that the resulting reaction product can be produced directly from a reaction between the added reagents or from an intermediate from one or more of the added reagents which can be produced in the reaction mixture.

"Amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine.

"Amino acid analogs" refer to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid.

"Unnatural amino acids" are not encoded by the genetic code and can, but do not necessarily have the same basic structure as a naturally occurring amino acid. Unnatural amino acids include, but are not limited to azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethyl asparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, ornithine, pentylglycine, pipecolic acid and thioproline.

"Amino acid mimetics" refers to chemical compounds that have a structure that is different from the general chemical structure of an amino acid, but that functions in a manner similar to a naturally occurring amino acid.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" apply to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid (i.e., hydrophobic, hydrophilic, positively charged, neutral, negatively charged). Exemplified hydrophobic amino acids include valine, leucine, isoleucine, methionine, phenylalanine, and tryptophan. Exemplified aromatic amino acids include phenylalanine, tyrosine and tryptophan. Exemplified aliphatic amino acids include serine and threonine. Exemplified basic amino acids include lysine, arginine and histidine. Exemplified amino acids with carboxylate side-chains include aspartate and glutamate. Exemplified amino acids with carboxamide side chains include asparagines and glutamine. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

"Helix bundle" refers to a structure formed by the self-assembly of a plurality of conjugates of the present invention, where the hydrophobic moieties are aligned with each other at one end of the peptide bundle (typically the N-terminal end) and the polymers of each conjugate are arranged along the length of the peptide bundle and at the end of the peptide bundle opposite the hydrophobic moieties (typically the C-terminal end).

"Administering" refers to oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject.

"Treat", "treating," and "treatment" refer to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to a patient or subject; decreasing the frequency or duration of the symptom or condition; or, in some situations, preventing the onset of the symptom or condition. The treatment or amelioration of symptoms can be based on any objective or subjective parameter; including, e.g., the result of a physical examination.

"Cancer" includes solid tumors and hematological malignancies. Cancer includes but is not limited to cancers such as carcinomas, gliomas, mesotheliomas, melanomas, lymphomas, leukemias, adenocarcinomas, breast cancer, ovarian cancer, cervical cancer, glioblastoma, leukemia, lymphoma, prostate cancer, and Burkitt's lymphoma, brain and central nervous system, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, cervical cancer, vaginal cancer, uterine cancer, ovarian cancer, thyroid cancer, parathyroid cancer, adrenal cancer, pancreatic endocrine cancer, carcinoid cancer, bone cancer, skin cancer, retinoblastomas, Hodgkin's lymphoma, non-Hodgkin's lymphoma (see, CANCER:PRINCIPLES AND PRACTICE (DeVita, V. T. et al. eds 1997) for additional cancers). One of skill in the art will appreciate that other cancers and proliferative disorders can be treated by the particles of the present invention.

"Therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). In sensitized cells, the therapeutically effective dose can often be lower than the conventional therapeutically effective dose for non-sensitized cells.

III. Conjugates, Helix Bundles, and Particles

In some embodiments, the present invention provides a conjugate having a first peptide with from about 10 to about 100 amino acids, wherein the peptide adopts a helical structure. The conjugate also includes: a first polymer covalently linked to an amino acid residue of the peptide, other than the N-terminal and C-terminal residues; at least one second polymer covalently linked to the C-terminal amino acid residue of the peptide; and a hydrophobic moiety covalently linked to the N-terminus of the peptide, wherein the hydrophobic moiety comprises a third polymer or a lipid moiety.

Peptides useful in the conjugates of the present invention are those that adopt a helical conformation. The peptides can be of any suitable length, such as from about 10 to about 1000 amino acids, or from about 10 to about 500 amino acids, or from about 10 to about 100 amino acids. In some embodiments, the peptide can be SEQ ID NO: 1, SEQ ID NO: 2, SEQ ID NO: 4, SEQ ID NO: 5, and SEQ ID NO: 6.

In a preferred embodiment, the first peptide can self-associate to form tertiary peptide structures. In some embodiments, the first peptide can be a de novo designed 3-helix bundle peptide, such as, but not limited to, SEQ ID NO: 1. In some embodiments, 1-50 amino acids can be appended to the C-terminus of the first peptide without interfering with micelle formation. In some embodiments, 1-25 amino acids, preferably 1-10 amino acids and more preferably 1-5 amino acids, can be appended to the C-terminus of the first peptide. In some embodiments, the first peptide sequence can be a control peptide sequence that a forms random coil such as, but not limited to, SEQ ID NO: 4. In some embodiments, the first peptide can be designed based on SEQ ID NO:5, and have similar characteristics including PI and hydrophobicity. In some embodiments, the first peptide sequence can be a heme-binding peptide that is able to form 4-helix bundles such as SEQ ID NO: 2.

The conjugates of the present invention also include a first polymer and a second polymer. The first and second polymers can be any suitable polymer. Exemplary polymers include hydrophilic, hydrophobic and amphiphilic polymers. As a non-limiting example, the first polymer and the second polymer can be independently selected from polyethylene glycol (PEG or P), poly(N-isopropylacrylamide) (NIPAM), polybutadiene (PBD), and polystyrene (PS). In some embodiments, the first polymer and the second polymer include hydrophilic polymers. Hydrophilic polymers are miscible with water, and include, but are not limited to, polyethylene glycol, NIPAM, and cellulose. In some embodiments, the first polymer and the second polymer include polyethylene glycol.

The first polymer can be linked to any point of the peptide other than the N-terminal amino acid residue and the C-terminal amino acid residue. Any suitable covalent linkage is useful for attaching the first polymer to the peptide. For example, the covalent linkage can be via an ester, amide, ether, thioether or carbon linkage. In some embodiments, the first polymer can be modified with a maleimide that reacts with a sulfhydryl group of the peptide, such as on a cysteine. In some embodiments, the first polymer can be linked to the peptide via click chemistry, by reaction of an azide and an alkyne to form a triazole ring.

In general, the second polymer is linked to the C-terminal amino acid residue of the polymer. For example, a second polymer bearing an amine group can be covalently linked directly to the C-terminal carboxylate via an amide bond. The second polymer can also be linked to the sidechain of the C-terminal amino acid residue. A second polymer bearing a maleimide, for example, can be linked to the thiol group of a C-terminal cysteine sidechain. Alternatively, a second polymer bearing a carboxylate (or an activated carboxylate derivative) can be linked to the $\epsilon$-amino group of a C-terminal lysine sidechain. A number of other linkage strategies are known to those of skill in the art and can be used to synthesize the conjugates of the present invention. Such strategies are described in "Bioconjugate Techniques", 2nd edition, G. T. Hermanson, Academic Press, Amsterdam, 2008.

Attachment of the second polymer to the C-terminus of the peptide can modulate the interaction of the external environment with the micelles resulting from conjugate assembly. In some cases, the second polymer can minimize unwanted interactions between the micelle and non-target cells or tissues in a subject to whom the micelles are administered. Additionally, the second polymer can be used to promote desirable interactions with in vitro or in vivo targets. The multimeric helix bundles of the conjugates can be used as a platform for presentation of ligands on micelle surfaces for active targeting of the nanocarrier to desired locations. The second polymer on the micelle surface can be used to tailor the inter-ligand cluster distance and tune multi-valent ligand binding at target cells or tissues. Furthermore, the second polymer can also serve to modulate micelle stability. Without wishing to be bound by any particular theory, it is believed that the intermolecular interactions between the peptide helix bundles and the compression of the C-terminal second polymer on the exterior can increase the activation energy barrier for subunit desorption and provide stability to the micelle.

Conjugate assembly properties, as well as the stability of conjugate bundles and micelles, depend in part on conjugate architecture and the molecular weight of the polymers in the conjugate. The shape of a conjugate will influence the size and shape of the micelle resulting from conjugate assembly. The molecular weight of the first polymer and the second polymer can be chosen so as to tune the assembly and stability of the micelles. In general, polymer molecular weights are sufficiently large to stabilize the assembled micelles but not so large as to interfere with helix bundle assembly and micelle assembly. In some embodiments, the molecular weight of the first polymer can be from about 500 Da to about 10,000 Da. In some embodiments, the molecular weight of the first polymer can be, for example, from about 1000 Da to about 7500 Da, or from about 2000 Da to about 5000 Da. The molecular weight of the first polymer can be about 500 Da, or about 1000 Da, or about 2000 Da, or about 3000 Da, or about 4000 Da, or about 5000 Da, or about 6000 Da, or about 7000 Da, or about 8000 Da, or about 9000 Da, or about 10,000 Da. In some embodiments, the molecular weight of the first polymer can be from about 1000 Da to about 5000 Da. In some embodiments, the molecular weight of the first polymer can be about 2000 Da.

In some embodiments, the molecular weight of the second polymer can be from about 250 Da to about 5000 Da. In some embodiments, the molecular weight of the second polymer can be, for example, from about 300 Da to about 2500 Da, or from about 750 Da to about 2000 Da. In some embodiments, the molecular weight of the second polymer can be about 250 Da, or about 300 Da, or about 350 Da, or about 400 Da, or about 500 Da, or about 1000 Da, or about 1250 Da, or about 1500 Da, or about 1750 Da, or about 2000 Da, or about 3000 Da, or about 4000 Da, or about 5000 Da. In some embodiments, the molecular weight of the second polymer is from about 500 Da to about 2000 Da. In some embodiments, the molecular weight of the second polymer is about 750 Da.

In some embodiments, the hydrophobic moiety can be a third polymer. Polymers useful as the hydrophobic moiety include hydrophobic polymers such as polybutadiene, polystyrene, polyacrylates, polymethacrylates, polydiacetylene, and the like. In some embodiments, the hydrophobic moiety can be polybutadiene. In some embodiments, the third polymer can be from about 1000 Da to about 3000 Da. In some embodiments, the third polymer can be from about 1100 Da to about 2600 Da. In some embodiments, the third polymer can be from about 1000 Da to about 2000 Da.

In some embodiments, the hydrophobic moiety can be a lipid moiety. Lipid moieties useful in the present invention include from 1 to 20 long acyl chains, from 1 to 10 acyl chains, or from 1 to 6 acyl chains, or 1, 2, 3, 4, 5, 6, 7, 8, 9 or 10 acyl chains. The lipid moieties can be prepared from fatty acids, which include, but are not limited to, capric acid (C10), lauric acid (C12), myristic acid (C14), palmitic acid (C16), palmitoleic acid (C16), stearic acid (C18), isostearic acid (C18), oleic acid (C18), vaccenic acid (C18), linoleic acid (C18), alpha-linoleic acid (C18), gamma-linolenic acid (C18), arachidic acid (C20), gadoleic acid (C20), arachidonic acid (C20), eicosapentaenoic acid (C20), behenic acid (C22), erucic acid (C22), docosahexaenoic acid (C22), lignoceric acid (C24) and hexacosanoic acid (C26).

Exemplary acyl groups in the lipid moieties include $C_{10-20}$ acyl chains, such as $C_{10}$, $C_{12}$, $C_{14}$, $C_{16}$, $C_{18}$, or $C_{20}$ acyl groups. In some embodiments, the lipid moieties have at least one $C_{14}$ acyl group, or at least one $C_{16}$ acyl group. When the lipid moieties include more than one acyl group, the lipid moiety also includes a branched linker providing for attachment of multiple acyl groups. The branched linkers useful in the present invention include, but are not limited to, lysine, glutamic acid and other branched amines and carboxylic acids. In some embodiments, the lipid moiety includes from 1 to 6 $C_{10-20}$ acyl groups. The lipid moiety can include 1, 2, 3, 4, 5 or 6 $C_{10-20}$ acyl groups. In some embodiments, the lipid moiety includes 1, 2, or 4 $C_{10-20}$ acyl groups. In some embodiments, the lipid moiety includes 1 $C_{10-20}$ acyl group. In some embodiments, the lipid moiety includes 2 $C_{10-20}$ acyl groups.

When the second polymer is linked to the sidechain of the C-terminal amino acid residue of the first peptide, the C-terminal carboxylate is available for linkage to additional moieties. The moieties at the C-terminus of the first peptide can be any useful binding or labeling moiety which can include, but is not limited to, an amino acid residue, an oligonucleotide, a polypeptide, an antibody, a diagnostic agent, a therapeutic agent, and a polymer. In some embodiments, the present invention provides conjugates as described above that include a second peptide covalently linked to the C-terminus of the first peptide. The second peptide can have any suitable number of amino acids, such as from 2 to about 100, or from 2 to about 50, or from 2 to about 20 amino acids. In some embodiments, the amino acid residue can be GGG, HHH, KK, EE, RGD and AYSS-GAPPMPPF (SEQ ID NO:3), and combinations thereof. Other second peptides are useful in the conjugates of the present invention. Alternatively, an additional moiety can be covalently linked to a conjugate at the chain end of the second polymer In some embodiments, the invention provides a conjugate as described above, wherein the peptide is SEQ ID NO:1, the first polymer is polyethylene glycol with a molecular weight of about 2000 Da, the second polymer is polyethylene glycol with a molecular weight of about 750 Da and is linked to the C-terminal residue of the peptide, and the hydrophobic moiety is a lipid moiety which includes lysine and two $C_{18}$ acyl chains.

The present invention also provides helix bundles, formed from the self-assembly of a plurality of conjugates. The helix bundles can be formed from 2, 3, 4, 5, 6, 7, 8, 9 or 10 conjugates. In some embodiments, the present invention provides a helix bundle having from 2 to 6 conjugates of the present invention. In some embodiments, the helix bundles includes 3 conjugates. In some embodiments, the helix bundle includes 4 conjugates.

The present invention also provides particles formed from the self-assembly of the helix bundles, such that the hydrophobic moiety forms a micellar structure having a hydrophobic core, and helix bundle headgroups are on the exterior of the core. The particles can include any suitable number of conjugates. In some embodiments, the present invention provides a particle having from about 20 to about 200 conjugates of the present invention. The particles can be of any suitable size. For example, the particles can be from about 5 nm to about 500 nm in diameter, or from about 5 to about 100 nm in diameter, or from about 5 nm to about 50 nm in diameter, or from about 5 nm to about 25 nm in diameter.

The particles of the present invention can include cargo in the hydrophobic interior of the particle. In some embodiments, the particles include at least one additional agent selected from a therapeutic agent, a diagnostic agent, DNA, an oligonucleotide, or other useful agents. Examples of therapeutic agents include, but are not limited to, anthracyclines (such as doxorubicin, daunorubicin, epirubicin, and the like), macrolides (such as rapamycin, fujimycin, pimecrolimus, and the like), alkylating agents (such as temozolomide, procarbazine, altretamine, and the like), taxanes, and *vinca* alkaloids. Examples of diagnostic agents include, but are not limited to, chromophores, fluorophores, and radionuclides. The conjugates, helix bundles and particles of the present invention can be linked to other particles, such as gold nanoparticles and magnetic nanoparticles that are typically a few nanometers in diameter for imaging and manipulation purposes. In some embodiments, the invention provides particles as described above, wherein each additional agent is independently selected from a fluorophore, a radionuclide, an anthracycline, a taxane, and a macrolide. In some embodiments, each additional agent is independently selected from doxorubicin, paclitaxel, and rapamycin. In some embodiments, the additional agent can be doxorubicin. Alternatively, the additional agents be covalently or noncovalently bound to one of, a combination of, or all of the peptide component, the first polymeric component, and the second polymeric component of the amphiphilic conjugates.

In some embodiments, the present invention provides a particle having from about 20 to about 200 conjugates of the present invention. Each conjugate includes a first peptide having SEQ ID NO:1, a first polymer including polyethylene glycol with a molecular weight of about 2000 Da, a second polymer covalently linked to the C-terminal residue of the peptide and including polyethylene glycol with a molecular weight of about 750 Da, and a hydrophobic moiety having a lipid moiety which includes lysine and two $C_{18}$ acyl chains. The particle also includes a therapeutic agent selected from doxorubicin, paclitaxel, and rapamycin. In some embodiments, the therapeutic agent can be doxorubicin.

Additional materials can be incorporated into the particles to form mixed micelles. For example, mixed micelles can include suitable lipid compounds. Suitable lipids can include but are not limited to fats, waxes, sterols, cholesterol, fat-soluble vitamins, monoglycerides, diglycerides, phospholipids, sphingolipids, glycolipids, derivatized lipids, and the like. In some embodiments, suitable lipids can include amphipathic, neutral, non-cationic, anionic, cationic, or hydrophobic lipids. In certain embodiments, lipids can include those typically present in cellular membranes, such as phospholipids and/or sphingolipids. Suitable phospholipids include but are not limited to phosphatidylcholine (PC), phosphatidic acid (PA), phosphatidylethanolamine (PE), phosphatidylglycerol (PG), phosphatidylserine (PS), and phosphatidylinositol (PI). Non-cationic lipids include but are not limited to dimyristoyl phosphatidyl choline (DMPC), distearoyl phosphatidyl choline (DSPC), dioleoyl phosphatidyl choline (DOPC), dipalmitoyl phosphatidyl choline (DPPC), dimyristoyl phosphatidyl glycerol (DMPG), distearoyl phosphatidyl glycerol (DSPG), dioleoyl phosphatidyl glycerol (DOPG), dipalmitoyl phosphatidyl glycerol (DPPG), dimyristoyl phosphatidyl serine (DMPS), distearoyl phosphatidyl serine (DSPS), dioleoyl phosphatidyl serine (DOPS), dipalmitoyl phosphatidyl serine (DPPS), dioleoyl phosphatidyl ethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearoyl-2-oleoyl-phosphatidyethanolamine (SOPE), 1,2-dielaidoyl-sn-glycero-3-phophoethanolamine (transDOPE), and cardiolipin.

The lipids can also include derivatized lipids, such as PEGylated lipids. PEGylated lipids generally contain a lipid moiety as described herein that is covalently conjugated to one or more PEG chains. The PEG can be linear or branched, wherein branched PEG molecules can have additional PEG molecules emanating from a central core and/or multiple PEG molecules can be grafted to the polymer backbone. PEG can include low or high molecular weight PEG, e.g., PEG500, PEG2000, PEG3400, PEG5000, PEG6000, PEG9000, PEG10000, PEG20000, or PEG50000 wherein the number, e.g., 500, indicates the average molecular weight. Derivatized lipids can include, for example, DSPE-PEG2000, cholesterol-PEG2000, DSPE-polyglycerol, or other derivatives generally well known in the art.

Accordingly, some embodiments of the present invention provide particles as described above further comprising a PEGylated lipid. In some embodiments, the PEGylated lipid can be DSPE-PEG2000. Any suitable amount of PEGylated lipid can be used to form the mixed micelles. In general, the ratio of the PEGylated lipid to the peptide conjugate is from about 0.1:1 to about 10:1 by weight. The ratio of the PEGylated lipid to the helix-bundle conjugate can be, for example, about 0.1:1, 0.5:1, 1:1, 2.5:1, 5:1, or 10:1 by weight. Other amounts of the PEGylated lipid can be useful in the particles of the invention, depending on the structure of the PEGylated lipid itself as well as the identity of the peptide conjugate. In some embodiments, the particles can include DSPE-PEG2000 and a peptide conjugate as described above in a ratio of about 1:1 by weight.

IV. Methods of Preparing Nanoparticles

The nanoparticles of the present invention can be prepared by any suitable method known to one of skill in the art. For example, the nanoparticles can be prepared by first dissolving the conjugates in a suitable solvent at any concentration from about 1 nM to about 1M, or from about 1 μM to about 100 mM, or from about 1 mM to about 100 mM. Alternatively, the conjugates can be dissolved at a concentration of from about 0.1 to about 50 wt. % of the solution, or from about 1 to about 50 wt. %, or from about 1 to about 25 wt. %. The conjugates self-assemble to form the helix bundles of the present invention. The helix bundles then self-assemble to form the particles. In some embodiments, the present invention provides a method of forming particles of the present invention by maintaining a plurality of conjugates of the present invention under conditions sufficient to allow the conjugates to self-assemble into the particles of the present invention. In some embodiments, the conjugates are at a concentration of from about 1 nM to about 1 M. In some embodiments, the conjugates are at a concentration of from about 1 μM to about 1 M. In some embodiments, the conjugates are at a concentration of from about 1 μM to about 1 100 mM. In some embodiments, the conjugates are at a concentration of from about 1 μM to about 1 mM.

The methods of the invention can also be used to form mixed micelles above. Accordingly, additional compounds such as PEGylated lipids can be used for co-assembly with the peptide conjugates. In some embodiments, the present invention provides a method of forming particles by maintaining a plurality of conjugates under conditions sufficient to allow the conjugates to self-assemble into the particles, and by further adding a PEGylated lipid to the plurality of conjugates.

In an aqueous solvent, the conjugates of the present invention can self-assemble such that the hydrophilic portion is oriented towards the exterior of the nanocarrier and the hydrophobic portion is oriented towards the interior, thus forming a micelle. When a non-polar solvent is used, an inverse micelle can be formed where the hydrophilic portion is oriented towards the interior of the nanocarrier and the hydrophobic portion is oriented towards the exterior of the nanocarrier.

V. Methods for Drug Delivery

In some embodiments, the present invention provides a method for delivering a diagnostic or therapeutic agent to a subject comprising administering a particle to the subject. In some embodiments, the particle encapsulates the diagnostic or therapeutic agent. In other embodiments, the diagnostic or therapeutic agent is conjugated or coupled to the particle of the present invention. Thus, the particle includes from about 20 to about 200 conjugates of the present invention and the diagnostic or therapeutic agent to be delivered. In some embodiments, the therapeutic agent is selected from the group consisting of doxorubicin, temzolomide, and rapamycin.

Delivery of the therapeutic agent can be conducted such that drug-loaded micelles selectively accumulate at a desired site in a subject, such as a specific organ or a tumor. In some cases, micelle accumulation at a target site may be due to the enhanced permeability and retention characteristics of certain tissues such as cancer tissues. Accumulation in such a manner can arise, in part, from the micelle size and may not require special targeting functionality. In other cases, the micelles of the present invention can also include ligands for active targeting as described above. Target delivery can also be accomplished by administering drug-loaded micelles directed to a desired site. In some embodiments, delivery of a therapeutic agent can include administering a particle of the present invention via intra-tumoral infusion.

The nanoparticles of the present invention can be used to deliver any suitable cargo in a targeted or untargeted fashion. Suitable cargo includes, but is not limited to, vaccines, nucleic acids such as DNA or RNA, peptides, proteins, imaging agents, and drugs. The nanoparticles of the present invention are also useful for gene therapy, the administration of an expressed or expressible nucleic acid to a subject.

The nanocarrier cargo can be encapsulated within the nanocarrier.

Targeting Agents

Generally, the targeting agents of the present invention can associate with any target of interest, such as a target associated with an organ, tissues, cell, extracellular matrix, or intracellular region. In certain embodiments, a target can be associated with a particular disease state, such as a cancerous condition. In some embodiments, the targeting component can be specific to only one target, such as a receptor. Suitable targets can include but are not limited to a nucleic acid, such as a DNA, RNA, or modified derivatives thereof. Suitable targets can also include but are not limited to a protein, such as an extracellular protein, a receptor, a cell surface receptor, a tumor-marker, a transmembrane protein, an enzyme, or an antibody. Suitable targets can include a carbohydrate, such as a monosaccharide, disaccharide, or polysaccharide that can be, for example, present on the surface of a cell.

In certain embodiments, a targeting agent can include a target ligand, a small molecule mimic of a target ligand, or an antibody or antibody fragment specific for a particular target. In some embodiments, a targeting agent can further include folic acid derivatives, B-12 derivatives, integrin RGD peptides, NGR derivatives, somatostatin derivatives or peptides that bind to the somatostatin receptor, e.g., octreotide and octreotate, and the like. The targeting agents of the present invention can also include an aptamer. Aptamers can be designed to associate with or bind to a target of interest. Aptamers can be comprised of, for example, DNA, RNA, and/or peptides, and certain aspects of aptamers are well known in the art. (See. e.g., Klussman, S., Ed., The Aptamer Handbook, Wiley-VCH (2006); Nissenbaum, E. T., Trends in Biotech. 26(8): 442-449 (2008)).

Therapeutic Agents

The therapeutic agent or agents used in the present invention can include any agent directed to treat a condition in a subject. In general, any therapeutic agent known in the art can be used, including without limitation agents listed in the United States Pharmacopeia (U.S.P.), *Goodman and Gilman's The Pharmacological Basis of Therapeutics*, $10^{th}$ Ed., McGraw Hill, 2001; Katzung, Ed., *Basic and Clinical Pharmacology*, McGraw-Hill/Appleton & Lange, $8^{th}$ ed., Sep. 21, 2000; *Physician's Desk Reference* (Thomson Publishing; and/or *The Merck Manual of Diagnosis and Therapy*, $18^{th}$ ed., 2006, Beers and Berkow, Eds., Merck Publishing Group; or, in the case of animals, *The Merck Veterinary Manual*, 9th ed., Kahn Ed., Merck Publishing Group, 2005; all of which are incorporated herein by reference.

Therapeutic agents can be selected depending on the type of disease desired to be treated. For example, certain types of cancers or tumors, such as carcinoma, sarcoma, leukemia, lymphoma, myeloma, and central nervous system cancers as well as solid tumors and mixed tumors, can involve administration of the same or possibly different therapeutic agents. In certain embodiments, a therapeutic agent can be delivered to treat or affect a cancerous condition in a subject and can include chemotherapeutic agents, such as alkylating agents, antimetabolites, anthracyclines, alkaloids, topoisomerase inhibitors, and other anticancer agents. In some embodiments, the agents can include antisense agents, microRNA, siRNA and/or shRNA agents.

Therapeutic agents can include an anticancer agent or cytotoxic agent including but not limited to avastin, doxorubicin, temzolomide, rapamycin, platins such as cisplatin, oxaliplatin and carboplatin, cytidines, azacytidines, 5-fluorouracil (5-FU), gemcitabine, capecitabine, camptothecin, bleomycin, daunorubicin, vincristine, topotecan or taxanes, such as paclitaxel and docetaxel.

Therapeutic agents of the present invention can also include radionuclides for use in therapeutic applications. For example, emitters of Auger electrons, such as $^{111}$In, can be combined with a chelate, such as diethylenetriaminepentaacetic acid (DTPA) or 1,4,7,10-tetraazacyclododecane-1,4,7,10-tetraacetic acid (DOTA), and included in a nanoparticle to be used for treatment. Other suitable radionuclide and/or radionuclide-chelate combinations can include but are not limited to beta radionuclides ($^{177}$Lu, $^{153}$Sm, $^{88/90}$Y) with DOTA, $^{64}$Cu-TETA, $^{188/186}$Re(CO)$_3$-IDA; $^{188/186}$Re(CO)triamines (cyclic or linear), $^{188/186}$Re(CO)$_3$ Enpy2, and $^{188/186}$Re(CO)$_3$-DTPA.

Diagnostic Agents

A diagnostic agent used in the present invention can include any diagnostic agent known in the art, as provided, for example, in the following references: Armstrong et al., *Diagnostic Imaging*, $5^{th}$ Ed., Blackwell Publishing (2004); Torchilin, V. P., Ed., *Targeted Delivery of Imaging Agents*, CRC Press (1995); Vallabhajosula, S., *Molecular Imaging: Radiopharmaceuticals for PET and SPECT*, Springer (2009). A diagnostic agent can be detected by a variety of ways, including as an agent providing and/or enhancing a detectable signal that includes, but is not limited to, gamma-emitting, radioactive, echogenic, optical, fluorescent, absorptive, magnetic or tomography signals. Techniques for imaging the diagnostic agent can include, but are not limited to, single photon emission computed tomography (SPECT), magnetic resonance imaging (MRI), optical imaging, positron emission tomography (PET), computed tomography (CT), x-ray imaging, gamma ray imaging, and the like.

In some embodiments, a diagnostic agent can include chelators that bind to metal ions to be used for a variety of diagnostic imaging techniques. Exemplary chelators include but are not limited to ethylenediaminetetraacetic acid (EDTA), [4-(1,4,8, 11-tetraazacyclotetradec-1-yl) methyl] benzoic acid (CPTA), cyclohexanediaminetetraacetic acid (CDTA), ethylenebis(oxyethylenenitrilo)tetraacetic acid (EGTA), diethylenetriaminepentaacetic acid (DTPA), citric acid, hydroxyethyl ethylenediamine triacetic acid (HEDTA), iminodiacetic acid (IDA), triethylene tetraamine hexaacetic acid (TTHA), 1,4,7, 10-tetraazacyclododecane-1,4,7,10-tetra(methylene phosphonic acid) (DOTP), 1,4,8,11-tetraazacyclododecane-1,4,8,11-tetraacetic acid (TETA), 1,4,7, 10-tetraazacyclododecane-1,4,7,10-tetraacetic acid (DOTA), and derivatives thereof.

A radioisotope can be incorporated into some of the diagnostic agents described herein and can include radionuclides that emit gamma rays, positrons, beta and alpha particles, and X-rays. Suitable radionuclides include but are not limited to $^{225}$Ac, $^{72}$As, $^{211}$At, $^{11}$B, $^{128}$Ba, $^{212}$Bi, $^{75}$Br, $^{77}$Br, $^{14}$C, $^{109}$Cd, $^{62}$Cu, $^{64}$Cu, $^{64}$Cu, $^{67}$Cu, $^{18}$F, $^{67}$Ga, $^{68}$Ga, $^{3}$H, $^{123}$I, $^{125}$I, $^{130}$I, $^{131}$I, $^{111}$In, $^{177}$Lu, $^{13}$N, $^{15}$O, $^{32}$P, $^{33}$P, $^{212}$Pb, $^{103}$Pd, $^{186}$Re, $^{188}$Re, $^{47}$Sc, $^{153}$Sm, $^{89}$Sr, $^{99m}$Tc, $^{88}$Y and $^{90}$Y. In certain embodiments, radioactive agents can include $^{111}$In-DTPA, $^{99m}$Tc(CO)$_3$-DTPA, $^{99m}$Tc(CO)$_3$-ENPy2, $^{62/64/67}$Cu-TETA, $^{99m}$Tc(CO)$_3$-IDA, and $^{99m}$Tc(CO)$_3$triamines (cyclic or linear). In other embodiments, the agents can include DOTA and its various analogs with $^{111}$In, $^{177}$Lu, $^{153}$Sm, $^{88/90}$Y, $^{62/64/67}$Cu, or $^{67/68}$Ga. In some embodiments, the micelles can be radiolabeled, for example, by incorporation of chelating groups, such as DTPA-lipid, as provided in the following references: Phillips et al., *Wiley Interdisciplinary Reviews: Nanomedicine and Nanobiotechnology*, 1(1): 69-83 (2008); Torchilin, V. P. & Weissig, V., Eds. *Liposomes* 2nd Ed.: Oxford Univ. Press (2003); Elbayoumi, T. A. & Torchilin, V. P., *Eur. J. Nucl. Med. Mol. Imaging* 33:1196-1205 (2006); Mougin-Degraef, M. et al., *Intl J. Pharmaceutics* 344:110-117 (2007).

In other embodiments, the diagnostic agents can include optical agents such as fluorescent agents, phosphorescent agents, chemiluminescent agents, and the like. Numerous agents (e.g., dyes, probes, labels, or indicators) are known in the art and can be used in the present invention. (See, e.g., Invitrogen, The Handbook-A Guide to Fluorescent Probes and Labeling Technologies, Tenth Edition (2005)). Fluorescent agents can include a variety of organic and/or inorganic small molecules or a variety of fluorescent proteins and derivatives thereof. For example, fluorescent agents can include but are not limited to cyanines, phthalocyanines, porphyrins, indocyanines, rhodamines, phenoxazines, phenylxanthenes, phenothiazines, phenoselenazines, fluoresceins, benzoporphyrins, squaraines, dipyrrolo pyrimidones, tetracenes, quinolines, pyrazines, corrins, croconiums, acridones, phenanthridines, rhodamines, acridines, anthraquinones, chalcogenopyrylium analogues, chlorins, naphthalocyanines, methine dyes, indolenium dyes, azo compounds, azulenes, azaazulenes, triphenyl methane dyes, indoles, benzoindoles, indocarbocyanines, benzoindocarbocyanines, and BODIPY™ derivatives having the general structure of 4,4-difluoro-4-bora-3a,4a-diaza-s-indacene, and/or conjugates and/or derivatives of any of these. Other agents that can be used include, but are not limited to, for example, fluorescein, fluorescein-polyaspartic acid conjugates, fluorescein-polyglutamic acid conjugates, fluorescein-polyarginine conjugates, indocyanine green, indocyanine-dodecaaspartic acid conjugates, indocyanine-polyaspartic acid conjugates, isosulfan blue, indole disulfonates, benzoindole disulfonate, bis(ethylcarboxymethyl)indocyanine, bis(pentylcarboxymethyl)indocyanine, polyhydroxyindole sulfonates, polyhydroxybenzoindole sulfonate, rigid heteroatomic indole sulfonate, indocyaninebispropanoic acid, indocyaninebishexanoic acid, 3,6-dicyano-2,5-[(N,N,N',N'-tetrakis(carboxymethyl)amino]pyrazine, 3,6-[(N,N,N',N'-tetrakis(2-hydroxyethyl)amino]pyrazine-2,5-dicarboxylic acid, 3,6-bis(N-azatedino)pyrazine-2,5-dicarboxylic acid, 3,6-bis(N-morpholino)pyrazine-2,5-dicarboxylic acid, 3,6-bis(N-piperazino)pyrazine-2,5-dicarboxylic acid, 3,6-bis(N-thiomorpholino)pyrazine-2,5-dicarboxylic acid, 3,6-bis(N-thiomorpholino)pyrazine-2,5-dicarboxylic acid S-oxide, 2,5-dicyano-3,6-bis(N-thiomorpholino)pyrazine S,S-dioxide, indocarbocyaninetetrasulfonate, chloroindocarbocyanine, and 3,6-diaminopyrazine-2,5-dicarboxylic acid.

One of ordinary skill in the art will appreciate that particular optical agents used can depend on the wavelength used for excitation, depth underneath skin tissue, and other factors generally well known in the art. For example, optimal absorption or excitation maxima for the optical agents can vary depending on the agent employed, but in general, the optical agents of the present invention will absorb or be excited by light in the ultraviolet (UV), visible, or infrared (IR) range of the electromagnetic spectrum. For imaging, dyes that absorb and emit in the near-IR (~700-900 nm, e.g., indocyanines) are preferred. For topical visualization using an endoscopic method, any dyes absorbing in the visible range are suitable.

In yet other embodiments, the diagnostic agents can include but are not limited to magnetic resonance (MR) and x-ray contrast agents that are generally well known in the art, including, for example, iodine-based x-ray contrast agents, superparamagnetic iron oxide (SPIO), complexes of gadolinium or manganese, and the like. (See, e.g., Armstrong et al., *Diagnostic Imaging*, 5$^{th}$ Ed., Blackwell Publishing (2004)). In some embodiments, a diagnostic agent can include a magnetic resonance (MR) imaging agent. Exemplary magnetic resonance agents include but are not limited to paramagnetic agents, superparamagnetic agents, and the like. Exemplary paramagnetic agents can include but are not limited to gadopentetic acid, gadoteric acid, gadodiamide, gadolinium, gadoteridol, mangafodipir, gadoversetamide, ferric ammonium citrate, gadobenic acid, gadobutrol, or gadoxetic acid. Superparamagnetic agents can include but are not limited to superparamagnetic iron oxide and ferristene. In certain embodiments, the diagnostic agents can include x-ray contrast agents as provided, for example, in the following references: H. S Thomsen, R. N. Muller and R. F. Mattrey, Eds., *Trends in Contrast Media*, (Berlin: Springer-Verlag, 1999); P. Dawson, D. Cosgrove and R. Grainger, Eds., *Textbook of Contrast Media* (ISIS Medical Media 1999); Torchilin, V. P., *Curr. Pharm. Biotech.* 1:183-215 (2000); Bogdanov, A. A. et al., *Adv. Drug Del. Rev.* 37:279-293 (1999); Sachse, A. et al., *Investigative Radiology* 32(1):44-50 (1997). Examples of x-ray contrast agents include, without limitation, iopamidol, iomeprol, iohexol, iopentol, iopromide, iosimide, ioversol, iotrolan, iotasul, iodixanol, iodecimol, ioglucamide, ioglunide, iogulamide, iosarcol, ioxilan, iopamiron, metrizamide, iobitridol and iosimenol. In certain embodiments, the x-ray contrast agents can include iopamidol, iomeprol, iopromide, iohexol, iopentol, ioversol, iosimenol, iobitridol, iodixanol, iotrolan and iosimenol.

Gene Therapy

The nanoparticles of the present invention can also be used to deliver any expressed or expressible nucleic acid sequence to a cell for gene therapy or nucleic acid vaccination. The cells can be in vivo or in vitro during delivery. The nucleic acids can be any suitable nucleic acid, such as deoxyribonucleic acid (DNA) or ribonucleic acid (RNA). Moreover, any suitable cell can be used for delivery of the nucleic acids.

Gene therapy can be used to treat a variety of diseases, such as those caused by a single-gene defect or multiple-gene defects, by supplementing or altering genes within the host cell, thus treating the disease. Typically, gene therapy involves replacing a mutated gene, but can also include correcting a gene mutation or providing DNA encoding for a therapeutic protein. Gene therapy also includes delivery of a nucleic acid that binds to a particular messenger RNA (mRNA) produced by the mutant gene, effectively inactivating the mutant gene, also known as antisense therapy. Representative diseases that can be treated via gene and antisense therapy include, but are not limited to, cystic fibrosis, hemophilia, muscular dystrophy, sickle cell anemia, cancer, diabetes, amyotrophic lateral sclerosis (ALS), inflammatory diseases such as asthma and arthritis, and color blindness.

For general reviews of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIBTECH 11(5): 155-215. Methods commonly known in the art of recombinant DNA technology which can be used in the present invention are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

Formulation and Administration

When the nanocarriers are administered to deliver the cargo as described above, the nanocarriers can be in any suitable composition with any suitable carrier, i.e., a physiologically acceptable carrier. As used herein, the term "carrier" refers to a typically inert substance used as a diluent or vehicle for a drug such as a therapeutic agent. The term also encompasses a typically inert substance that imparts cohesive qualities to the composition. Typically, the physiologically acceptable carriers are present in liquid form. Examples of liquid carriers include physiological saline, phosphate buffer, normal buffered saline, water, buffered water, saline, glycine, glycoproteins to provide enhanced stability (e.g., albumin, lipoprotein, globulin, etc.), and the like. Since physiologically acceptable carriers are determined in part by the particular composition being administered as well as by the particular method used to administer the composition, there are a wide variety of suitable formulations of pharmaceutical compositions of the present invention (See, e.g., Remington's Pharmaceutical Sciences, 17$^{th}$ ed., 1989).

Prior to administration, the nanocarrier compositions can be sterilized by conventional, well-known sterilization techniques or may be produced under sterile conditions. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents, wetting agents, and the like, e.g., sodium acetate, sodium lactate, sodium chloride, potassium chloride, calcium chloride, sorbitan monolaurate, and triethanolamine oleate. Sugars can also be included for stabilizing the compositions, such as a stabilizer for lyophilized compositions.

The nanocarrier compositions can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which includes an effective amount of a packaged composition with a suppository base. Suitable suppository bases include natural or synthetic triglycerides or paraffin hydrocarbons. In addition, it is also possible to use gelatin rectal capsules which contain a combination of the composition of choice with a base, including, for example, liquid triglycerides, polyethylene glycols, and paraffin hydrocarbons.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Injection solutions and suspensions can also be prepared from sterile powders, granules, and tablets. In the practice of the present invention, compositions can be administered, for example, by intravenous infusion, topically, intraperitoneally, intravesically, or intrathecally. Parenteral administration—including intravenous administration—is the preferred method of administration.

Conjugates, particles, and formulations of the present invention can also be delivered by infusion directly into an area of the brain (such as the striatum or a brain tumor) by convection-enhanced delivery (CED), a technique that uses a pressure gradient established at the tip of an infusion catheter to initiate bulk flow that forces the infusate through the space between brain cells (i.e. the extracellular space). An infusion pump or an osmotic pump can be used for CED. Using CED devices, the conjugates, particles, and compositions of the invention can be delivered to many cells over large areas of the brain. CED is described, for example, in U.S. Pat. Nos. 6,953,575; 7,534,613; and 8,309,355.

The pharmaceutical preparation is preferably in unit dosage form. In such form the preparation is subdivided into unit doses containing appropriate quantities of the active component, e.g., a nanocarrier composition. The unit dosage form can be a packaged preparation, the package containing discrete quantities of preparation. The formulations of nanocarrier compositions can be presented in unit-dose or multi-dose sealed containers, such as ampoules and vials. The composition can, if desired, also contain other compatible therapeutic agents.

In therapeutic use, the nanocarrier compositions including a therapeutic and/or diagnostic agent, as described above, can be administered at the initial dosage of about 0.001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, can be varied depending upon the requirements of the patient, the severity of the condition being treated, and the nanocarrier composition being employed. For example, dosages can be empirically determined considering the type and stage of cancer diagnosed in a particular patient. The dose administered to a patient, in the context of the present invention, should be sufficient to affect a beneficial therapeutic response in the patient over time. The size of the dose will also be determined by the existence, nature, and extent of any adverse side-effects that accompany the administration of a particular nanocarrier composition in a particular patient. Determination of the proper dosage for a particular situation is within the skill of the practitioner. Generally, treatment is initiated with smaller dosages which are less than the optimum dose of the nanocarrier composition. Thereafter, the dosage is increased by small increments until the optimum effect under circumstances is reached. For convenience, the total daily dosage can be divided and administered in portions during the day, if desired.

Loading of Nanocarriers

Loading of the diagnostic and therapeutic agents can be carried out through a variety of ways known in the art, as disclosed for example in the following references: de Villiers, M. M. et al., Eds., *Nanotechnology in Drug Delivery*, Springer (2009); Gregoriadis, G., Ed., *Liposome Technology: Entrapment of drugs and other materials into liposomes*, CRC Press (2006). In some embodiments, one or more therapeutic agents can be loaded into the nanocarriers. Loading of nanocarriers can be carried out, for example, in an active or passive manner. For example, a therapeutic agent can be included during the self-assembly process of the nanocarriers in a solution, such that the therapeutic agent is encapsulated within the nanocarrier. In certain embodiments, the therapeutic agent may also be embedded in the lamellar layer. In alternative embodiments, the therapeutic agent can be actively loaded into the nanocarriers. For example, the nanocarriers can be exposed to conditions, such as electroporation, in which the lamellar membrane is made permeable to a solution containing therapeutic agent thereby allowing for the therapeutic agent to enter into the internal volume of the liposomes.

The diagnostic and therapeutic agents can also be covalently or ionically linked to the surface of the nanocarrier, in the interior of the micelle, or within the lamellar layer of the micelle.

VI. Methods for Disease Treatment

In some embodiments, the present invention provides a method for treating a subject with a disease. The method includes administering a therapeutically effective amount of a particle to the subject. The particle includes from about 20 to about 200 conjugates of the present invention and at least one therapeutic agent. Thus, the disease is treated.

Any suitable disease can be treated using the conjugates and particles of the present invention. Representative diseases include cancer and Parkinson's disease, among others. Cancers contemplated for treatment using the methods of the present invention include carcinomas, gliomas, mesotheliomas, melanomas, lymphomas, leukemias, adenocarcinomas, breast cancer, ovarian cancer, cervical cancer, glioblastoma, leukemia, lymphoma, prostate cancer, and Burkitt's lymphoma, brain and central nervous system, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, cervical cancer, vaginal cancer, uterine cancer, ovarian cancer, thyroid cancer, parathyroid cancer, adrenal cancer, pancreatic endocrine cancer, carcinoid cancer, bone cancer, skin cancer, retinoblastomas, Hodgkin's lymphoma, and non-Hodgkin's lymphoma. In some embodiments, the present invention provides a method for treating a subject with a cancer characterized by solid tumors. In some embodiments, the disease is selected from the group consisting of a cancer and Parkinson's disease. In some embodiments, the cancer is Glioblastoma multiforme.

In some embodiments, the present invention provides a method for treating a subject with brain cancer. Brain cancers include gliomas, meningiomas, pituitary adenomas, and nerve sheath tumors. In some embodiments, the brain cancer is Glioblastoma multiforme. Glioblastoma multiforme presents variants including giant cell glioblastoma and gliosarcoma.

The particles of the invention can be used in conjunction or concurrently with other known methods of disease treatment, including—but not limited to—chemotherapy and radiotherapy. Any suitable therapeutic agent is useful in combination with the conjugates and particles of the present invention. In some embodiments, the therapeutic agent is selected from the group consisting of doxorubicin, temzolomide, and rapamycin. In some embodiments, the at least one therapeutic agent can be doxorubicin, paclitaxel or rapamycin. In other embodiments, the therapeutic agent is doxorubicin.

In some embodiments, the present invention provides a method of treating a disease state in a human subject, including administering a therapeutically effective amount of a particle of the present invention, and at least one therapeutic agent. In some embodiments, the disease state can be cancer, autoimmune disorders, genetic disorders, infections, inflammation, neurologic disorders, or metabolic disorders. In some embodiments, the therapeutic agent can be a vaccine, nucleic acid or peptide.

VII. Examples

Example 1: Synthesis of Bis-Polymer Lipid-Peptide Conjugates

Materials. Fmoc-protected amino acids, 2-(1H-Benzotriazole-1-yl)-1,1,3,3-tetramethyluronium hexafluorophosphate (HBTU), 2-(6-Chloro-1H-benzotriazole-1-yl)-1,1,3,3-tetramethylaminium hexafluorophosphate (HCTU) were purchased from EMD biosciences and used without further purification. The side chain protecting groups of the Fmoc-protected amino acids were as follows: Lys(Boc), Glu (OtBu), Asp(OtBu), Cys(Trt), Arg(Pbf), His(Trt), Trp(Boc), Gln(Trt), Lys(Alloc). In addition, Fmoc-Lys(Fmoc)-OH was used for the conjugation of stearic acid to peptide, and a linker, Fmoc-6-Ahx-OH (Sigma Aldrich) was appended between the peptide and the alkyl tails. Peptide synthesis grade diethylpropylamine (DIPEA), trifluoroacetic acid (TFA), triisopropylsilane (TIS), diethyl ether, HPLC grade organic solvent dimethylformamide (DMF), dichloromethane (DCM), acetonitrile and isopropanol were purchased from Fisher and used without further purification. Piperidine, stearic acid and doxorubicin were purchased from Sigma Aldrich. PEG(2000)-maleimide and PEG(750)-COOH ester were purchased from Rapp Polymere. Negative stain reagent phosphotungstic acid was purchased from Ted Pella and prepared as a 2 wt % stock solution in DI water.

Material Synthesis.

"1coi" (EVEALEKKVAALECKVQALEKKVEALE-HGW; SEQ ID NO:1) is a de novo designed 3-helix bundle peptide and was synthesized on a Protein Technologies Prelude solid phase synthesizer using standard 9-fluorenyl-methyl carbamate (Fmoc) protection chemistry on PEG-PAL resin (Applied Biosystems), typically at 0.05 mmol scale. Fmoc-Lys(Fmoc)-OH (EMD Bioscience) was appended to the N-terminus to allow coupling of stearic acid molecules to the N-terminus of the peptide. To modify the C-terminus of the peptide with PEG750, a tri-glycine spacer and Fmoc-Lys(Alloc)-OH were coupled at the C-terminus. The Alloc group was selectively removed by utilizing Pd(PPh$_3$)$_4$ catalyst and radical trapping agent PhSiH$_3$ in DCM. The reaction was repeated five times. The resulting free amino groups of lysine were utilized for conjugating carboxy terminated PEG750 using HBTU/DIPEA chemistry. The coupling reaction was performed at room temperature for 24 hours and repeated twice. Peptides were then cleaved from the resin using standard procedures. Cysteine at position 14 facilitates the site-specific coupling of maleimide-functionalized PEG of molecular weight 2000 g/mol to the middle of the peptide sequence. Cysteine at the C-terminus of dC18-1coi(PEG2K)-PEG750 allows for the conjugation of 6-BAT-maleimide onto the peptides for PET imaging.

Reversed-Phase High-Pressure Liquid Chromatography (RP-HPLC).

The amphiphilic conjugates were purified using RP-HPLC (Beckman Coulter) on a C4 column (Vydac column 22 mm×250 mm). The flow rate was 10 ml/min for semi-preparative runs and conjugates were injected at a concentration of 10 mg/ml. Elution was monitored with a diode array detector at wavelengths of 220 nm and 280 nm. Conjugates were eluted with a linear AB gradient, where solvent A consisted of water plus 0.1% (v/v) TFA and solvent B consisted of isopropanol plus 0.1% (v/v) TFA. A linear gradient of 30 to 100% B over 30 min was used, with typical elution of the amphiphile at ~85% B. Purification yield was ~30%.

MALDI-TOF Spectrometry.

The identity and purity of the peptides were verified by MALDI-TOF mass spectrometry using α-cyano-4-hydroxycinnamic acid matrix. Mass spectra were recorded on an Applied BioSystems Voyager-DE Pro.

Results and Discussion: Amphiphilic Peptide-Polymer Design and Synthesis.

The amphiphile is schematically shown in FIG. 1. The headgroup is composed of a newly designed peptide-poly (ethylene glycol) (PEG) conjugate where the PEG chain is attached to the middle of a 3-helix bundle forming peptide (Protein data bank code "1coi"). Two C18 acyl chains were attached at the peptide N-terminus with a (6)-aminohexanoic acid linker inserted between the peptide and the alkyl tail to introduce amphiphilicity. Another PEG chain is attached to the peptide C-terminus. The resulting amphiphile is termed as "dC18-1coi(PEG2K)-PEG750;" PEG2K (or P2K) in the parentheses of the term refers to the 2000 Da PEG chain that is conjugated to the middle of the peptide, while PEG750 (or P750) refers to the 750 Da PEG chain that is conjugated to the peptide C terminus. The name of the bis-polymer conjugate can also be shortened to "dC18-P750", referring to a bis-polymer conjugate having a 1coi peptide with a dC18 lipid at the N-terminus, a PEG2k conjugated to the middle of the peptide, and a PEG750 conjugated to the C-terminus. Conjugates without a C-terminal polymer are referred to using labels such as "dC18-1coi(PEG2K)" and the like. The intermolecular interactions between peptides and the compression of PEG on the exterior of the helix bundle are believed to increase the activation energy barrier for subunit desorption and provide stability to the micelle. Upon forming micelles, peptide-PEG conjugates in the headgroup will self-associate into a trimeric subunit (FIG. 1b) and can provide a platform to investigate the effect of the oligomeric state of ligand presentation on active targeting for nanocarrier localization. The PEG chains attached to the exterior of the helix bundle may be used to tailor the inter-ligand cluster distance.

Figure 2A:
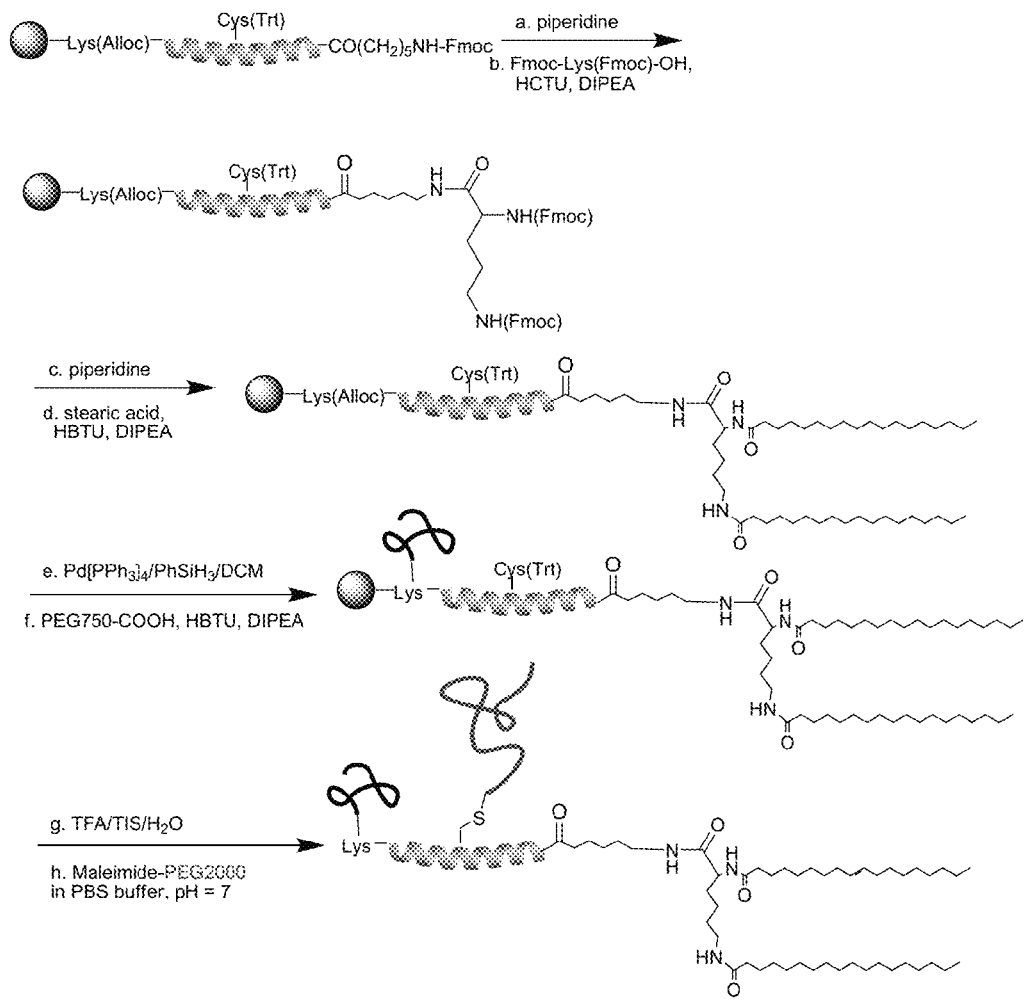
FIG. 2 shows (a) the synthetic scheme for preparation of amphiphilic bis-polymer lipid peptide conjugates, and (b) a MALDI-TOF spectrum for the conjugate dC18-1coi (PEG2K)-PEG750.
Figure 2B:
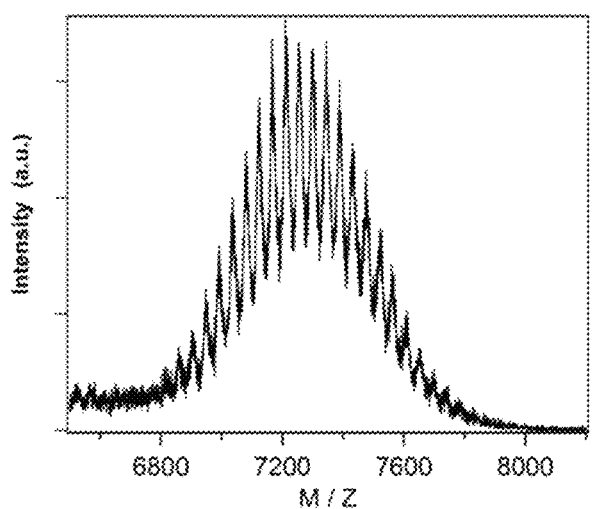

The peptide, based on 1coi, was synthesized using solid phase peptide synthesis (SPPS). The synthetic methodology for the amphiphiles is shown in FIG. 2a. Specifically, the alkyl chains were conjugated on solid phase through reaction of stearic acid with deprotected Fmoc-Lys(Fmoc)-OH to generate a branched alkyl tail at the N-terminus. Orthogonal protection-deprotection strategies were employed to link PEG molecules on both the side and the C-terminus. The C-terminus was modified through palladium catalyzed Alloc-deprotection of Fmoc-Lys(Alloc)-OH followed by conjugation of carboxy terminated organic molecules using HBTU/DIPEA chemistry. The resulting conjugate has the peptide sequence: EVEALEKKVAALECKVQALEKK-VEALEHGWGGGK (SEQ ID NO: 6). PEG 2000 is covalently bound to the cysteine sidechain, PEG 750 is covalently bound to the ε-amine of the C-terminal lysine, and stearic acid is covalently bound to the α-amine and the ε-amine of a lysine residue appended to a 6-aminohexanoic acid linker residue at the N-terminus. In this study, PEG ($M_W$=750 Da) was selected as the C-terminal functional group to stabilize the micelles as well as provide a stealth layer for prevention of non-specific protein absorption. A variety of targeting ligands can also be attached using the same chemistry. The conjugate was purified by reverse phase high pressure liquid chromatography (RP-HPLC) using a gradient of mixed solvents containing water (0.1% TFA) and isopropanol (0.1% TFA). The amphiphilic molecules eluted at ~85% isopropanol with the overall yield of 30%. The molecular weight was confirmed by MALDI-TOF spectrometry (FIG. 2b).

Example 2: Characterization and Loading of Bis-Polymer Lipid-Peptide Conjugate Micelles Negatively Stained Transmission Electron Microscopy.

Lyophilized peptide powder was dissolved at 0.1 mg/ml in 25 mM phosphate buffer at pH 7.4. 5 μl of peptide solution was dropped on a discharged holey carbon coated grid (Ted Pella 01824). After removing excess peptide solution, 5 μl of phosphotungstic acid (2 wt %, pH=3.3) solution was then applied for 2 minutes. Samples were dried in air and examined using a FEI Tecnai 12 transmission electron microscope at 120 kV.

Dynamic Light Scattering (DLS).

DLS size measurements were taken on a Malvern Zetasizer Nano-ZS with a 633 nm laser and a scattering angle of 17° to determine the hydrodynamic radius of samples in solution. Samples were passed through 0.22 μm filters prior to the measurements.

Size Exclusion Chromatography (SEC).

SEC was carried out on a BioSep-SEC-S 4000 column (Phenomenex). The flow rate was 1 ml/min with 25 mM phosphate buffer (pH=7.4) as the elution solvent. The elution profile was monitored with a UV-vis detector at one or more wavelengths of 220 nm, 280 nm and 480 nm.

Circular Dichroism (CD).

CD measurements were made on a Jasco J810 spectropolarimeter. CD spectra were collected from 260 to 190 nm at 0.2 nm intervals, a rate of 100 nm/min, a response time of 4 s, and a bandwidth of 1 nm. One hundred percent helicity was estimated using the formula $[\theta]_{222}=-40000\times[1-(2.5/n)]$.

Differential Scanning Calorimetry (DSC).

DSC was performed on a VP-MicroCal (GE). ~600 µl of sample (1 mg/ml) and buffer were loaded into two parallel stainless steel cells that were sealed tightly under a pressure of ~27 psi to prevent water evaporation during the heating cycle. The temperature was increased from 5° to 60° C. at a rate of 1° C./min, with a 15 min equilibration time at 5° C. DSC thermograms were obtained after concentration normalization and baseline correction using the Origin software provided by MicroCal.

Förster Resonance Energy Transfer (FRET).

A lipophilic FRET pair, 3,3'-dioctadecyloxacarbocyanine perchlorate (DiO, donor) and 1,1'-dioctadecyl-3,3,3',3'-tetramethylindocarbocyanine perchlorate (DiI, acceptor), were used to measure the energy transfer upon mixing. Desired amounts of DiO, DiI, and dC18-1coi(PEG2K)-PEG750 or DSPE-PEG2K were co-dissolved in a mixture of 1:1 chloroform and methanol. Organic solvents were evaporated under vacuum at 60° C. for at least 3 hours to form a thin film in a glass vial. Phosphate buffer (pH=7.4, 25 mM) was added to rehydrate the film at a concentration of 1 mg/ml. In cases where visible aggregates were formed, solutions were heated in a water bath at 70° C. for at least 30 mins to promote the homogeneity of the encapsulation. After 24 hours stirring at room temperature, the solutions were then subject to centrifugation and spin dialysis to remove any insoluble aggregates and soluble dyes in the supernatant. To 350 µl BSA sample was added 10 µl of the dye-encapsulated micelle solution and time dependent fluorescence intensity was recorded in the range of 475 nm to 650 nm for 12 hours with excitation wavelength at 450 nm.

Drug Loading and Release.

DOX, paclitaxel and rapamycin loaded micelles were prepared using identical procedures by thin film hydration method. dC18-1coi(P2K)-P750 and the different drugs were dissolved in methanol in a glass vial and the solvent was evaporated in vacuum oven for 3 hours. The dried film containing the conjugate and drug was rehydrated with 25 mM phosphate buffer, pH 7.4, and the solution was stirred for 16 hours to allow the assembly into drug loaded 3-helix micelles. Free drug was removed by centrifugation followed by spin ultrafiltration (Amicon centrifugal filter units, MW cutoff: 3000 Da). The concentrate obtained was washed with water and lyophilized to obtain drug loaded micelles. The drug loaded micelles were dissolved in methanol and loading was determined by reverse phase HPLC monitoring the absorbance of drugs at 280 nm. For all characterization experiments of drug loaded micelles, lyophilized powder of micellar-drugs was dissolved in 25 mM phosphate buffer, pH 7.4, and the solution was heated in water bath at 60° C. for an hour to break potential aggregates to obtain a clear solution.

Drug loaded 3-helix micelles were dissolved in 25 mM phosphate buffer, pH 7.4, at concentration of 3 mg/ml. Micellar-drug solution (2 ml) was placed in dialysis bags (SpectrumLabs) with molecular weight cut off (MWCO) of 8000 Da. The dialysis bags were then immersed in 1000 mL of PBS in a glass beaker that was stirred at 800 rpm. 10 µL of solution was taken from dialysis bags at different time points to measure the drug release as function of time. The released drug was quantified by reverse phase HPLC monitoring the absorbance at 280 nm.

Paclitaxel and rapamycin were also co-loaded with dye pairs in order to make FRET measurements as described above.

Results and Discussion: Physical Characterization of Amphiphilic Micelles.

Figure 3A:
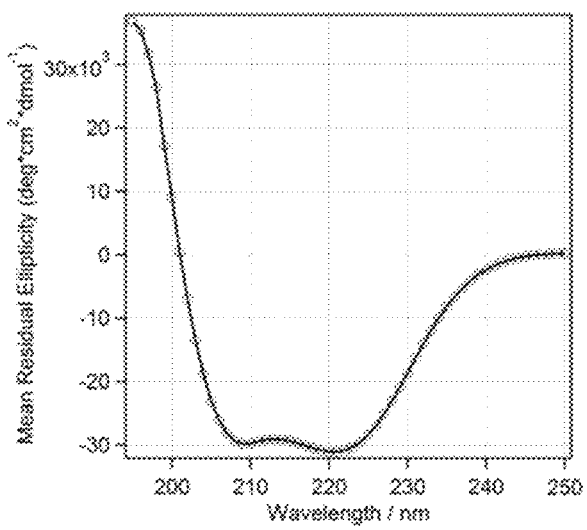
FIG. 3 shows the physical characterization of dC18-1coi (PEG2K)-PEG750 micelles using (a) circular dichroism, (b) dynamic light scattering, and (c) transmission electron microscopy.

The amphiphile, dC18-1coi(PEG2K)-PEG750, spontaneously self-assembles into micelles above its CMC value (~2 µM) in aqueous solution. FIG. 3a shows the circular dichroism (CD) spectrum of 200 µM solution of dC18-1coi (PEG2K)-PEG750 at 25° C. in phosphate buffer (pH=7.4, 25 mM). There are two peaks with minima at 208 nm and 222 nm, typical of a highly alpha helical structure. The 1coi peptide in the headgroup forms a helical structure with 82% helicity. The ratio of the molar ellipticities at 222 nm and 208 nm is routinely used to identify the presence of coiled-coil helices. For an isolated α-helix, the ratio was estimated to be 0.83, while for interacting alpha helices such as coiled-coils, the ratio was calculated to be ~1.0. The ratio between the ellipticities at 222 nm and 208 nm is 1.04, indicating that the tertiary structure of peptides, i.e. the coiled-coil helix bundle, is maintained within micelles.

Figure 3B:
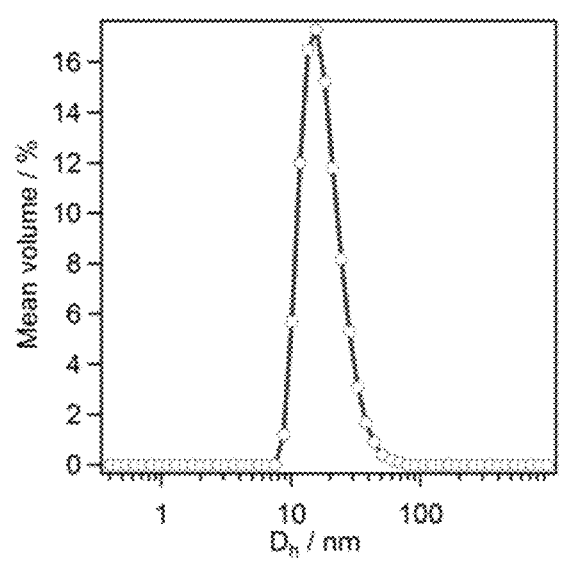
Figure 3C:
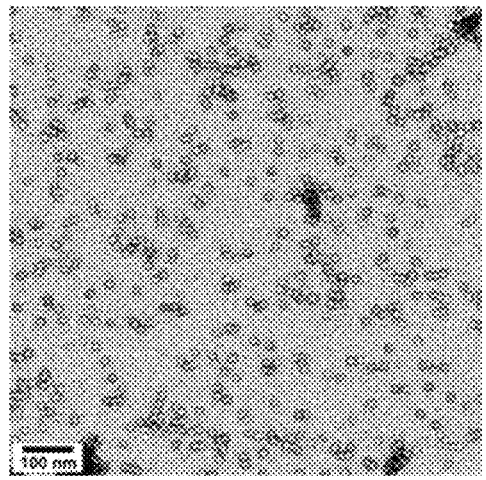

The packing parameter that quantifies the shape of amphiphiles was calculated using Israelachvili's surfactant number theory based on the size of the headgroup determined from x-ray and neutron scattering (unpublished results) and the crystal structure of 1coi. The packing parameter of a trimetric subunit, as shown in FIG. 1b, is calculated to be 0.238. For comparison, the packing parameter of individual amphiphiles, as schematically shown in FIG. 1a, is calculated to be 0.332. The formation of 3-helix bundles increases the cross-sectional mismatch between the headgroup and hydrophobic tails. Based on Israelachvili's surfactant number theory, the 3-helix bundle peptide-PEG conjugate has a strong preference for the formation of spherical micelles. After dissolving the lyophilized amphiphile powder into buffered solution, dynamic light scattering (DLS) (FIG. 3b) revealed a hydrodynamic diameter of 15 nm and a fairly uniform size distribution of micelles. Negatively stained TEM, as shown in FIG. 3c, provided further evidence that the amphiphiles (0.1 mg/mL in 25 mM phosphate buffer at pH 7.5) form spherical micelles with a diameter of ~15 nm.

In Vitro Stability by FRET.

The entrapped drug must be maintained inside the carriers until reaching the target site; however, in vivo cargo leakage remains a long-standing issue for micellar nanocarriers. For dye-loaded BCP micelles, in vivo FRET studies showed that dye molecules were released 15 min after intravenous injection. The in vitro stability of the 3-helix micelles was evaluated using FRET in the presence of bovine serum albumin (BSA), which is known as an amphiphile trap that disrupts micellar nanocarriers. A lipophilic FRET pair, 3,3'-dioctadecyloxacarbocyanine perchlorate (DiO, donor) and 1,1'-dioctadecyl-3,3,3',3'-tetramethylindocarbocyanine perchlorate (DiI, acceptor), were co-encapsulated in dC18-1coi (PEG2K)-PEG750 micelles. As the control experiment, the same FRET dyes were co-encapsulated in conventional micelles based on 1,2-distearoyl-sn-glycero-3-phosphoethanolamine-N-[methoxy(polyethylene glycol)-2000], (DSPE-PEG2K). Dye-encapsulated micelles were diluted in a physiological concentration of BSA (50 mg/ml) at 37° C. and fluorescence was monitored in the range of 475 nm-600 nm with $\lambda_{ex}$ 450 nm.

Figure 4A:
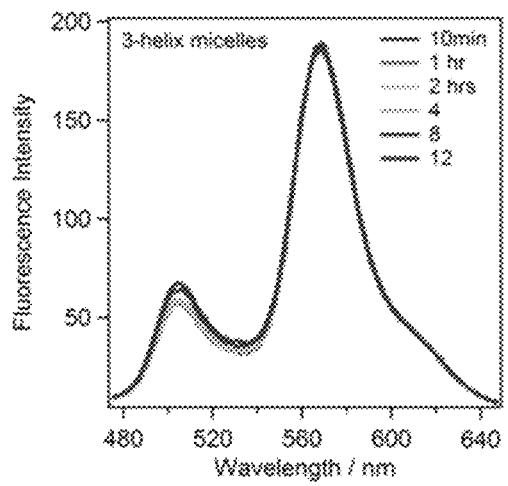
FIG. 4 shows the evaluation of dC18-1coi(PEG2K)-PEG750 micelle stability in vitro. Time resolved FRET data was compared for FIG. 4(a) dC18-1coi(PEG2K)-PEG750 micelles and FIG. 4(b) DSPE-PEG2K micelles. Normalized FRET data is plotted in FIG. 4(c).
Figure 4B:
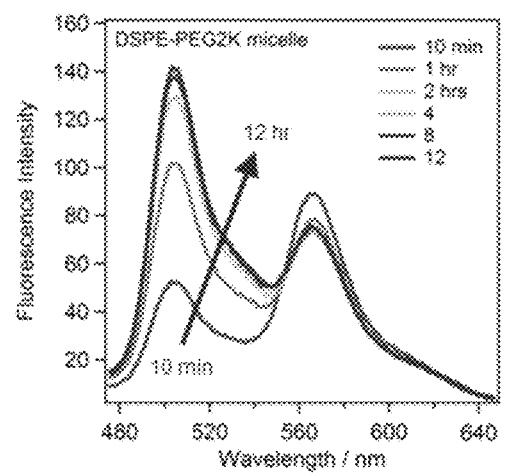
Figure 4C:
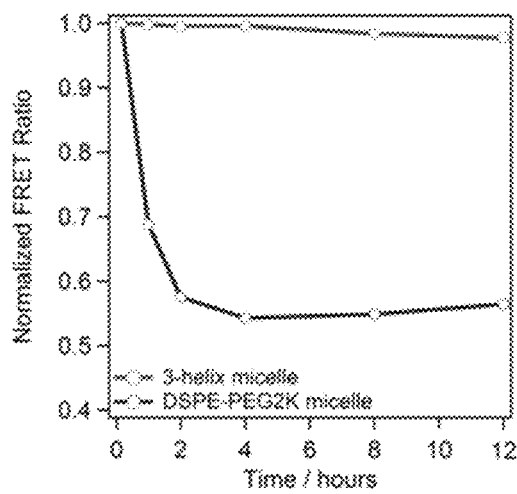
Figure 5A:
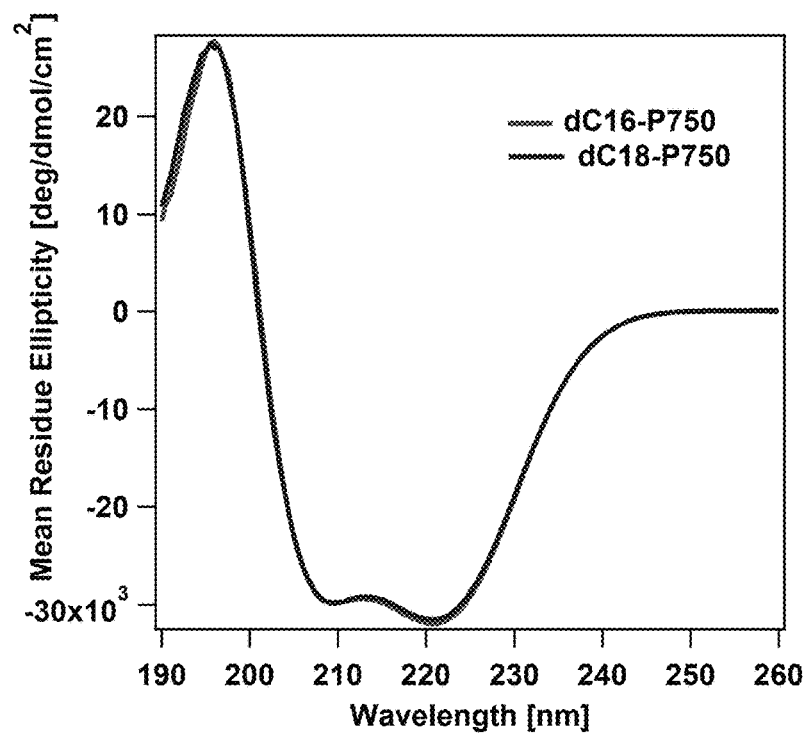
FIG. 5a shows the analysis of dC16-1coi(PEG2K)-PEG750 and dC18-1coi(PEG2K)-PEG750 micelles by circular dichroism.
Figure 5B:
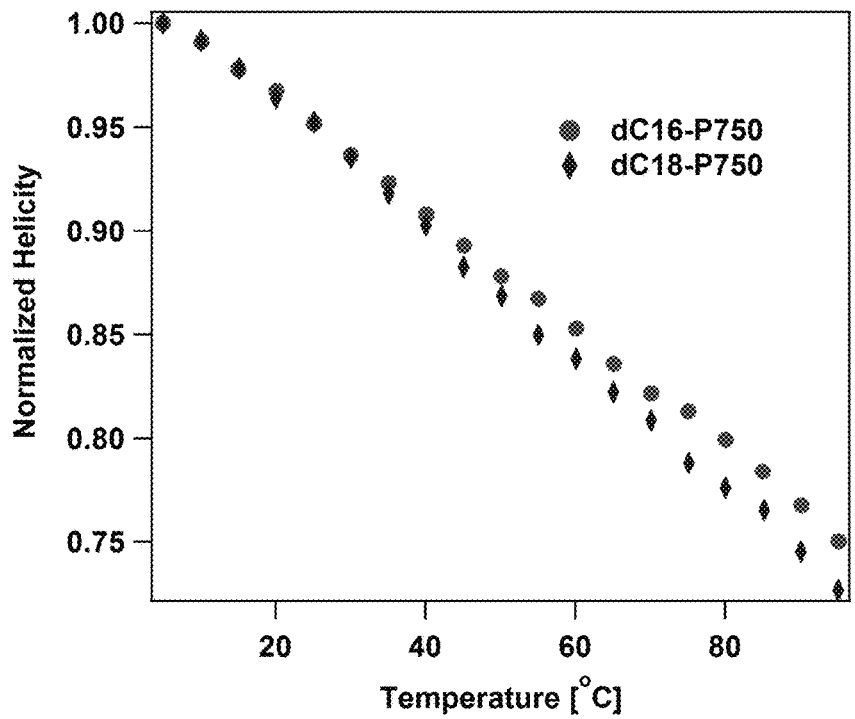
FIG. 5b shows the peptide helicity of dC16-1coi(PEG2K)-PEG750 and dC18-1coi(PEG2K)-PEG750 micelles recorded over a range of temperatures.
Figure 6A:
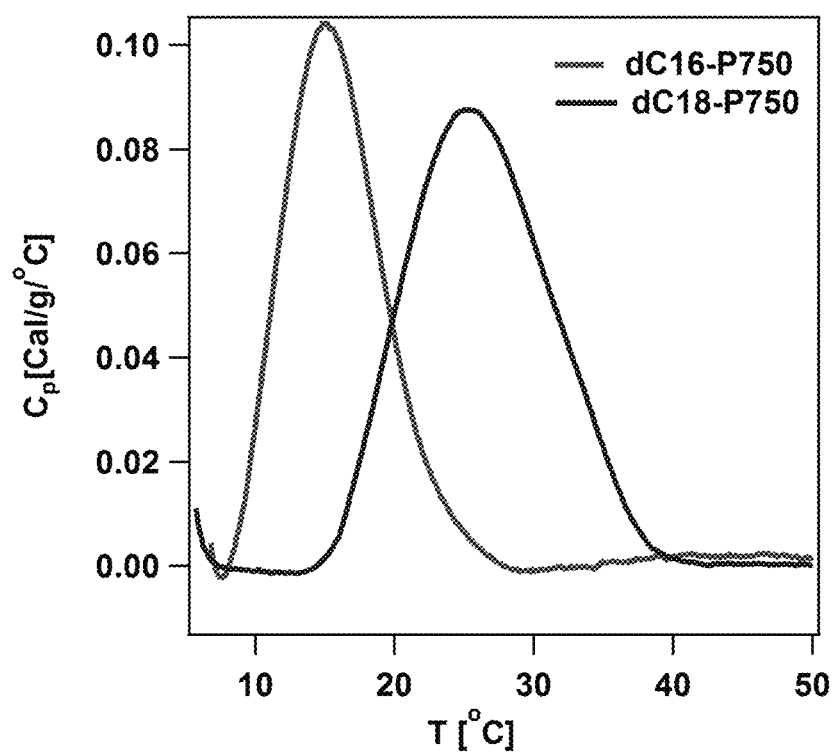
FIG. 6a shows the analysis of dC16-1coi(PEG2K)-PEG750 and dC18-1coi(PEG2K)-PEG750 micelles by differential scanning calorimetry.
Figure 6B:
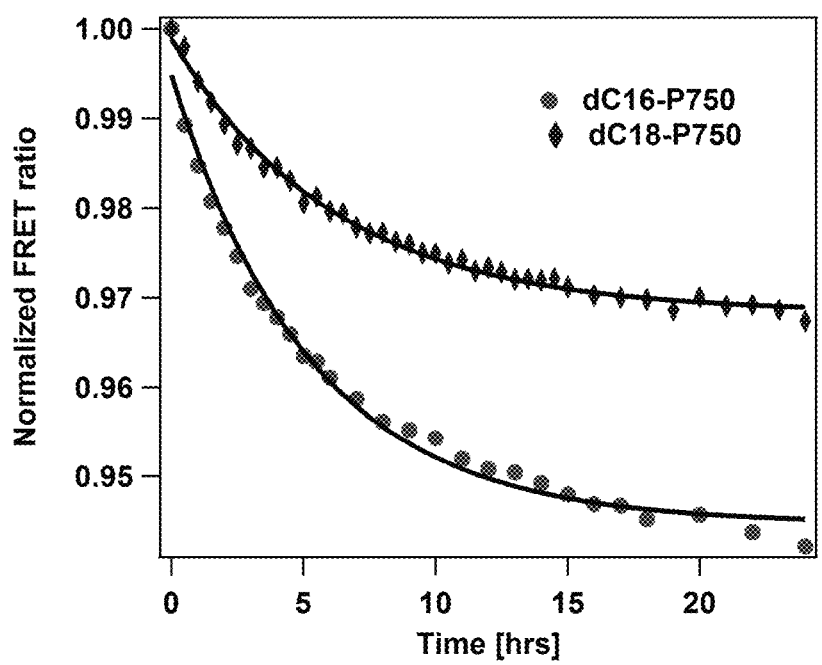
FIG. 6b shows the stability of dC16-1coi(PEG2K)-PEG750 and dC18-1coi(PEG2K)-PEG750 micelles, as assessed by FRET.

After initial equilibration in BSA (~10 min), a major emission peak is observed at 565 nm, which is accompanied by a minor emission peak at 505 nm. This indicates that both dyes are encapsulated within individual micelles and arranged in close proximity. If the cargo molecules leach out, FRET turns "off" due to the increase in the intermolecular distance between DiO and DiI resulting in a simultaneous increase of fluorescence intensity at 505 nm and decrease at 565 nm. For dC18-1coi(PEG2K)-PEG750 micelles, over time the fluorescence intensity remained essentially unchanged at both 505 nm and 565 nm (FIG. 4a). In contrast, for DSPE-PEG2K micelles, the intensity at 565 nm dropped significantly, which is accompanied by an increase in fluorescence intensity at 505 nm (FIG. 4b). The FRET ratio of $I_{565}/(I_{565}+I_{505})$ represents the efficiency of energy transfer and reflects the relative stability of micelles under the experimental conditions (FIG. 4c). A sharp decrease of the normalized FRET ratio was observed for DSPE-PEG2K micelles (FIG. 4c, bottom trace), indicating rapid cargo release out of micelles in BSA solution, whereas the ratio remained essentially constant for 3-helix micelles under the same conditions (FIG. 4c, top trace). This result is consistent with previously reported results indicating that DSPE-PEG2K micelles have poor stability in BSA with a half-life of 20 min at 37° C.

dC18-1coi(PEG2K)-PEG750 micelles were compared with dC16-1coi(PEG2K)-PEG750 micelles have a C16 alkyl core. As shown by the circular dichroism measurements in FIG. 5, peptide helicity and coiled coil structure were maintained for conjugates with alkyl tails of different hydrophobicity. The temperature stability of the peptide structure was not significantly different for the two alkyl tails. As shown by the DSC data in FIG. 6a, the phase transition temperature for alkyl chain packing increased with the hydrophobicity of the alkyl chain. Micelles with a more hydrophobic core demonstrated greater stability, as assessed by FRET (FIG. 6b).

Drug Loading.

Figure 7A:
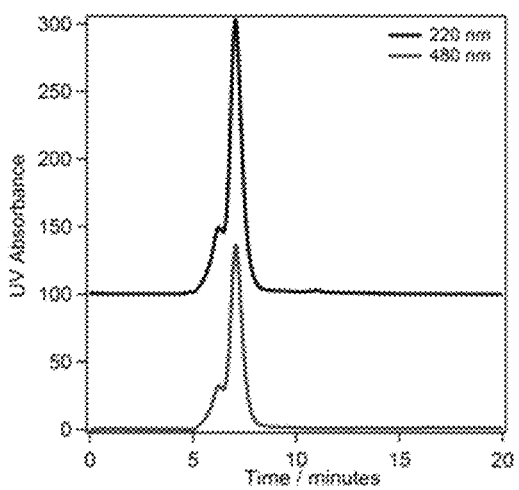
FIG. 7 shows the structural characterization and thermal stability measurements for DOX-loaded dC18-1coi (PEG2K)-PEG750 micelles via (a) size exclusion chromatography, (b) dynamic light scattering, and (c) fluorescence spectrometry.
Figure 7B:
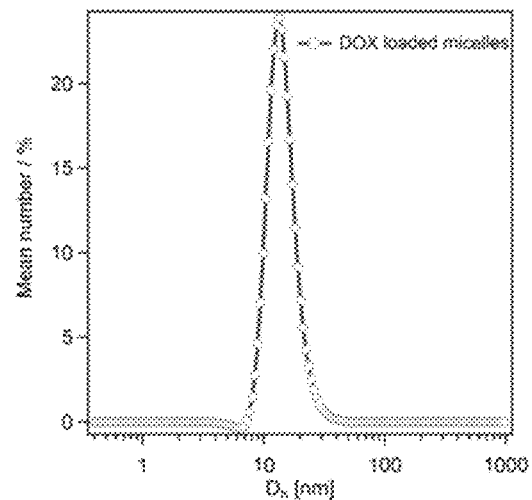
Figure 7C:
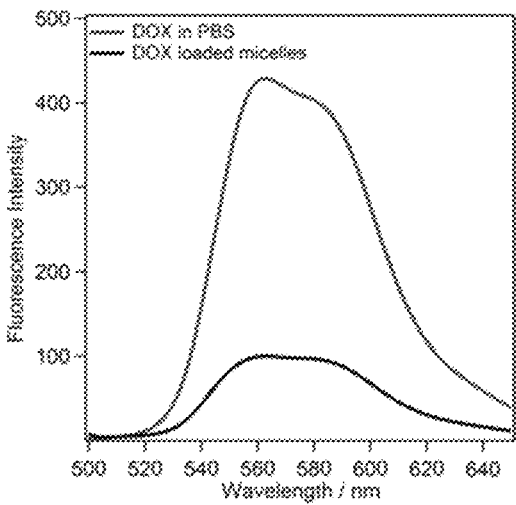

A range of drugs, with varying molecular structure and hydrophobicity, can be incorporated into the micelles of the invention. Dye molecules and other substances can be readily encapsulated in the micelles including dipyrrometheneboron difluoride (BODIPY) and lipophilic carbocyanines for fluorescence imaging. To evaluate the potential of the 3-helix micelles as nanocarriers for therapeutic applications, DOX was used to estimate the drug loading capacity. The encapsulation of DOX in the micelles was performed using a dry-down method. dC18-1coi(PEG2K)-PEG750 and DOX were first solubilized in methanol, dried and rehydrated. After spin dialysis to remove free drugs, size exclusion chromatography (SEC) and DLS were used to characterize the homogeneity of the DOX-loaded micelles. As shown in FIG. 7a, the overlapping elution profiles of the micelles monitored at 220 nm (top trace) and 480 nm (bottom trace) that monitor the peptide and DOX, respectively, verified the encapsulation of doxorubicin in the micelles and the absence of free drug. DLS experiments (FIG. 7b) indicate that the addition of DOX (8 wt % DOX loading) did not disrupt the uniformity of the micelles, showing a single species with a diameter of 15 nm. Quenching of DOX fluorescence in micelles (FIG. 7c, bottom trace), compared to free DOX in solution (FIG. 7c, top trace), further confirmed the presence of DOX in the micelles. The DOX loading was determined by dissolving the lyophilized powder in methanol and monitoring the absorbance of the DOX at 485 nm. For DOX, drug loading in the range of 7-8 wt % was obtained reproducibly. This is comparable to the values obtained by covalent conjugation of DOX to dendrimers and polypeptides, where 4-10 wt % has been reported. Loading of doxorubicin, rapamycin, and paclitaxel into the dC18-1coi(P2K)-P750 micelles is summarized in Table 1.

TABLE 1

Encapsulation of drugs in dC18-1coi(P2K)-P750 micelles.

| Drug | Loading (wt %) |
|---|---|
| Doxorubicin | 7.6 ± 0.4 |
| Rapamycin | 2.1 ± 0.6 |
| Paclitaxel | 1.9 ± 0.4 |

Figure 8A:
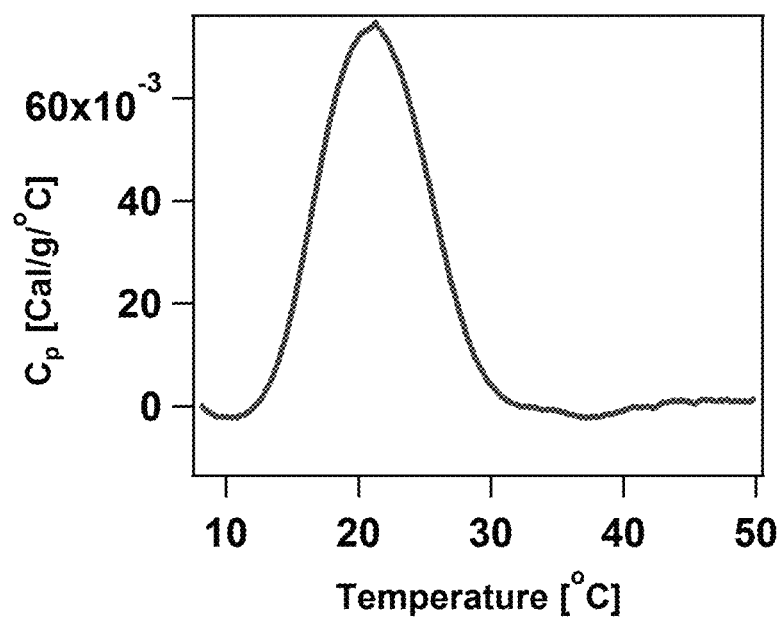
FIG. 8a shows the characterization of rapamycin-loaded dC18-1coi(PEG2K)-PEG750 micelles by differential scanning calorimetry.
Figure 8B:
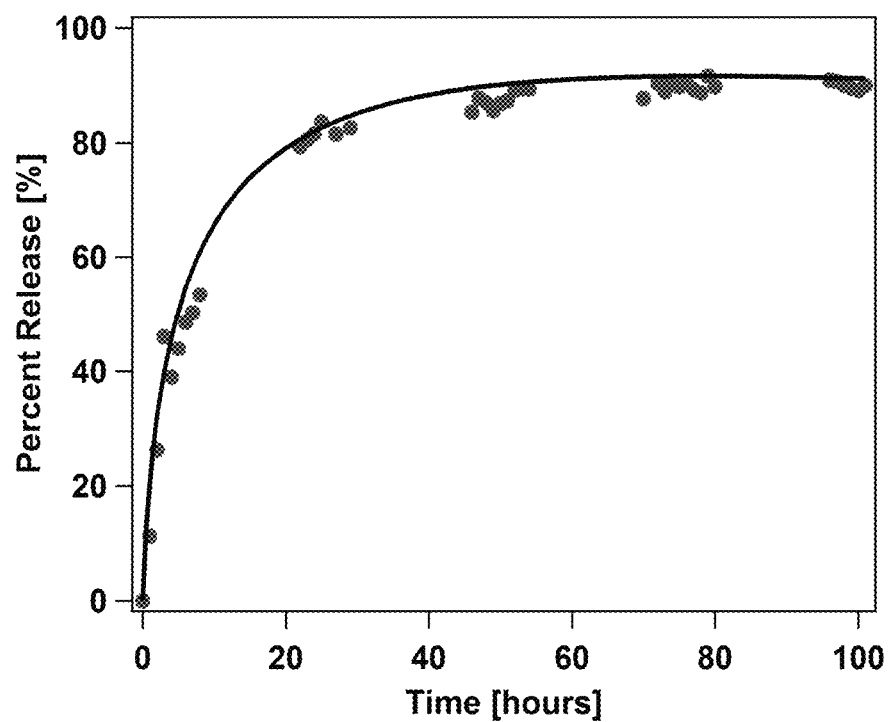
FIG. 8b shows the kinetics of rapamycin release from the loaded micelles.

As shown in FIG. 8a, rapamycin encapsulation resulted in a minimal effect on core packing in the micelles. 50% of the encapsulated drug was release within 8 hours, as shown in FIG. 8b.

Figure 9:
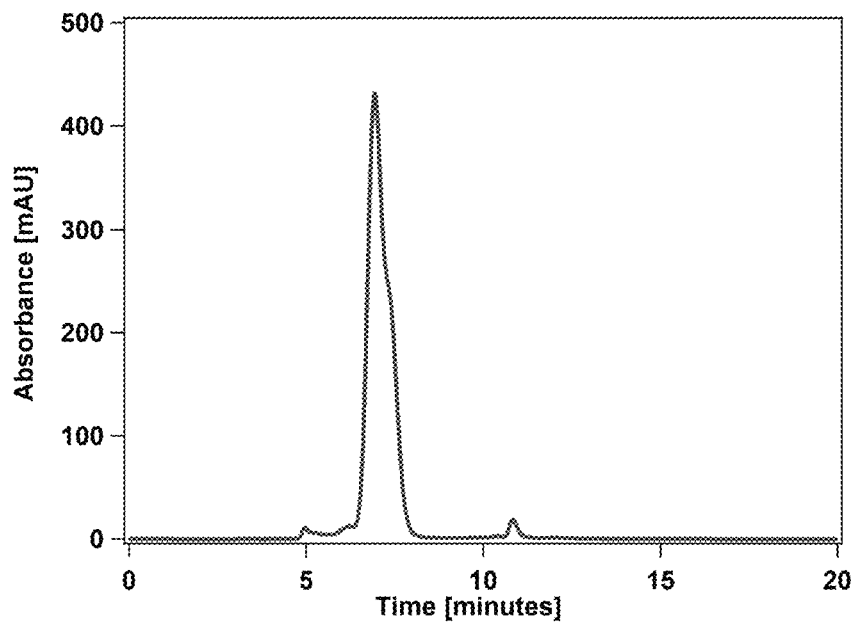
FIG. 9 shows the analysis of paclitaxel-loaded dC18-1coi (PEG2K)-PEG750 micelles by size exclusion chromatography (paclitaxel loading=1.5 wt %).
Figure 10:
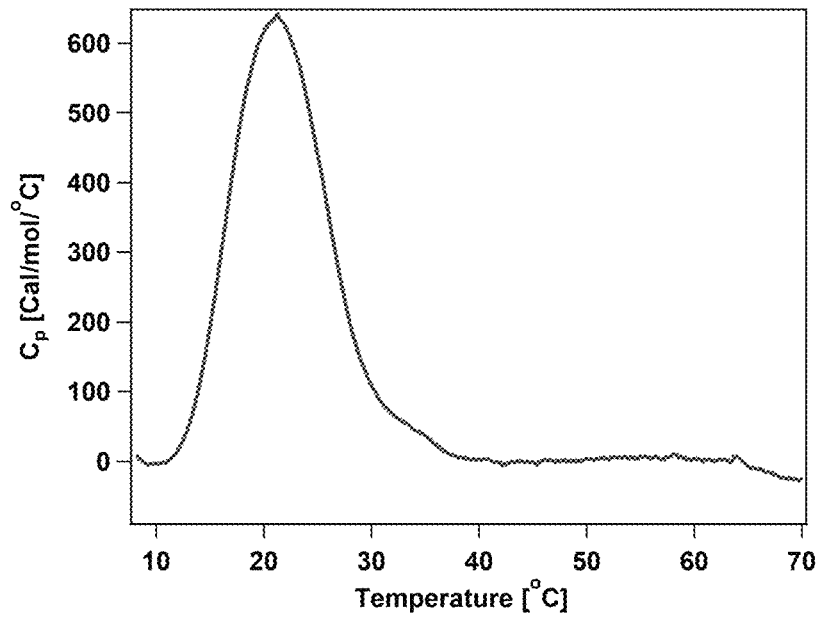
FIG. 10 shows the analysis of paclitaxel-loaded dC18-1coi(PEG2K)-PEG750 micelles by differential scanning calorimetry.

Size exclusion chromatography showed that paclitaxel loading did not prevent assembly of the peptide conjugates in to 3-helix bundles and micelles (FIG. 9). Differential scanning calorimetry showed that paclitaxel encapsulation resulted in a minimal effect on core packing in the micelles (FIG. 10).

Figure 11:
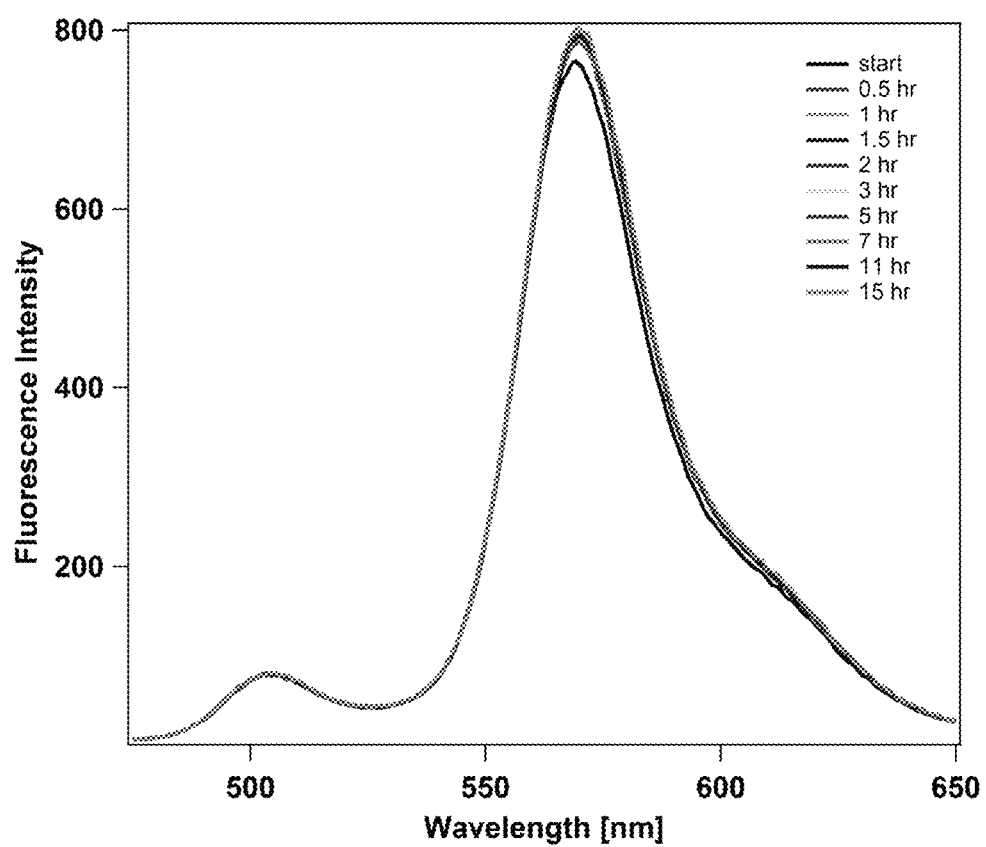
FIG. 11 shows the stability of paclitaxel-loaded dC18-1coi(PEG2K)-PEG750 micelles in 50 mg/mL BSA at 37° C. over time, as assessed by fluorescence spectroscopy.

FIG. 11 shows that the stability of the 3-helix micelles was not adversely affected and maintained after paclitaxel incorporation, as assessed by FRET.

Figure 12A:
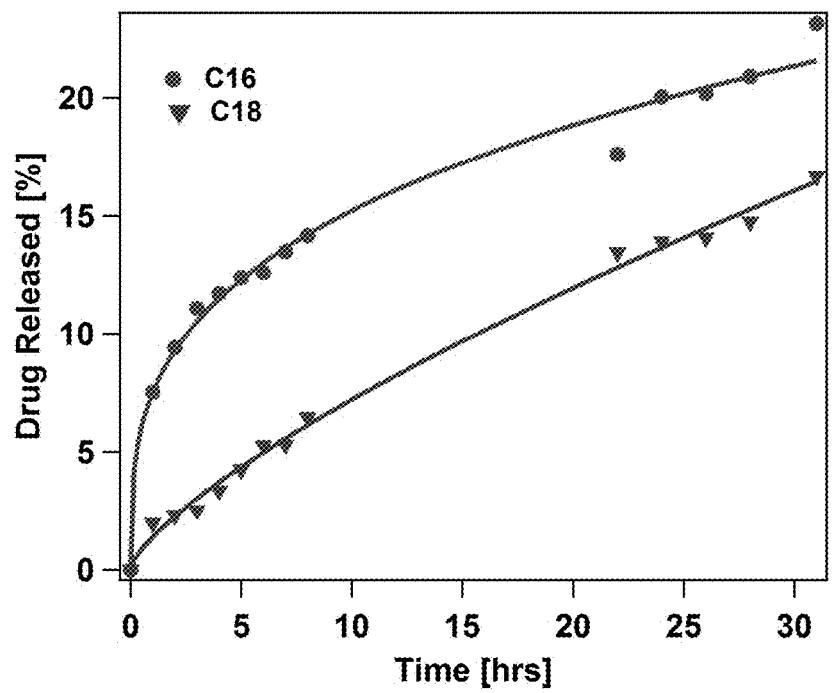
FIG. 12 shows drug release measurements for dC16-1coi (PEG2K)-PEG750 and dC18-1coi(PEG2K)-PEG750 micelles loaded with (a) doxorubicin and (b) rapamycin.
Figure 12B:
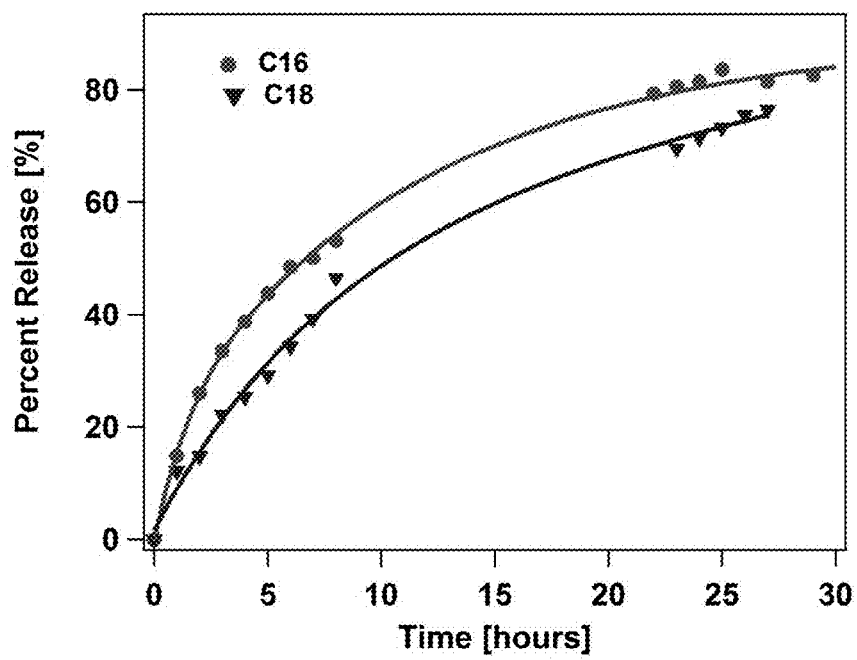

FIG. 12 shows that drug release is slower from more stability micelles (i.e., dC18-1coi(PEG2K)-PEG750) for two structurally different drugs, doxorubicin and rapamycin.

Example 3: In Vivo Characterization of Bis-Polymer Lipid-Peptide Conjugate Micelles Synthesis of 6-p-(4-(N-maleimidomethyl)cyclohexan-1-amido)benzyl 1,4,8,11-tetraazacyclotetradecane-N,N',N'',N''' tetraacetate (6-BAT-maleimide)

6-p-aminobenzyl 1,4,8,11-tetraazacyclotetradecane-N,N', N'',N''' tetraacetate (6-Aminobenzyl TETA, 25 mg) was reacted with sulfo-SMCC (25 mg, ProteoChem, Denver) in phosphate buffered saline (PBS 1×, 8 mL) and the pH was maintained at 7 for 2 hours with the addition of 1 M sodium hydroxide solution. The reaction mixture was diluted with 0.1% TFA solution (4 mL). 6-BAT maleimide was isolated with a reverse phase HPLC system (Jupiter Proteo C12, 250×10 mm) and elution was monitored at 220 and 254 nm wavelengths. The flow rate was 3 mL/min and a linear gradient was applied as 5 to 60% solvent B over 30 min (solvent A: 0.1% TFA DI water (v/v), solvent B: 0.1% TFA acetonitrile (v/v)).

Synthesis of 6-BAT-dC18-1coi(PEG2K)-PEG750

To introduce PEG2K, Fmoc-Lys(Alloc)-OH was used at the 15 position along the 1coi backbone. For a 50 μmol reaction, selective deprotection of the Alloc group was carried out in the presence of 12 mg Pd(PPh3)$_4$ catalyst and 150 μl radical trapping agent PhSiH$_3$ in DCM for 30 mins. The reaction was repeated five more times. Carboxyl terminated PEG2K was subsequently coupled on the side chain of the lysine residue using HBTU/DIPEA chemistry. The coupling reaction was performed at room temperature for 24 hours and repeated twice. After cleavage in TFA, the crude peptide was reacted with 6-BAT-maleimide in phosphate buffer (pH=7.4) with molar ratio of 1 to 4. Purification by reverse phase HPLC gave the final product in 30% yield.

Radiolabeling of dC18-1Coi(PEG2K)-PEG750 Micelles with Cu-64.

Mixed micelles were prepared by thin film hydration method. dC18-1coi(P2K)-P750 and 6-BAT-1coi-dC18-PEG2K in 98/2 wt/wt % were dissolved in methanol in a glass vial and the solvent was evaporated in vacuum oven for 3 hours. The dried film was rehydrated with 25 mM phosphate buffer, pH 7.4, and the solution was stirred for 16 hours to allow the assembly into mixed micelles. The phosphate salts were removed by spin ultrafiltration (Amicon centrifugal filter units, MW cutoff: 3000 Da). The concentrate obtained was washed with water and lyophilized to obtain mixed micelles.

A lyophilized dC18-1coi(PEG2K)-PEG750 and 6-BAT-dC18-1coi(PEG2K)-PEG750 powder (98/2, mol %/mol %, 3.7 mg) was dissolved in deionized water and aged overnight at room temperature. $^{64}CuCl_2$ (Isotrace, St. Louis, Mo.), buffered in 0.1 M ammonium citrate (pH 5.5, 100 mL), was added to a solution of micelles and incubated at 30° C. for 1.5 hours. To remove the non-specific binding of Cu-64, 0.1 M EDTA (10 μL) was added and the mixture was incubated for 10 min at room temperature. Size exclusion chromatography (Sephadex G-75, GE healthcare) demonstrated Cu-64 labeled micelles with more than 95% labeling yield in a 2 mL volume. Cu-64 micelles were concentrated by centrifugation (4000 g) for 30 minutes. The specific activity of the micelles at the end of synthesis was 140 GBq/mol.

Radiolabeling of Conventional Micelles (DSPE-PEG2K-OMe) with Cu-64.

DSPE-PEG2K-OMe and 6-BAT lipid (97/3, mol %/mol %, 2 mg) in chloroform were dried in a glass test tube under gentle nitrogen stream at 50° C. Dried lipids were lyophilized overnight. Warmed deionized water (0.5 mL) was added to the test tube, which was gently shaken until the solution became clear. $^{64}CuCl_2$ (2.51 mCi), buffered in 0.1 M ammonium citrate (pH 5.5, 100 mL), was added to a solution of micelles and incubated at 30° C. for 1 hour. Labeled conventional micelles were separated with size exclusion chromatography (Sephadex G-75, GE healthcare). The labeling yield was 95% and the specific activity of the micelles at the end of the synthesis was 124 GBq/mol.

Animal Protocol (NDL Tumor Mouse Model).

All animal experiments were conducted under a protocol approved by the University of California, Davis, Animal Care and Use Committee (Davis, Calif.). Four 4-week old female FVB mice weighing 19-22 g (Charles River, Wilmington, Mass.) were housed in a temperature controlled room in ventilated cages. All animals were maintained on a 12 hour light cycle and were provided standard rodent chow and water ad libitum. To generate NDL tumors by tumor cell injection, the recipient mice were anesthetized by an IP injection of a ketamine (100 mg/kg)/xylazine (10 mg/kg) solution. The #4 inguinal fat pads were then bluntly dissected and exposed. A solution of 1×106 NDL tumor cells suspended in 20 μl PBS was injected directly into the left and right 4th inguinal mammary fat pads of the recipient mice using a 29 gauge needle. The incision sites were then closed with 1 wound clip per side, and a one-time injection of Buprenex was given for pain management at 0.05-0.1 mg/kg subcutaneously before the animal was ambulatory. The wounds were monitored for 7 days until the wound clips were removed. The tumor was allowed to grow for 12 days before reaching a size of approximately 5 mm on the first day of the study.

MicroPET Imaging and Biodistribution Analyses.

After the injection of $^{64}$Cu-dC18-1coi(PEG2K)-PEG750 micelles, female FVB mice (n=6) bearing NDL tumors bilaterally within the mammary fat pads were imaged with microPET and the biodistribution assessed. In vivo PET scans were obtained for 30 minutes immediately after tail vein injection of $^{64}$Cu-dC18-1coi(PEG2K)-PEG750 micelles (316±83 μCi and 86±24 nmol lipid per mouse) in 150 μL PBS and for 30 min at 3, 6, 24, and 48 h after injection. Animals anesthetized with 2% to 3% isoflurane were placed in pairs on the scanner bed and PET acquisitions were obtained using a small-animal PET scanner (Focus120, Siemens Medical Solutions, Inc.). After final time point scanning of each set of animals, animals were euthanized by cervical dislocation and blood was withdrawn by cardiac puncture. Briefly, once the animals were euthanized organs were harvested for biodistribution and the radioactivity measured in a γ-counter (Perkin-Elmer Life Sciences). For the biodistribution of Cu-64 labeled conventional micelles, two female Balb/c mice weighing 26-27 g (Charles River, Mass.) were used. Cu-64 labeled conventional micelles (7.33±0.07 MBq and 69±1 nmol lipids per mouse) were administered via the tail vein, the animals were sacrificed at 24 hours after injection due to the rapid clearance of the radioactivity, and the procedures above followed for biodistribution.

Results and Discussion: In Vivo Studies of 3-Helix Micelles Using PET Imaging.

Figure 13A:
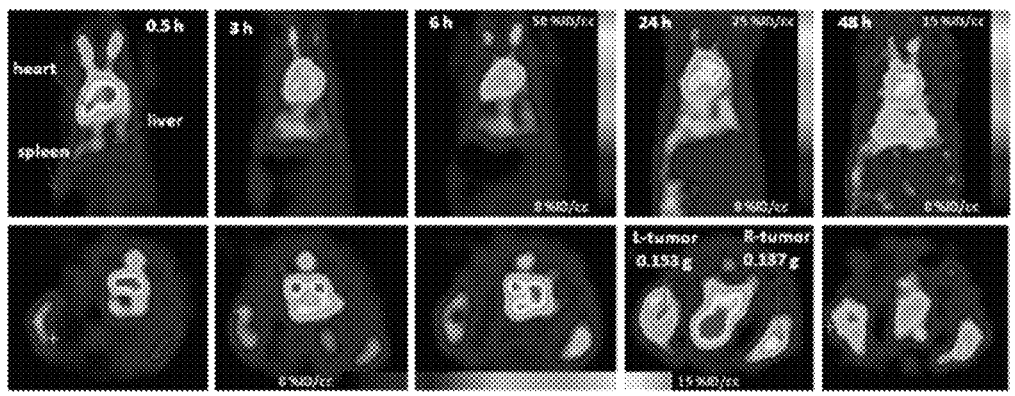
FIG. 13 shows (a) the in vivo assessment of $^{64}$Cu-dC18-1coi(PEG2K)-PEG750 micelle circulation and stability using positron emission tomography (PET), (b) the blood radioactivity profile over time following micelle administration, and (c) the radioactivity distribution in plasma and blood cells.
Figure 13B:
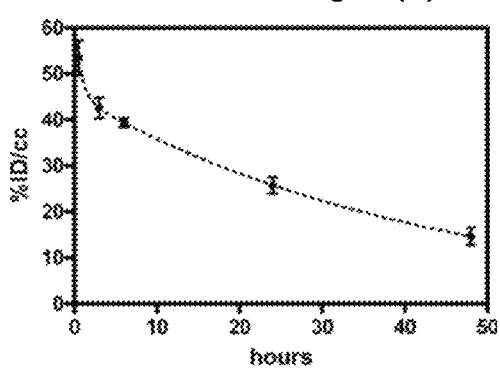
Figure 13C:
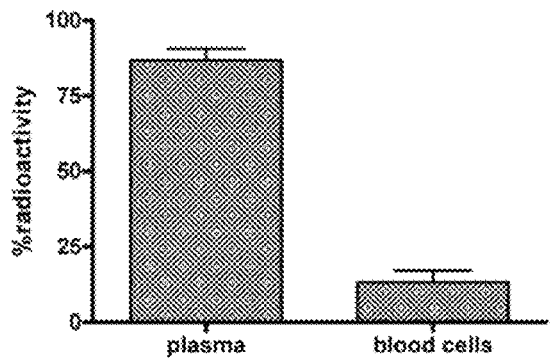

Pharmacokinetic evaluation and biodistribution of the 3-helix micelles were carried out to validate their potential as nanocarriers. The preparation of $^{64}$Cu labeled 3-helix micelles was achieved by co-assembly of metal-chelator functionalized amphiphilic peptides with the regular amphiphiles followed by high affinity coordination reaction with $^{64}$Cu ions. Micelle solutions were administered through intravenous injection to mice bearing NDL tumors. Using positron emission tomography (PET), the pharmacokinetics of radiolabeled micelles were assessed and compared with long circulating liposomes and conventional DSPE-PEG2K micelles. All tested micelles have similar degrees of hydrophobicity, as they are composed of double C18 tails and a PEG layer to prevent non-specific protein adsorption. FIG. 13a shows coronal (top) and transverse (bottom) view of sliced PET images of $^{64}$Cu-dC18-1coi(PEG2K)-PEG750 micelles administered mouse. Images were acquired after the reconstruction of histograms with maximum a posteriori probability (MAP) estimate. PET images were acquired over 48 hours after injection and demonstrated that the 3-helix micelles remained highly concentrated in the blood pool, with minimal liver and spleen accumulation. FIG. 13b shows the blood radioactivity (% ID/cc) of $^{64}$Cu-dC18-1coi (PEG2K)-PEG750 micelles. The data curve was fitted as a two phase exponential decay (Y=45.32$e^{-0.0235 \times t}$+ 16.42$e^{-1.27 \times t}$, $t_{1/2}\alpha$=0.55, β=29.52). Approximately 15±1.5% ID/g remained circulating in the blood pool even at 48 hours post injection. Based on the image data set, the pharmacokinetic of 3-helix micelle was fitted using a bi-phase model. The β-phase blood circulation half-life ($t_{1/2,\beta}$) of the micelles was estimated to be ~29.5 hours (FIG. 13b), which is comparable to that of successful dendrimers. FIG. 13c shows the calculated % radioactivity in plasma and blood cells, 48 hours after injection. % Radioactivity was calculated as: [100×plasma radioactivity/(plasma radioactivity+blood cells radioactivity)]. The analysis shows that the activity was confined to plasma rather than the circulating cellular components.

Figure 25A:
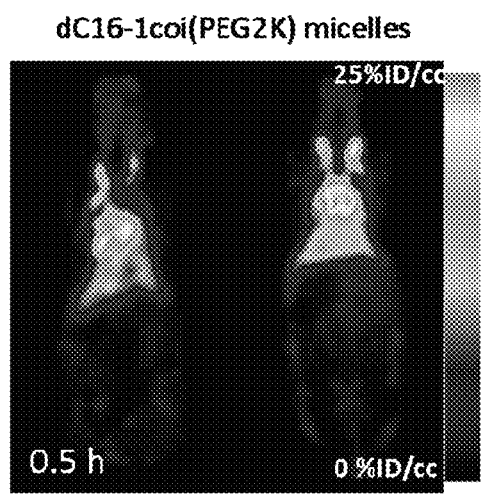
FIG. 25 shows the PET analysis of in vivo micelle localization for (a)$^{64}$Cu-dC18-1coi(PEG2K) micelles 30 minutes after administration, (b)$^{64}$Cu-dC18-1coi(PEG2K) micelles 24 hours after administration, (c)$^{64}$Cu-dC18-1coi(PEG2K)-PEG750 micelles 30 minutes after administration, and (d)$^{64}$Cu-dC18-1coi(PEG2K)-PEG750 micelles 24 hours after administration.
Figure 25C:
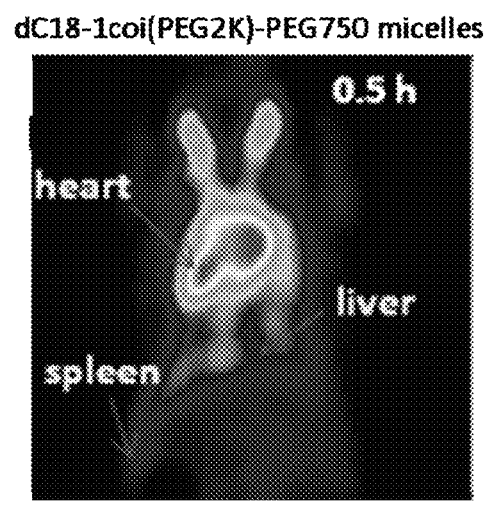
Figure 25B:
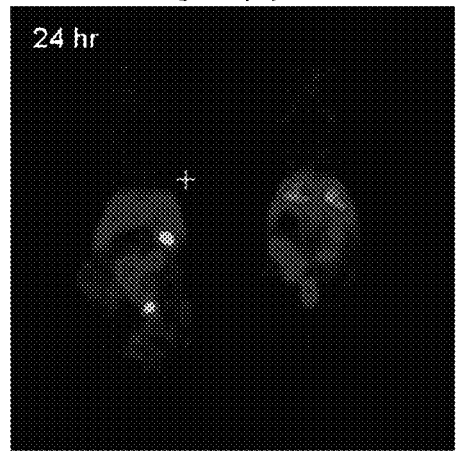
Figure 25D:
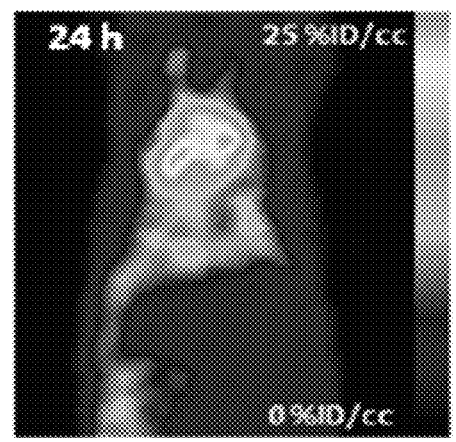
Figure 26:
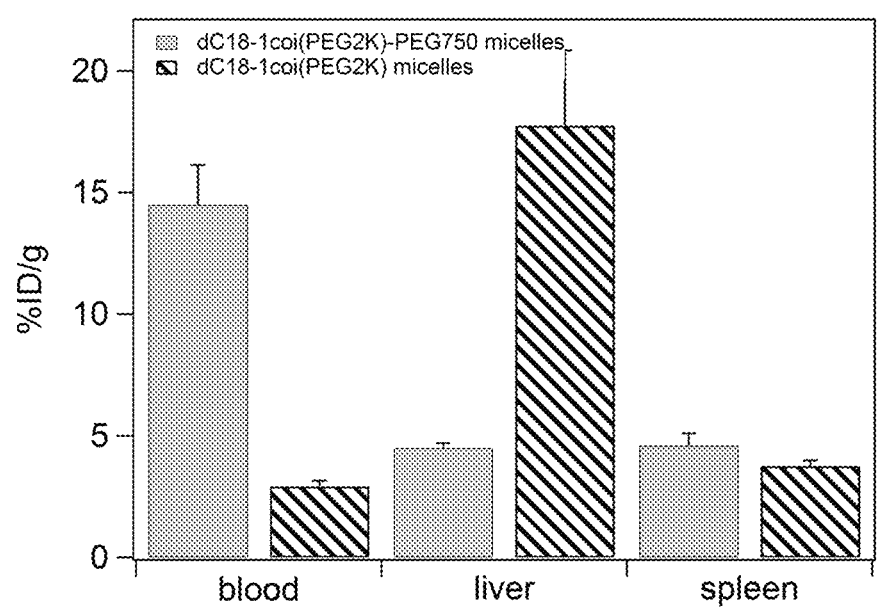
FIG. 26 shows a comparison of radioactivity (% ID/g) of $^{64}$Cu-dC18-1coi(PEG2K)-PEG750 micelles and $^{64}$Cu-dC18-1coi(PEG2K) micelles in blood, liver, and spleen at 48 hr post injection.
Figure 27A:
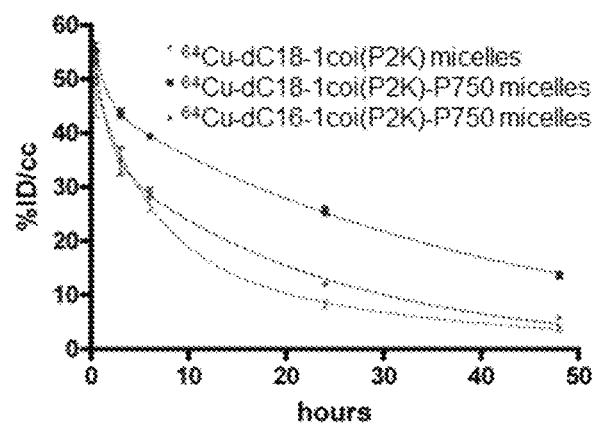
FIG. 27A shows higher concentrations for $^{64}$Cu-dC18-1coi(PEG2K)-PEG750 micelles.
Figure 27B:
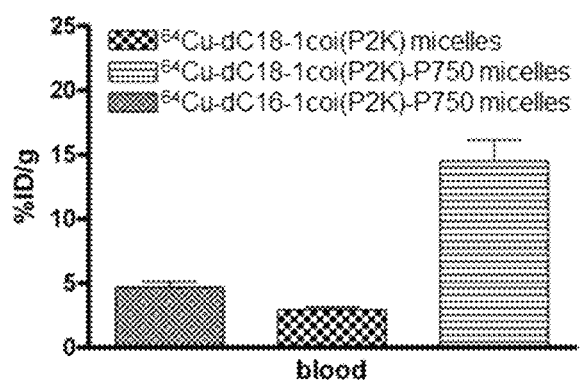
FIG. 27B shows relative blood concentrations with $^{64}$Cu-dC18-1coi(PEG2K)-PEG750 micelles having higher blood concentrations.

The $^{64}$Cu-dC18-1coi(PEG2K)-PEG750 micelles exhibit improved characteristics as compared to micelles composed of mono-PEG conjugates (i.e. $^{64}$Cu-dC18-1coi(PEG2K) without C-terminal PEG750). The PET images in FIG. 25 show that the level of $^{64}$Cu-dC18-1coi(PEG2K)-PEG750 micelles circulating in the subject at 24 hr after administration (FIG. 25d) is significantly higher than the level of $^{64}$Cu-dC18-1coi(PEG2K) micelles at 24 hr after administration (FIG. 25b). This is also reflected in the comparison of radioactivity of $^{64}$Cu-dC18-1coi(PEG2K)-PEG750 micelles and $^{64}$Cu-dC18-1coi(PEG2K) micelles in blood, liver, and spleen at 48 hr post injection (FIG. 26). Attaching PEG750 at the C-terminus significantly increased the blood circulation lifetime (14.5% ID/g for PEGylated micelles vs. 2.9% ID/g for non-PEGylated micelles) and reduced the accumulation in the reticuloendothelial system organs, such as liver and spleen. As shown in FIG. 27, micelles with a C18 core demonstrated higher stability and longer blood circulation times than micelles with a C16 core.

Figure 14A:
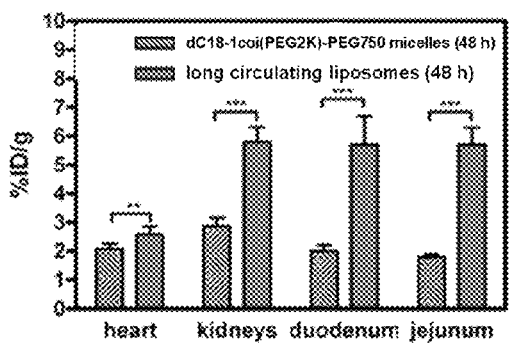
FIG. 14(a) shows the biodistribution of $^{64}$Cu-dC18-1coi (PEG2K)-PEG750 micelles as compared to long-circulating liposomes.

FIG. 14 shows the comparison of the biodistribution profile of the 3-helix micelles (n=6) with long circulating liposomes (n=4) and conventional DSPE-PEG2K-OMe micelles (n=2) in non-perfused mice. The radioactivity resulting from injection of 3-helix micelles is the highest in the blood pool with 15.0±1.5% ID/g. The uptake of the 3-helix micelles in NDL model tumors (5.7±0.9% ID/g) was similar to that achieved with $^{64}$Cu-liposomes (4.3% ID/g) and $^{64}$Cu-albumin in a similar model (MIN-0). It is believed that the uptake can be attributed to the EPR effect. The radioactivities of different organs were observed as following: 4.6±0.5% ID/g in the spleen, 4.5±0.2% ID/g in the liver, 2.9±0.3% ID/g in the kidney, 2.1±0.2% ID/g in the heart. The animals were not perfused in the study. Considering the high activity remained in blood at the point of the biodistribution study, the residual blood in liver and spleen may partially account for the activities observed in these organs. To further clarify the systemic clearance pathway, radioactivities in the duodenum and jejunum were measured, which are ~2% ID/g (FIG. 14a). Radioactivity (% ID/g) for $^{64}$Cu-dC18-1coi(PEG2K)-PEG750 micelles at 48 hours was compared with radioactivity for long circulating liposomes (liposomal 48 h data was obtained from a previous study). The low activity in digestion system, liver and spleen indicated that the reticuloendothelial systems (RES) clearance may not be the primary clearance pathway for the 3-helix micelles.

Figure 14B:
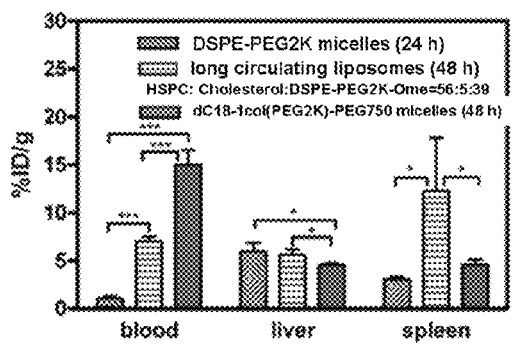
FIG. 14(b) shows the biodistribution of $^{64}$Cu-dC18-1coi(PEG2K)-PEG750 micelles as compared to long-circulating liposomes and conventional DSPE-PEG2K micelles.

The radioactivity detected within the blood, liver and spleen was also compared among the 3-helix micelles, DSPE-PEG2K-OMe micelles and long circulating liposomes (FIG. 14b). Due to the rapid clearance of DSPE-PEG2K-OMe micelles, biodistribution results at 24 hours were used for comparison to those obtained at 48 hours with long circulating liposomes and 3-helix micelles. The radioactivity in the liver resulting from DPSE-PEG2K-OMe micelles remained at a similar level to that of long circulating liposomes. Substantial differences between 3-helix micelles and long circulating liposomes were apparent: blood circulation was extended and liver and spleen accumulation was decreased compared with either previous strategy. Statistical analysis between groups was performed with one-way ANOVA followed by Tukey's multiple comparison test (in FIG. 14, *P<0.0001, P<0.001, *P<0.05).

In vivo pharmacokinetics and biodistribution studies clearly demonstrated that 3-helix micelles achieved long circulation half-life and efficient clearance. Reduced accumulation in the liver, spleen and intestine, combined with urinary activity suggest that the 3-helix micelle was not primarily cleared through the RES pathway. One hypothesis for the systemic clearance of 3-helix micelles is first by monomer desorption, where individual or trimeric amphiphiles exit the micelle during blood circulation. If the hydrophobic C18 tails cannot be shielded by the headgroup, the amphiphiles will be captured by serum proteins and subsequently cleared by the RES system, similar to results of other micelles, including DSPE-PEG2K and block copolymer based micelles. As the hydrophilic headgroup, i.e. 1coi-PEG2K, is over 5 kDa in molecular weight, it is possible that 1coi-PEG2K may wrap the C18 chains to shield non-favorable interactions between C18 and water. This is similar to our recent studies in 1coi-polystyrene conjugates where the 1coi unfolded and act as a surfactant for the hydrophobic PS. The molecular weight of dC18-1coi (PEG2K)-PEG750 amphiphile is only ~6 kDa, well below the critical molecular weight cutoff to pass through the glomerular membranes. In the sequence of the 1coi peptide, there are a few sites that can be cleaved by proteases. As an alternative to physical desorption of micelles, the 3-helix micelles can be internalized into cells and digested via proteolysis. Once the peptide is enzymatically degraded, the micelle will disassemble and the fragments of the amphiphile will be metabolized.

Example 4: Further Characterization of Conjugates and Micelles

Figure 15:
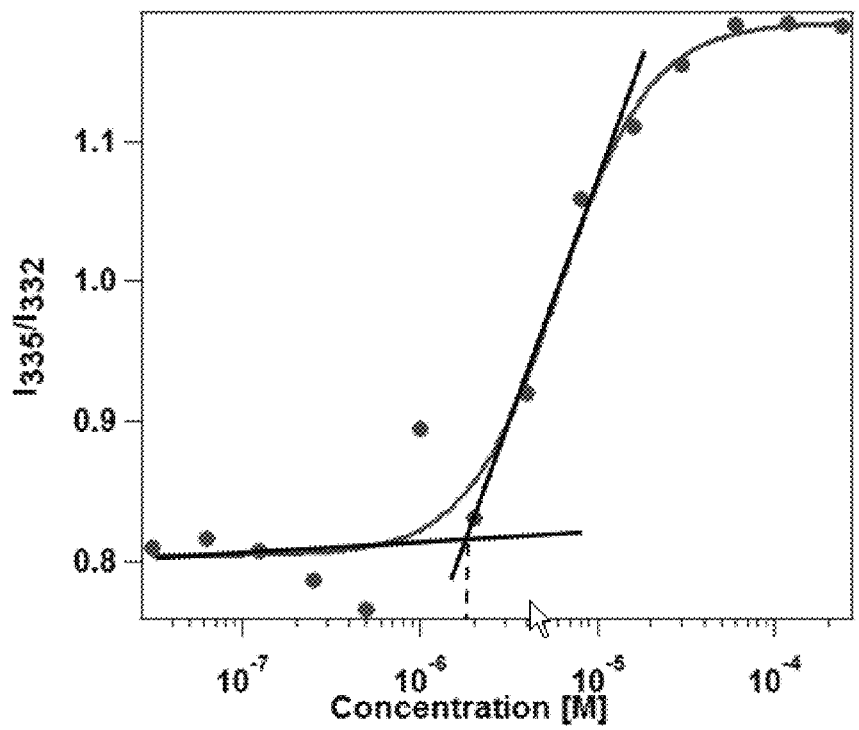
FIG. 15 shows pyrene fluorescence monitored as function of concentration of dC18-1coi(PEG2K)-PEG750 dissolved in 25 mM phosphate buffer, pH 7.4.

Pyrene fluorescence was monitored as function of concentration of dC18-1coi(PEG2K)-PEG750 dissolved in 25 mM phosphate buffer, pH 7.4 (FIG. 15). The concentration of pyrene was kept constant at $4 \times 10^{-7}$ µM. With increasing concentration of the amphiphile, pyrene started to partition in the core of the micelles. The concentration at which the slope of the curve started to increase indicated the critical micellar concentration (CMC). The CMC of dC18-1coi (PEG2K)-PEG750 is ~2 µM.

Figure 16:
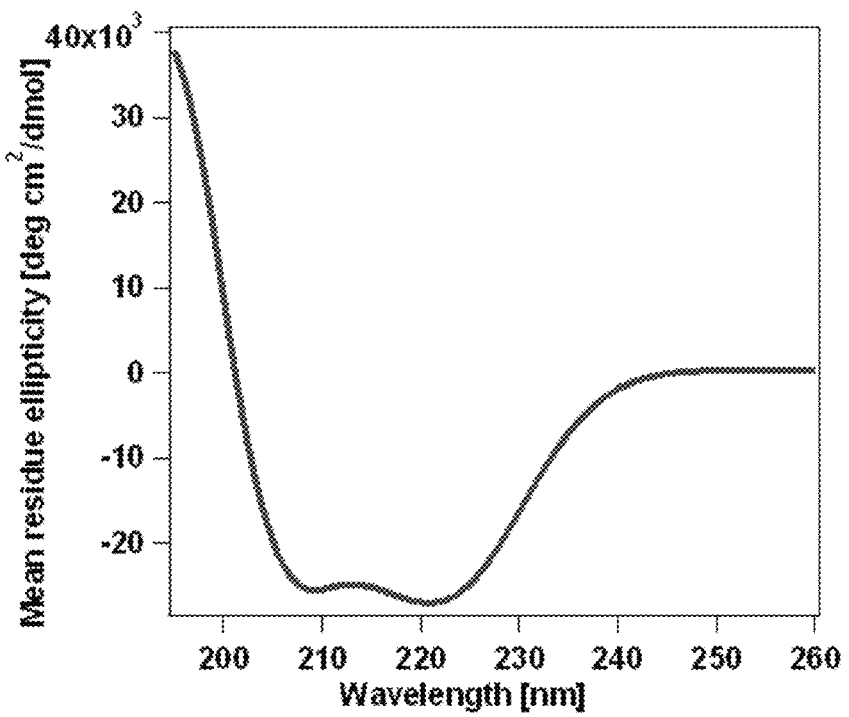
FIG. 16 shows the circular dichroism spectrum of 60 μM dC18-1coi(PEG2K)-PEG750 dissolved in 25 mM phosphate buffer, pH 7.4.

The CD spectrum of 60 µM dC18-1coi(PEG2K)-PEG750 dissolved in 25 mM phosphate buffer, pH 7.4, was recorded. The helicity of the peptide was ~74%. The ellipticity ratio at 222 nm and 208 nm was ~1.06, indicating that peptide in the shell of the micelle is structured as a coiled-coil helix bundle (FIG. 16).

Figure 17:
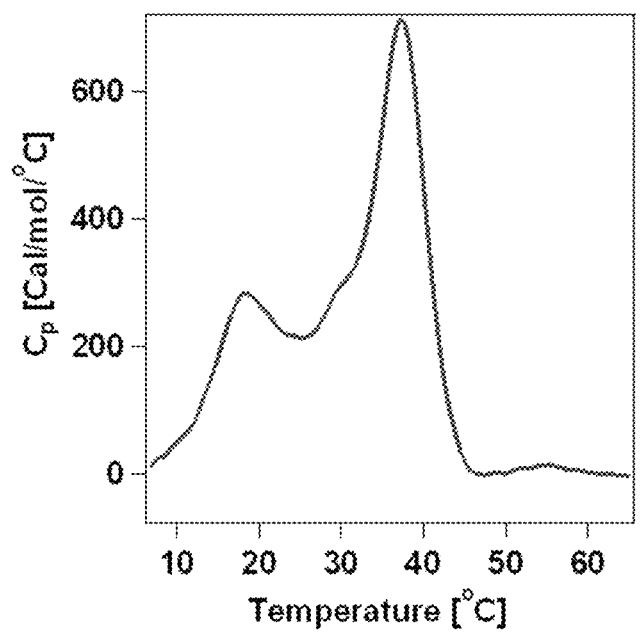
FIG. 17 shows the differential scanning calorimetry thermogram of 200 μM dC18-1coi(PEG2K)-PEG750 dissolved in 25 mM phosphate buffer, pH 7.4.

The differential scanning calorimetry thermogram of 200 µM dC18-1coi(PEG2K)-PEG750 dissolved in 25 mM phosphate buffer, pH 7.4, was recorded (FIG. 17). The peaks observed in the trace indicate heterogeneous lipid packing in the core of the micelles. The phase transition temperature of the alkyl chains in the lipid core corresponding to the predominant peak was ~37° C.

Figure 18:
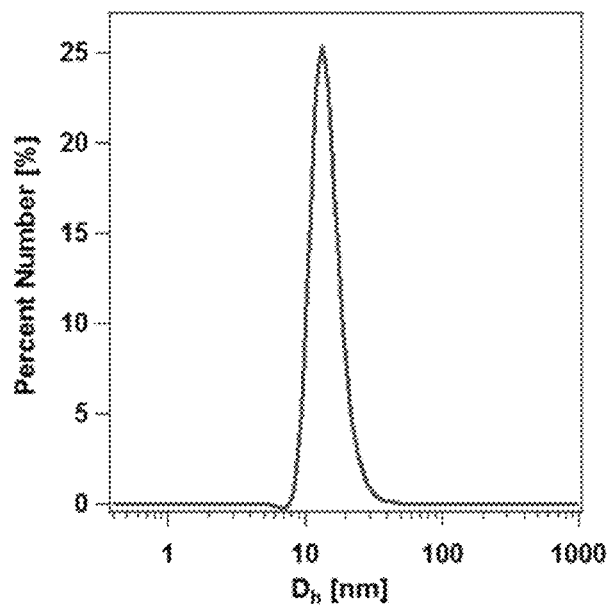
FIG. 18 shows dynamic light scattering trace of 60 μM dC18-1coi(PEG2K)-PEG750 dissolved in 25 mM phosphate buffer, pH 7.4.

The dynamic light scattering trace of 60 µM dC18-1coi (PEG2K)-PEG750 dissolved in 25 mM phosphate buffer, pH 7.4, was recorded. The hydrodynamic diameter of the micelles was ~16 nm (FIG. 18).

Figure 19:
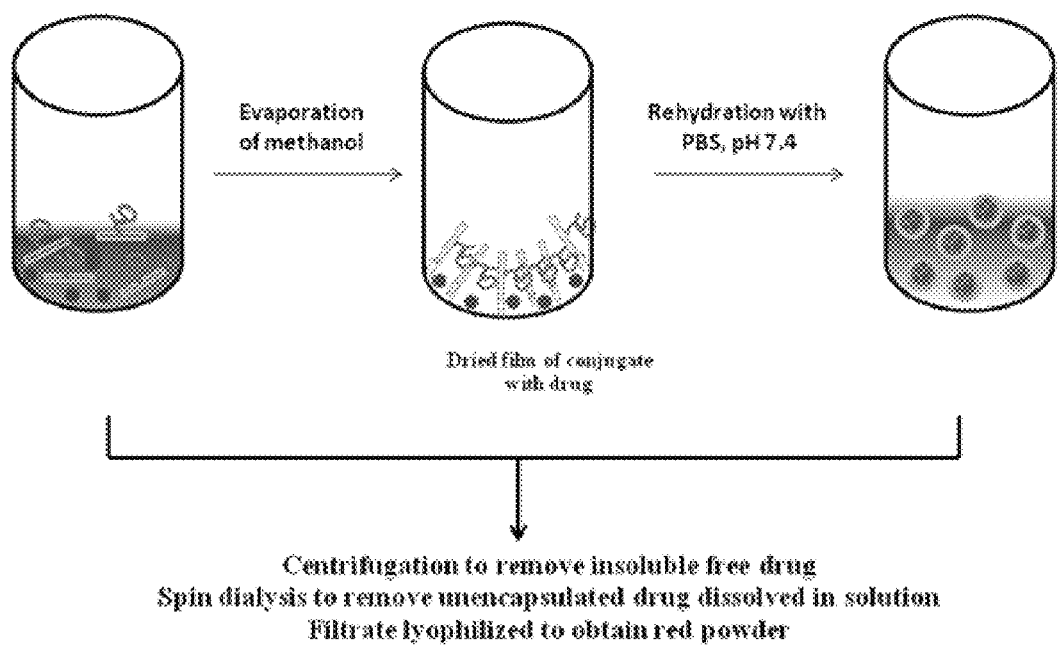
FIG. 19 shows the procedure used for loading of conjugate micelles with drug cargo.
Figure 20:
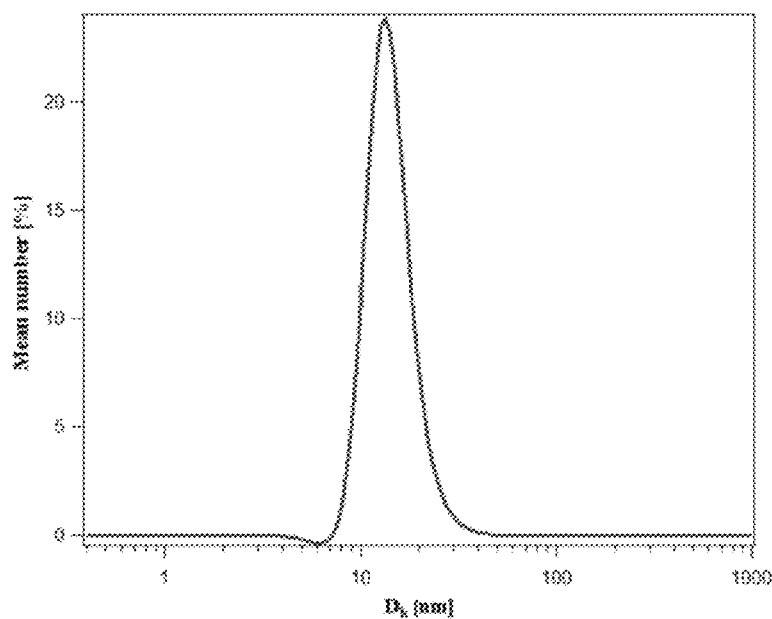
FIG. 20 shows the dynamic light scattering trace of doxorubicin loaded dC18-1coi(PEG2K)-PEG750 dissolved in 25 mM phosphate buffer, pH 7.4.

Micelles were loaded with doxorubicin according to the procedure outlined in FIG. 19. The dynamic light scattering trace of doxorubicin loaded dC18-1coi(PEG2K)-PEG750 dissolved in 25 mM phosphate buffer, pH 7.4, was recorded (FIG. 20). The loading was ~8 wt % doxorubicin.

Figure 21:
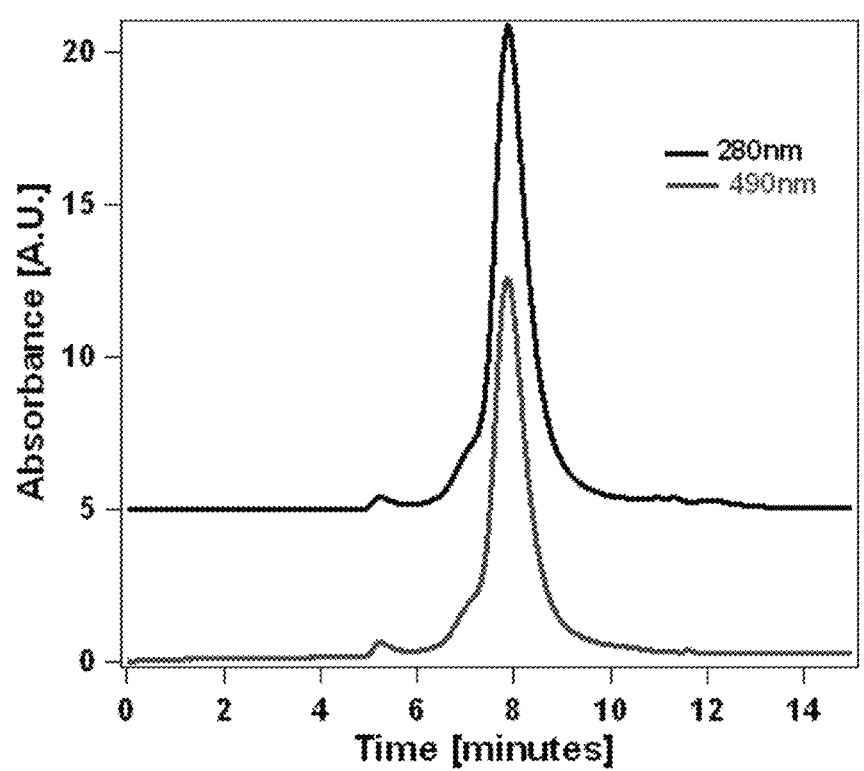
FIG. 21 shows the size exclusion chromatogram of doxorubicin loaded dC18-1coi(PEG2K)-PEG750 micelles dissolved in 25 mM phosphate buffer, pH 7.4.

The size exclusion chromatogram of doxorubicin loaded dC18-1coi(PEG2K)-PEG750 micelles dissolved in 25 mM phosphate buffer, pH 7.4, was recorded (FIG. 21). The overlapping elution profiles at 280 nm (peptide; top trace) and 490 nm (DOX; bottom trace) indicate the association of the particle with the drug with minimal free drug and particle aggregation.

Figure 22:
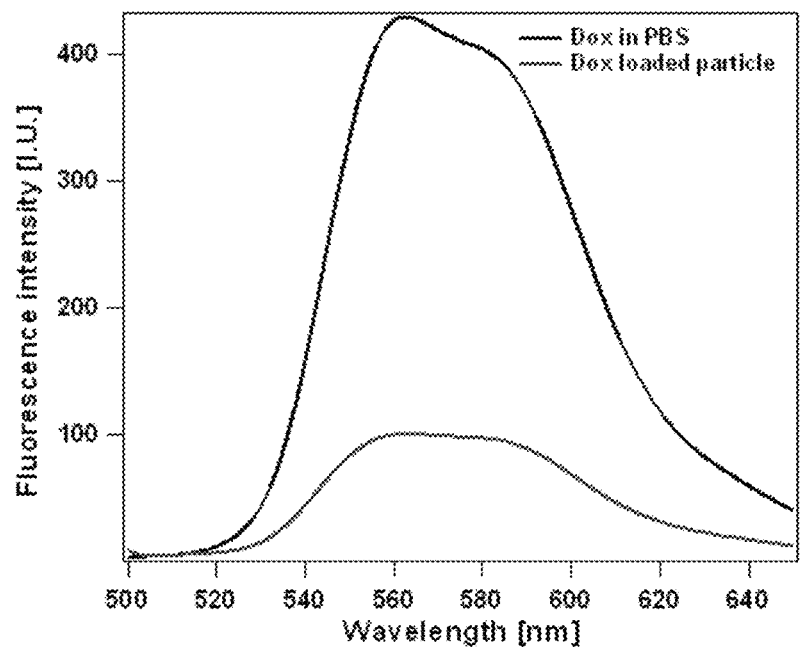
FIG. 22 shows the fluorescence spectrum of doxorubicin loaded dC18-1coi(PEG2K)-PEG750 micelles dissolved in 25 mM phosphate buffer, pH 7.4.

The fluorescence spectrum of doxorubicin loaded dC18-1coi(PEG2K)-PEG750 micelles dissolved in 25 mM phosphate buffer, pH 7.4, was recorded (FIG. 22). Quenching of doxorubicin fluorescence in the micelles (bottom trace) relative to free drug (top trace) indicates presence of drug in the micelle core.

Figure 23:
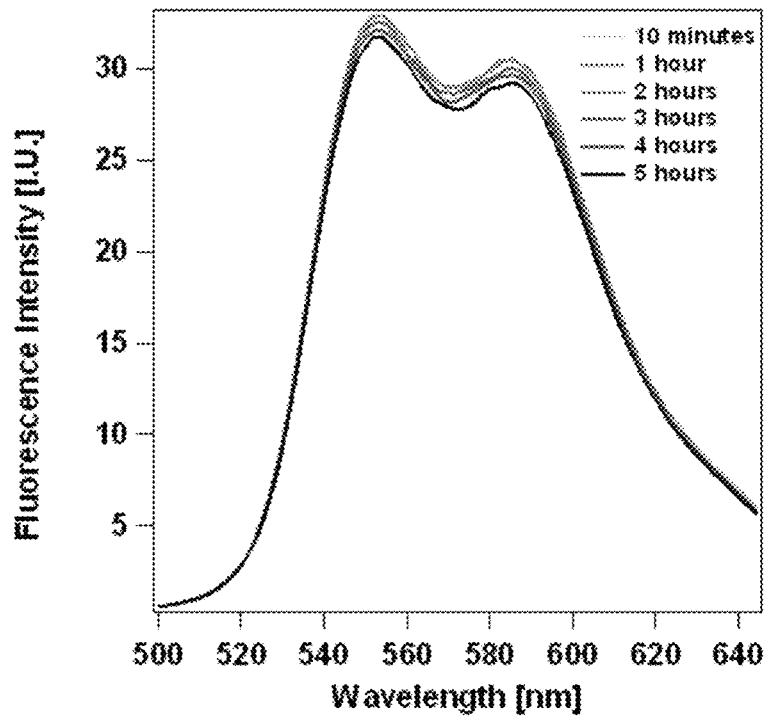
FIG. 23 shows fluorescence spectra of doxorubicin loaded dC18-1coi(PEG2K)-PEG750 micelles dissolved in 25 mM phosphate buffer, pH 7.4 containing 50 mg/ml serum albumin were recorded over time.

Fluorescence spectra of doxorubicin loaded dC18-1coi (PEG2K)-PEG750 micelles dissolved in 25 mM phosphate buffer, pH 7.4 containing 50 mg/ml serum albumin were recorded over time (FIG. 23).

Figure 24:
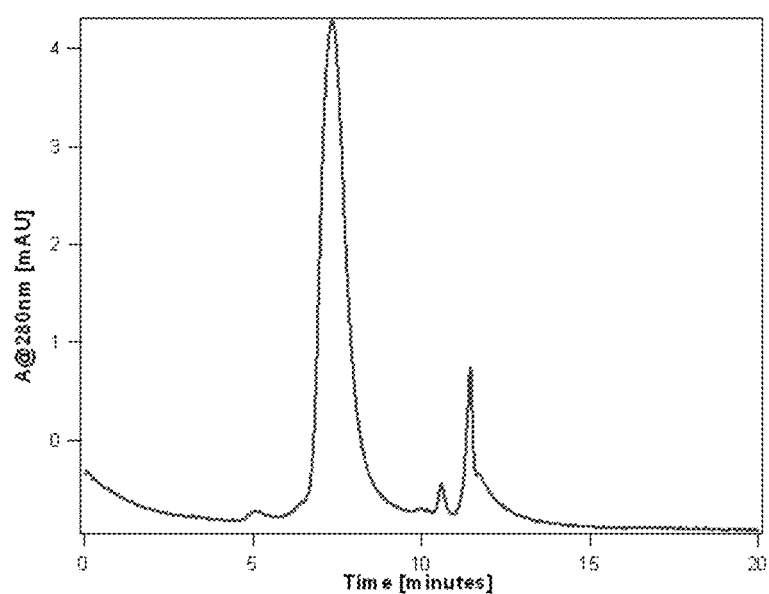
FIG. 24 shows the size exclusion chromatogram of rapamycin loaded dC18-1coi(PEG2K)-PEG750 micelles dissolved in 25 mM phosphate buffer, pH 7.4.

The size exclusion chromatogram of rapamycin loaded dC18-1coi(PEG2K)-PEG750 micelles dissolved in 25 mM phosphate buffer, pH 7.4 was recorded (FIG. 24).

Example 5: Treatment of Glioblastoma Multiforme in a Rat Model Using Drug-Loaded Micelles The drug loaded micelles of the present invention are delivered by infusion directly into brain tumors such as Glioblastoma multiforme (GBM) by convection-enhanced delivery (CED). A pressure gradient at the tip of an infusion catheter is used to initiate bulk flow that forces the infusate through the extracellular space. The pressurized infusate then engages the perivascular space and distribution is significantly aided by the pulsation of blood vessels.

The micelles are rapidly taken up by the GBM cells. The micelles can extend pharmacokinetics of the cargo drugs. The small size of the micelles micelle can improve drug efficacy as compared to other carriers. Intra-tumoral infusion restricts drug delivery to the tumor site, leading to improved safety and effectiveness, but the frequency of such delivery can be limited in practice. The long pharmacokinetics of the inventive micelles can provide for good efficacy even in situations where frequency of administration is limited.

The intrinsic safety of micellar DOX and TMZ is established by injecting 20 microliters (N=3/group) of drug-loaded micelles into normal rat striatum over a range of concentrations: 0 (saline), 0.3, 0.7, 1 and 3 mg/ml. Seven days later, rat brains are sectioned and stained with hematoxylin and eosin (H & E) staining to look for tissue pathology. The highest non-toxic dose is used in rat efficacy studies.

The pharmacokinetics of micellar doxorubicin (MC-DOX) and temzolomide (MC-TMZ) in rat GBM xenografts is studied. MC-DOX or MC-TMZ is injected at the highest non-toxic dose into implanted tumors 10 days after tumor implantation into nude rats. Tumors from rats (N=3 per time) are dissected at 1, 3, 7, 10, and 24 h, as well as 3 days and 7 days. These samples are extracted and assayed by HPLC for drug content.

The kinetic data is used to conduct an efficacy study in a nude rat U87 xenograft model of GBM. A chronic cannula guide is used to infuse drug into xenograft tumors by CED up to 10 times. Rat xenografts are infused with MC-DOX or MC-TMZ 2-3 times per week and survival is the primary end-point. The model normally has a survival time of about 20 days after tumor implantation. Micelle infusion, either control or drug-loaded, is started as early as day 10 after implantation and is repeated until animals (N=10/group) show neurological signs and/or loss of >15% body weight that indicate the need for euthanasia. Effect on survival is assessed by Meier-Kaplan analysis. Post-mortem analysis includes H & E staining. A statistically significant (p<0.05) increase in survival greater than 10 days compared to control is observed.

Example 6. Mixed Micelles

Mixed micelles (FIG. 28) were prepared by thin film hydration method. dC18-1coi(P2K)-P750 and DSPE-PEG2000 (see Formula I below) in 50/50 wt/wt % were dissolved in methanol in a glass vial. For drug loaded mixed micelles, drug (10 wt %) was added to the mixture. The solvent was evaporated in vacuum oven for 3 hours. The dried film was rehydrated with 25 mM phosphate buffer, pH 7.4, and the solution was stirred for 16 hours to allow the assembly into mixed micelles. The salts and free drug were removed by centrifugation followed by spin ultrafiltration (Amicon centrifugal filter units, MW cutoff: 3000 Da). The concentrate obtained was washed with water and lyophilized to obtain mixed micelles.

Both blank and drug loaded mixed micelles were characterized similarly to 3-helix micelles. SEC and DLS were performed to determine the size and size distribution of mixed micelles. Drug loading content was determined by HPLC. DSC was performed to study the micellar core structure. Release experiments were performed using dialysis bag method.

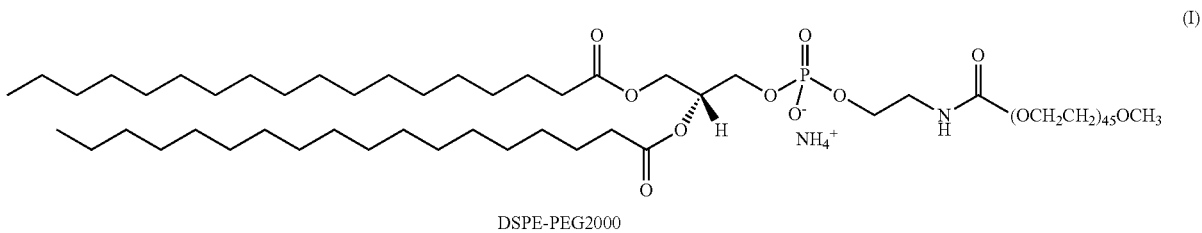

DSPE-PEG2000

Figure 29A:
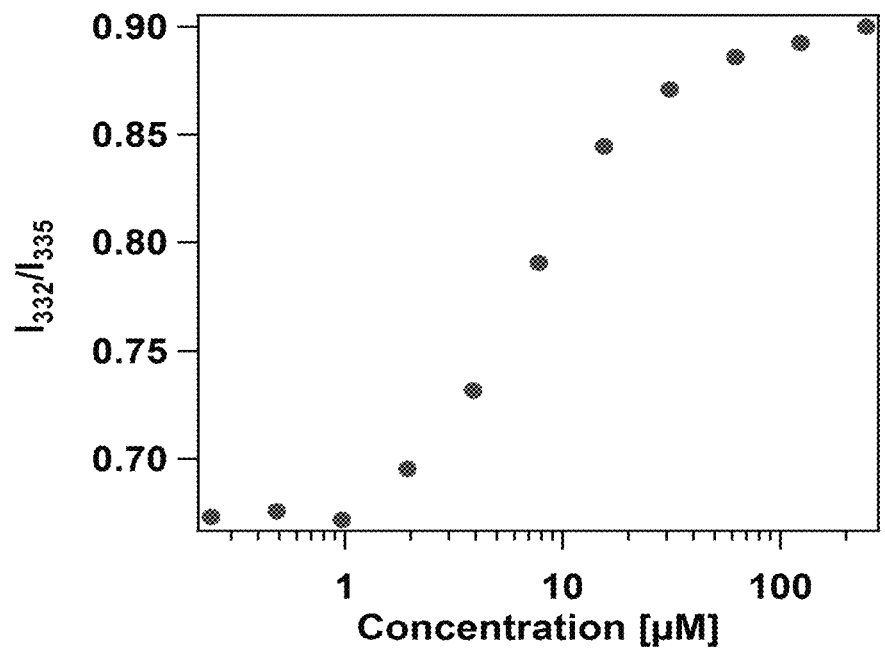
FIG. 29a shows the determination of the critical micelle concentration for dC18-1coi(PEG2K)-PEG750/DSPE-PEG mixed micelles.
Figure 29B:
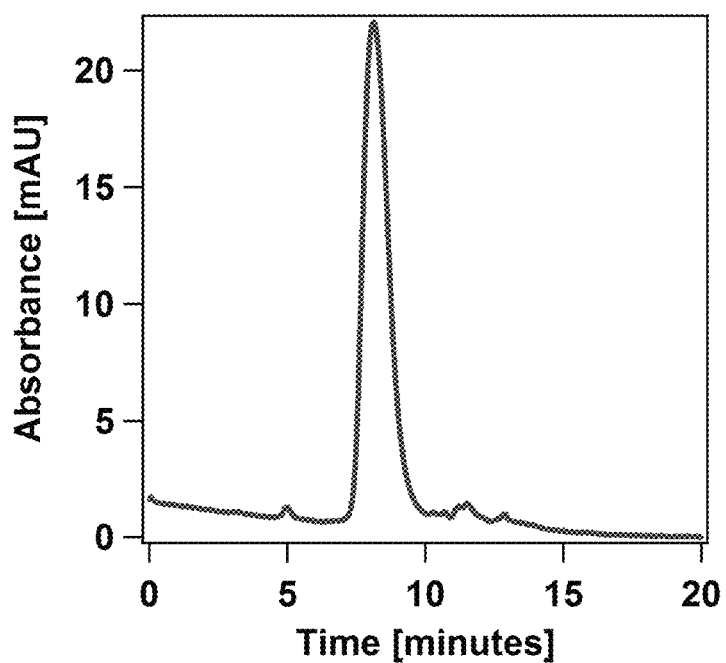
FIG. 29b shows the SEC analysis of the mixed micelles.
Figure 30A:
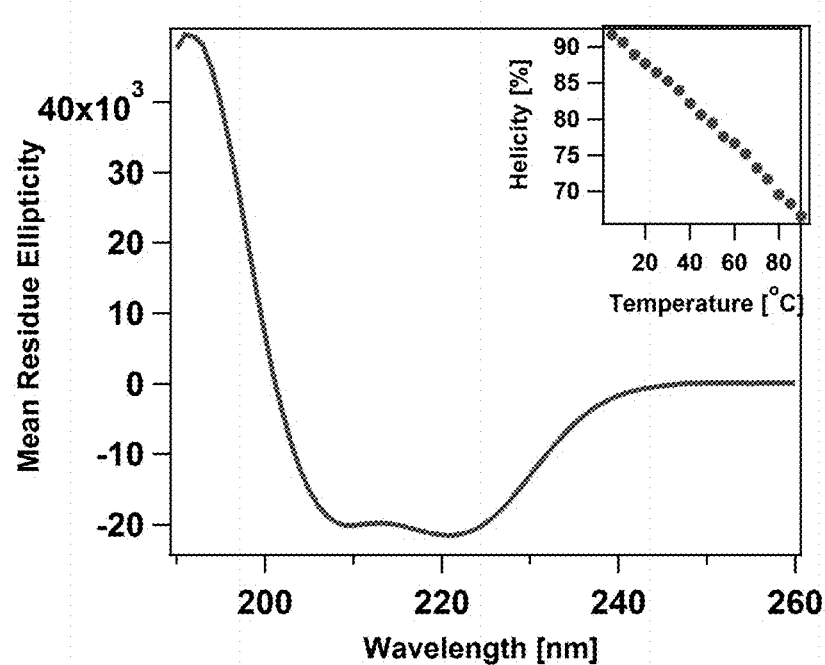
FIG. 30 shows the analysis of dC18-1coi(PEG2K)-PEG750/DSPE-PEG mixed micelles by (a) circular dichroism and (b) differential scanning calorimetry.
Figure 30B:
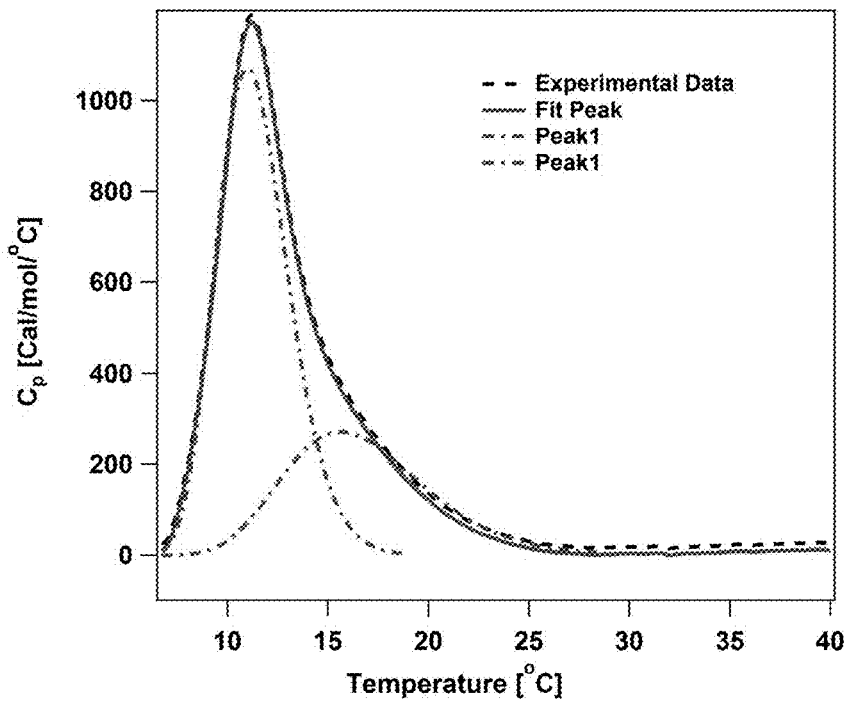

A unique critical micelle concentration (~1.5 μM) was determined using the pyrene fluorescence assay, indicating that the DSPE-PEG and dC18-1coi(P2K)-P750 assembled to form uniform mixed micelles (FIG. 29a). Elution of the micelles as a homogenous population was observed by size exclusion chromatography (FIG. 29b). The peptide helicity in the mixed micelles was ~80%, indicated that the peptide structure was maintained (FIG. 30a). The phase transition of the alkyl core for the mixed micelles was analyzed by DSC (FIG. 30b); deconvolution of the experimental data resulted in $T_t$ values of 11.5° C. and 15.4° C.

Figure 31A:
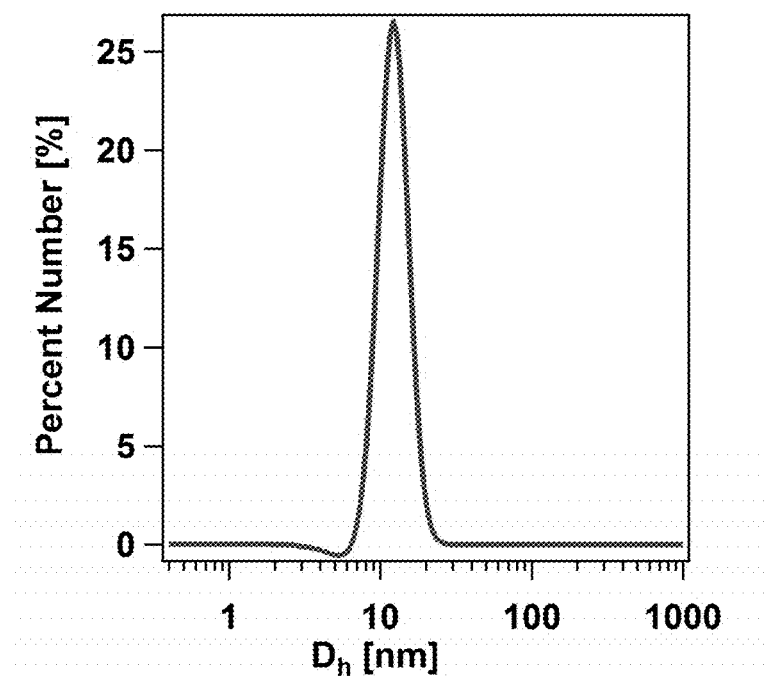
FIG. 31 shows the analysis of rapamycin-loaded dC18-1coi(PEG2K)-PEG750/DSPE-PEG mixed micelles by (a) dynamic light scattering and (b) size exclusion chromatography.
Figure 31B:
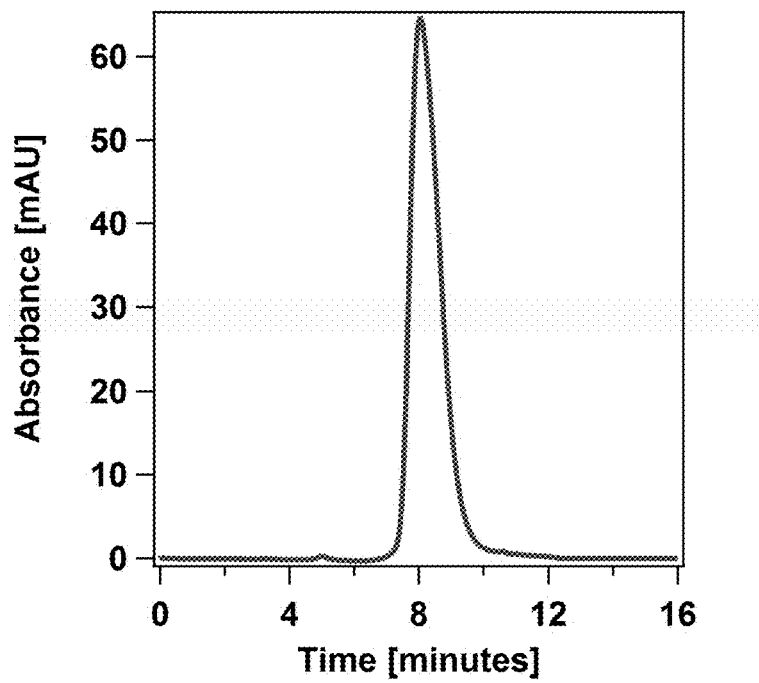

The observed rapamycin loading capacity of the mixed micelles was 7-8 wt %; this was much higher than for micelles containing only dC18-1coi(P2K)-P750 (see, Table 1). The structure and narrow size distribution of the mixed micelles was maintained during rapamycin loading, as observed by dynamic light scattering (FIG. 31a) and size exclusion chromatography (FIG. 31b).

Figure 32A:
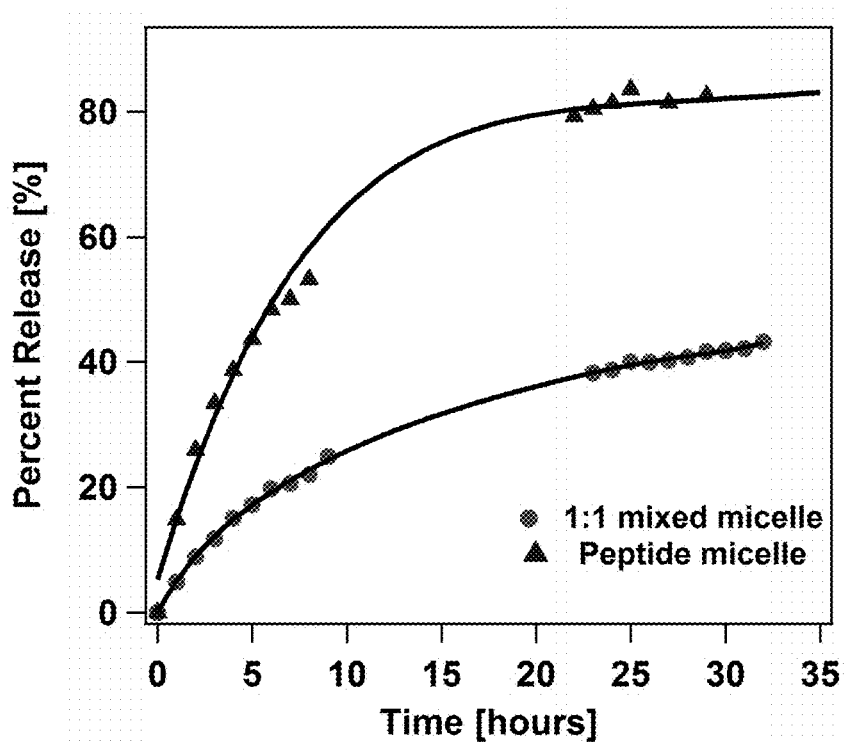
FIG. 32a shows the release of rapamycin from loaded dC18-1coi(PEG2K)-PEG750 micelles and dC18-1coi (PEG2K)-PEG750/DSPE-PEG mixed micelles.
Figure 32B:
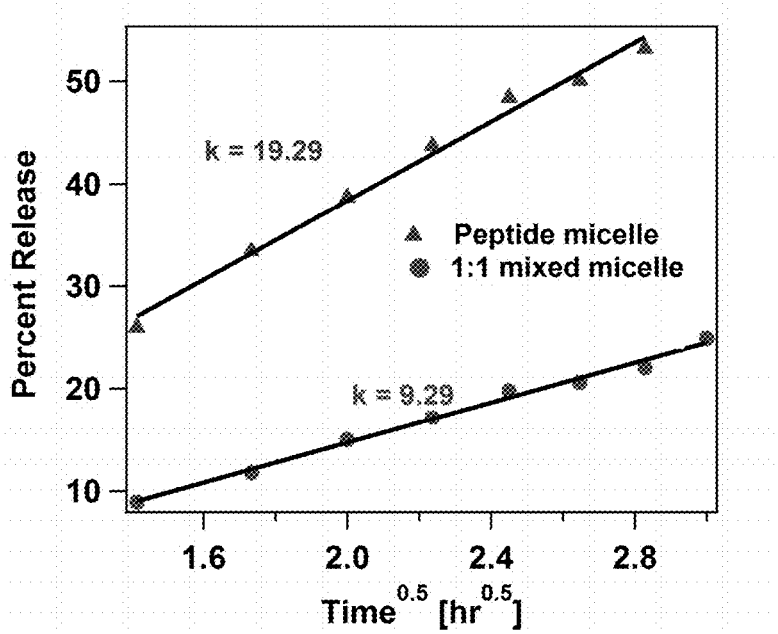
FIG. 32b shows the release data plotted according to the Higuchi model ($R=kt^{0.5}$).
Figure 33A:
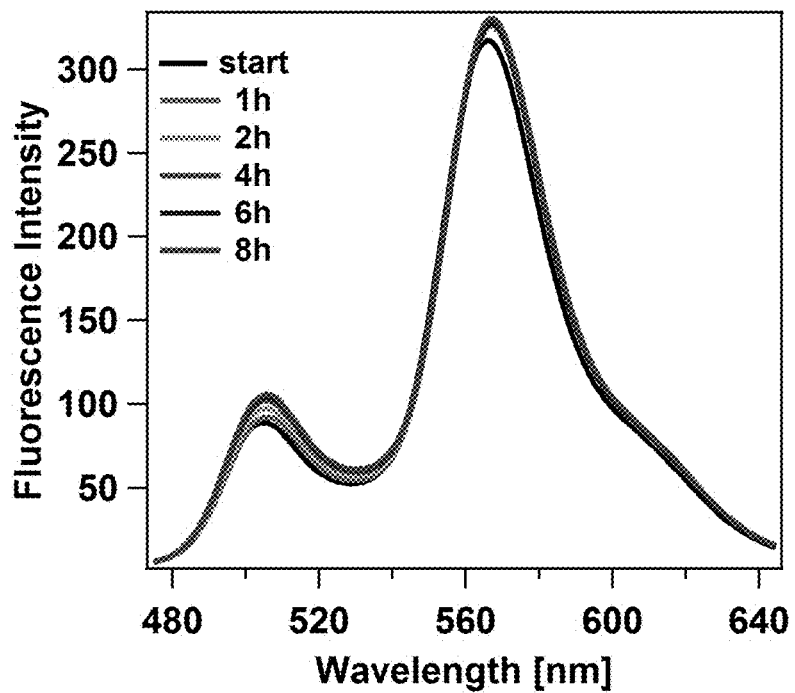
FIG. 33 shows the stability of dC18-1coi(PEG2K)-PEG750/DSPE-PEG mixed micelles as assessed by (a) fluorescence spectroscopy and (b) FRET.
Figure 33B:
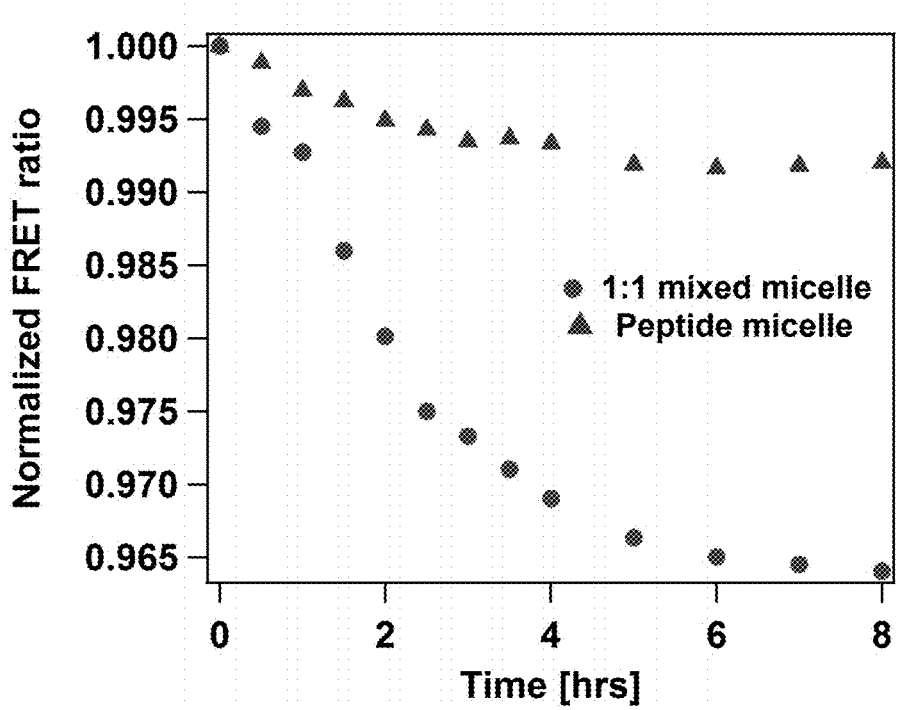
Figure 34A:
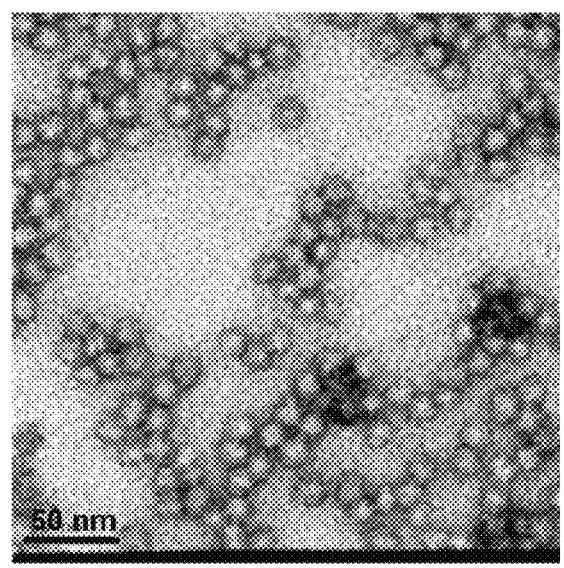
FIG. 34 shows the structural characterization of doxorubicin (DOX) (0.1 mg) from loaded dC18-1coi(P2K)-PEG750 micelles using (A) transmission electron microscopy (TEM), and (B) Differential Scanning calorimetry (DSC) thermograms.
Figure 34B:
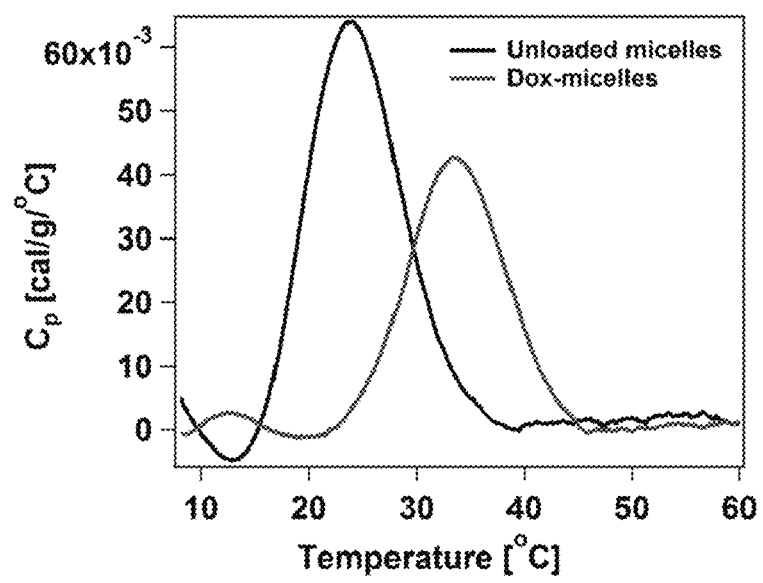

Rapamycin release from the mixed micelles was prolonged, as compared to micelles containing only dC18-1coi (P2K)-P750 (FIG. 32). Without wishing to be bound by any particular theory, it is believed that faster diffusion of rapamycin from the micelle without DSPE-PEG can account for this difference. While the mixed micelles demonstrated stability over time at 37° C. in BSA solution (FIG. 33a), the stability of the mixed micelles was slightly lower than for the micelles containing only dC18-1coi(P2K)-P750 (FIG. 33b).

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

Example 7: Stability and DOX Release in Serum Albumin

Figure 35A:
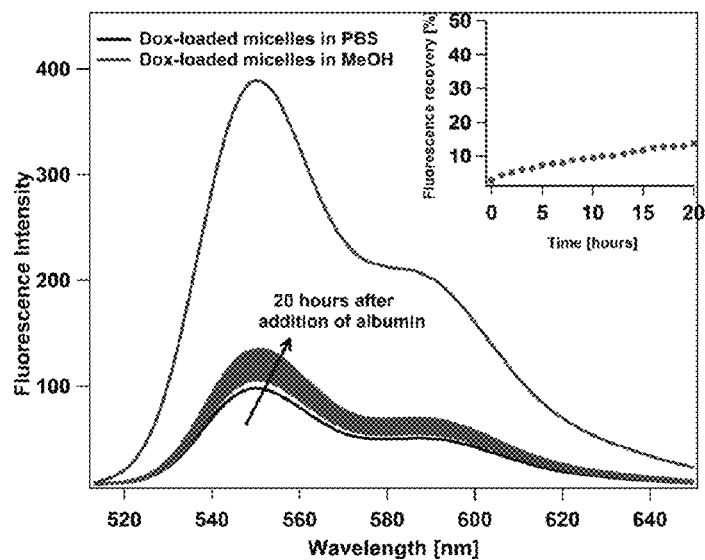
FIG. 35 shows the stability and release of DOX from loaded micelles as assessed by (A) size exclusion chromatography (SEC) chromatograms incubated in serum albumin (10 mg/ml at 37° C.) for 20 hours and (B) flourometer from DOX-loaded micelles (DOX concentration, 200 μg/ml) in presence of serum albumin (50 mg/ml, 37° C.) for 20 hours.

DOX-loaded micelles (10 mg/ml) and serum albumin (10 mg/ml) were mixed and incubated at 37° C. for 20 hours and the mixture was analyzed by SEC for any changes in size distribution (FIG. 35A). The release of DOX from 3-helix micelles was monitored by change in fluorescence of DOX-loaded micelles in presence of serum albumin (50 mg/ml). Fluorescence measurements were performed on LS-55 fluorometer (Perkin Elmer). Micelle solution in quartz cuvettes was excited at 480 nm and the emission spectra were recorded from 510-650 nm for 20 hours.

The DLS data (FIG. 35B) show that DOX-loaded and empty micelles are similar terms of size (~15 nm) and uniformity of distribution. The stability of DOX-loaded 3-helix micelles was investigated in presence of serum albumin under physiological conditions. FIG. 35A shows the SEC chromatogram of DOX-loaded micelles incubated in serum albumin for 20 hours at 37° C. The chromatograms of serum albumin and fresh DOX-loaded micelles indicate distinct elution profiles for the two components. FIG. 35A shows that the size and the uniformity of size distribution of DOX-loaded micelles are not altered in protein rich biological environment.

Figure 35B:
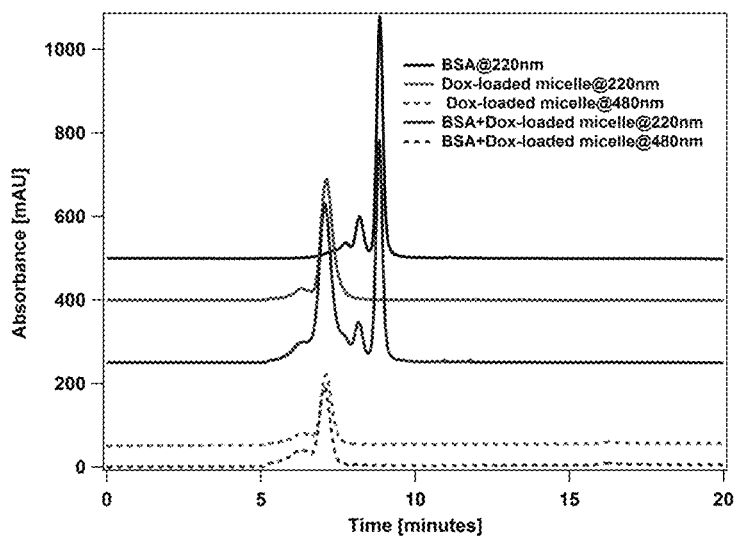

The stability of drug within the micelle was investigated in presence of albumin, by monitoring fluorescence of DOX-loaded micelles over time (FIG. 35B). FIG. 35B shows a gradual change in the fluorescence of DOX-loaded micelles in presence of serum albumin for 20 hours. The emission spectrum of an equivalent amount of DOX-loaded micelles dissolved in methanol is shown as a reference for fluorescence intensity from the free drug as methanol disrupts the structure of micelles. There is a slow rate of recovery for DOX fluorescence, only 12% after 20 hours, in presence of serum albumin (FIG. 35B inset). Quantification by dialysis bag release confirmed slow and extended release, with ~11% DOX released from 3-helix micelles after 20 hours.

Example 8: Proteolytic Disassembly of 3-Helix Micelles

Fluorescence recovery of fluorescein labeled 3-helix micelles in presence of proteinase K was monitored to study proteolytic disassembly of micelles. 10 μl of concentrated proteinase K (final concentration: 150 μg/ml) was added to fluorescently quenched solution of dye labeled micelles (15 μM peptide, 30 mol % fluorescein, 90 μl). The final molar ratio of proteinase K to peptide in solution was 1:27. The increase in fluorescence after addition of protease was monitored for 3 hours. Fluorescein was excited at 480 nm and emission spectra were recorded from 490-640 nm. The degradation of peptide in the micellar shell was analyzed by mass spectroscopy. 1 μl of sample was mixed with 1 μl of 10 mg/ml α-cyano-4-hydroxycinnamic acid matrix in acetonitrile and spotted on stainless steel MALDI plate. The spot was allowed to dry for 5 minutes and the spectrum were collected on MALDI-TOF spectrometer (Applied BioSystems).

Figure 37A:
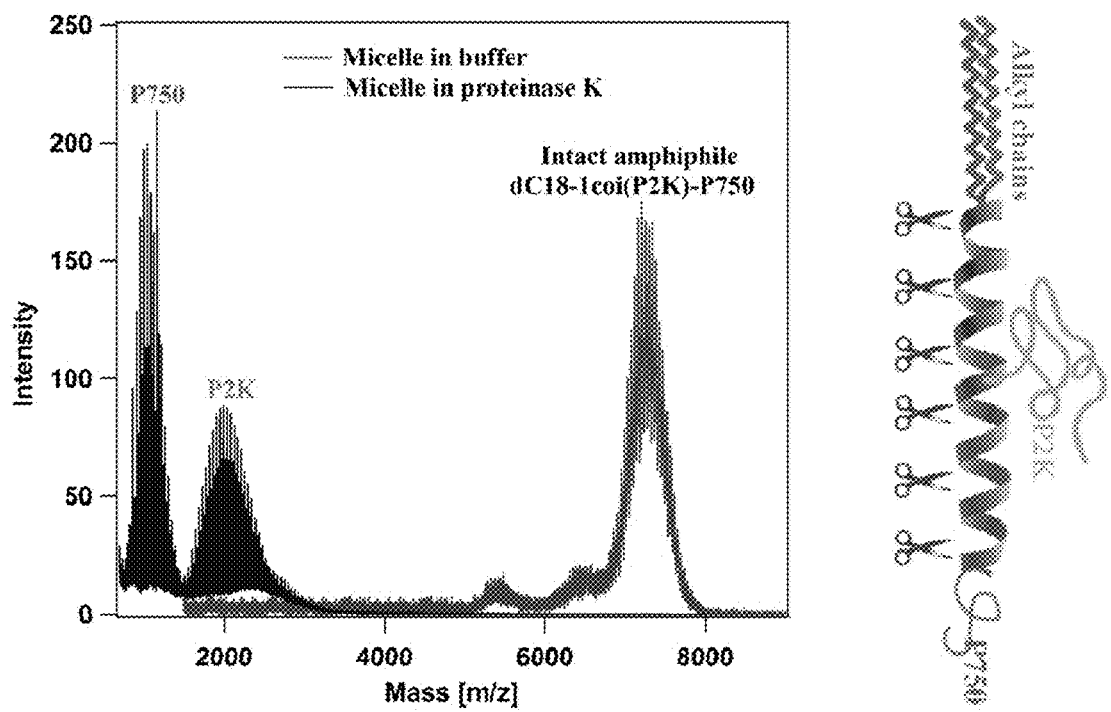
FIG. 37 shows micelle disassembly under proteolytic conditions by (A) schematic of dC18-1coi(P2K)-P750 amphiphile indicating multiple positions at which peptide could be cleaved by proteinase K, and matrix-assisted laser desorption/ionization—time-of-flight mass spectrometer (MALDI-TOF) spectra of the micelle solution before and after incubation with proteinase K; and (B) emission spectra of fluorescein labeled micelles before and after addition of proteinase K (150 μg/ml, phosphate buffer, pH 7.4).

The sequence of 1coi peptide shows multiple sites of proteolytic cleavage by proteinase K. MALDI spectrum of a micelle solution shows a peak at ~7200 Da, the mass of the amphiphilic building block, dC18-1coi(P2K)-P750 (FIG. 37A). MALDI spectrum of micelles incubated with proteinase K indicates the disappearance of amphiphile peak and the appearance of peaks associated with PEG chains attached to small peptide fragments, which suggests degradation of peptide.

Figure 37B:
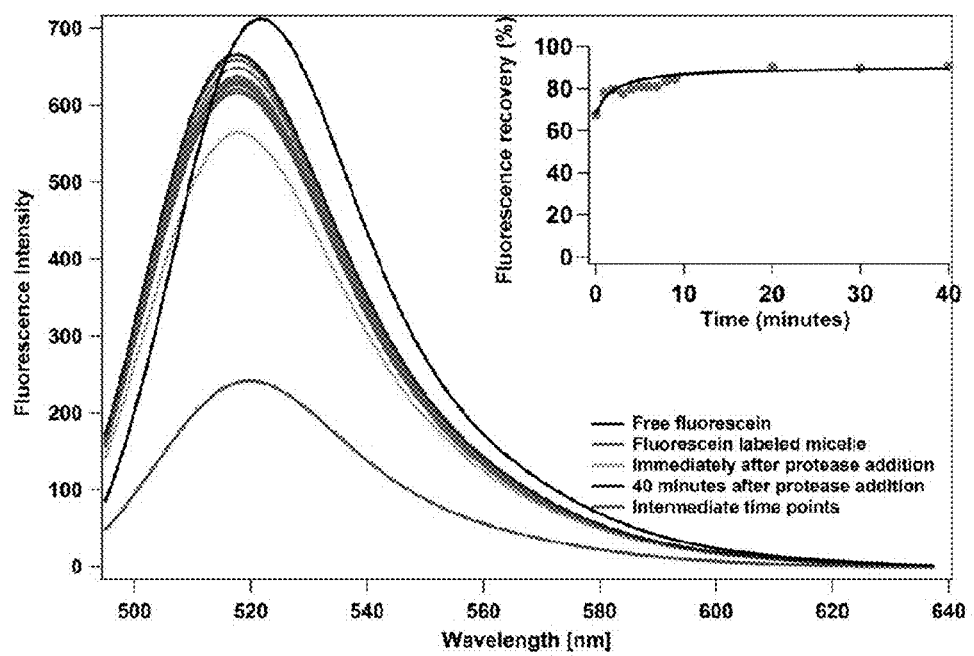

In order to confirm micelle disassembly under proteolytic conditions, fluorescence of dye labeled micelles was monitored in presence of proteinase K. For this study, 3-helix micelles were labeled with fluorescein that self quenches when placed closed to other fluorescein molecules. FIG. 37B shows that the emission intensity of fluorescein labeled micelles is significantly lower compared to free fluorescein in solution at the same concentration due to self-quenching of dye fluorescence on the micelle surface. After addition of proteinase K, fluorescence intensity starts to increase potentially due to degradation of peptide in the micellar shell, which leads to fluorescence recovery of the quenched dye. These results confirm the proteolytic degradation of peptide in micellar shell and subsequent disassembly of 3-helix micelles. 3-helix micelles undergo proteolytic disassembly after cellular internalization, resulting in DOX release that leads to cytotoxicity as demonstrated by MTT assay. The disassembly of 3-helix micelles can be triggered by proteases for drug release and clearance to minimize side effects. This unique feature opens new opportunities to design micelles where drug release can be triggered in response to tumor-specific proteases.

Example 9: In Vitro Cytotoxicity of DOX-Loaded Micelles

Figure 36A:
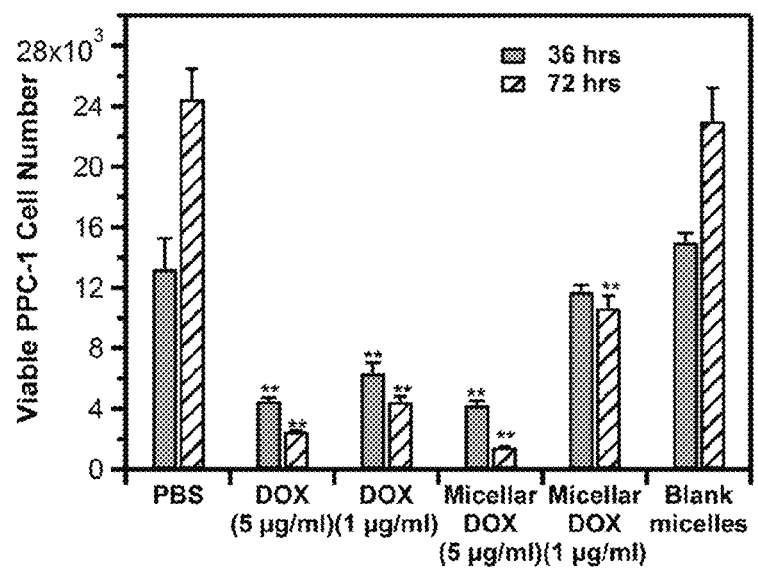
FIG. 36 shows the in vitro cytotoxicity of DOX and DOX-loaded micelles as assessed by the MTT assay in (A) PPC-1 and (B) 4T-1 cancer cells.
Figure 36B:
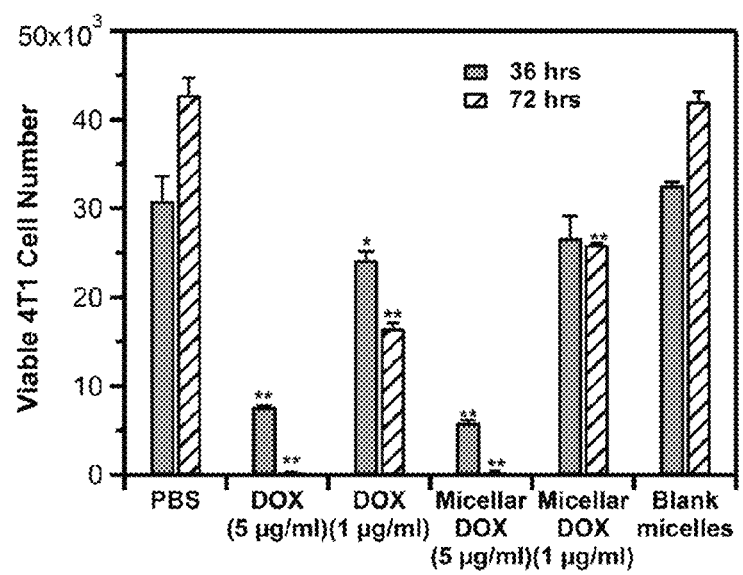

In vitro cytotoxicity of free DOX, blank micelles and DOX-loaded micelles was investigated by MTT assay (FIGS. 36A and B). PPC-1 [human cell line] (FIG. 36A) and 4T1 [syngenic mouse cell line] (FIG. 36B) cell lines were cultured in DMEM high glucose medium containing 10% FBS and IMDM medium containing 10% FBS respectively. All cultured media was supplemented with 1% Penicillin-Streptomycin (10,000 Units/mL and 10,000 μg/mL respectively). Cells were seeded at 2000 cells/well in 96-well tissue culture plates, 24 hours before the experiments. Treatments were added in 100 μl medium/well in triplicate: 1) 25% PBS (v/v) in medium, 2) free DOX (1 μg/ml and 5 μg/ml), 3) DOX-loaded micelles (1 μg/ml and 5 μg/ml encapsulated DOX) and 4) blank micelles (concentration matched to the peptide content of the DOX-loaded micelles at DOX concentration of 5 μg/ml). After 36 to 72 hours of continuous incubation of cells with each treatment at 37° C. in 5% $CO_2$, cytotoxicity was quantified via MTT assay (FIGS. 36A and B). MTT reagent (3-(4,5-dimethylthiazol-2-yl)-2, 5-diphenyltetrazolium bromide, 100 μl, 1.2 mM) was added to each well, and cells were incubated for 2 hours at 37° C. in 5% $CO_2$. After removal of medium, formazan crystals were dissolved in DMSO (100 μl/well) and absorbance was measured at wavelength 570 nm using a Tecan (San Jose, Calif.) Infinite® M1000 microplate reader. Treatments were tested in triplicate and two independent replicates of each MTT assay were performed. Statistical comparisons were performed by ANOVA followed by Tukey's multiple comparisons test. p-values of less than 0.05 were considered significant (*$p<0.05$, **$p<0.0001$).

MTT assay showed that DOX-loaded micelles exhibited concentration and time dependent in vitro cytotoxicity towards PPC-1 and 4T1 cancer cells (FIGS. 36A and B).

DOX-loaded micelles effectively suppressed the growth of these cancer cells by 36 h and the rate and extent of cytotoxicity was comparable to that of free DOX. These results confirm DOX release from 3-helix micelles in active form. The toxicity of DOX-loaded 3-helix micelles to cancer cells is comparable to free DOX after 72 hours, which is encouraging for therapeutic potential of this system.

Example 10: Convection-Enhanced Delivery (CED) of DOX-Loaded Micelles 3-helix micelles were administered to rat brain by CED to examine their distribution within the brain tissue. All procedures were in accordance with the regulations of the Institutional Animal Care and Use Committee of the University of California at San Francisco. 20 µl of free DOX and DOX-loaded micelles (DOX concentration: 0.2 mg/ml) were infused by CED at a rate of 0.5 µl/min in the striatum of normal Sprague Dawley rats as previously described. After rats were anesthetized, a sagittal incision was made in the skin, and burr-holes were made in the skull by a drill. To minimize trauma and reflux, silica cannulae (O.D. 235 µm; I.D. 100 µm) were used for all infusions (Polymicro Technologies, Phoenix, Ariz.). The cannulae were attached directly to Nanofill-100 syringes placed in the pumps controlled by a Micro4™ MicroSyringe Pump Controller (World Precision Instrument). The coordinates for the injection were taken from the rat brain atlas. A week after infusion, the rats were euthanized and brain tissue was sectioned and distribution of micelles was examined with optical microscope. The tissue sections were stained with hematoxylin and eosin (H&E) to look for pathology.

Figure 38A:
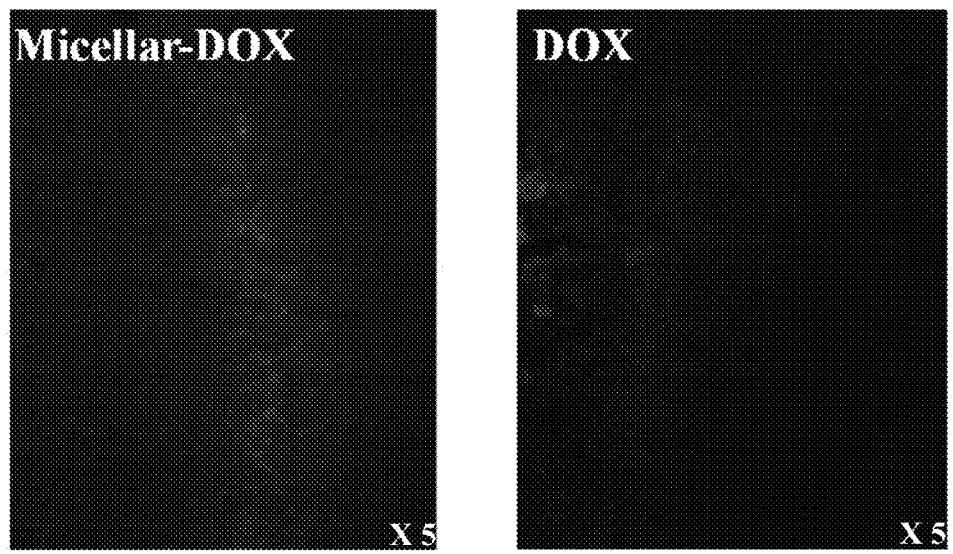
FIG. 38 shows the brain tissue distribution and toxicity of DOX-loaded micelles and free DOX delivered to Sprague Dawley rats by Convection-Enhanced Delivery (CED) as assessed by (A) fluorescence images of striatum 7 days after injection; and (B) optical microscopy of tissues after H&E staining, 7 days after injection.
Figure 38B:
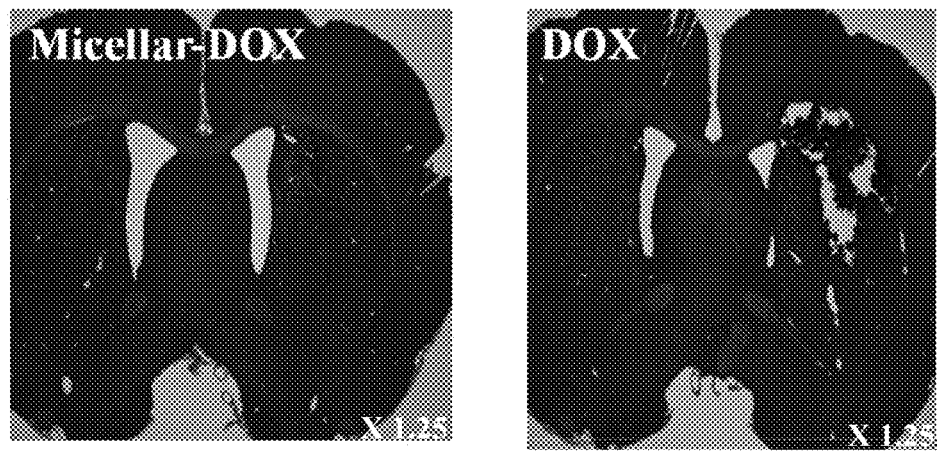

DOX-loaded micelles showed broader and more even distribution in the brain striatum compared to free DOX, 7 days after infusion (FIG. 38A). H&E staining of the harvested brain tissue, a week after infusion, showed that DOX-loaded micelles displayed reduced toxicity, whereas free DOX resulted in significant tissue damage (FIG. 38B). Distribution and toxicity profiles of DOX-loaded micelles indicate stable encapsulation of drug in 3-helix micelles with minimal release in concentrated protein environment of normal brain tissue. These results show that micelles can be locally delivered by CED, and tissue half-life of DOX can be extended with reduced toxicity towards healthy tissue after incorporation in 3-helix micelles.

Example 11: Intravenous Administration of DOX-Loaded Micelles

Figure 39A:
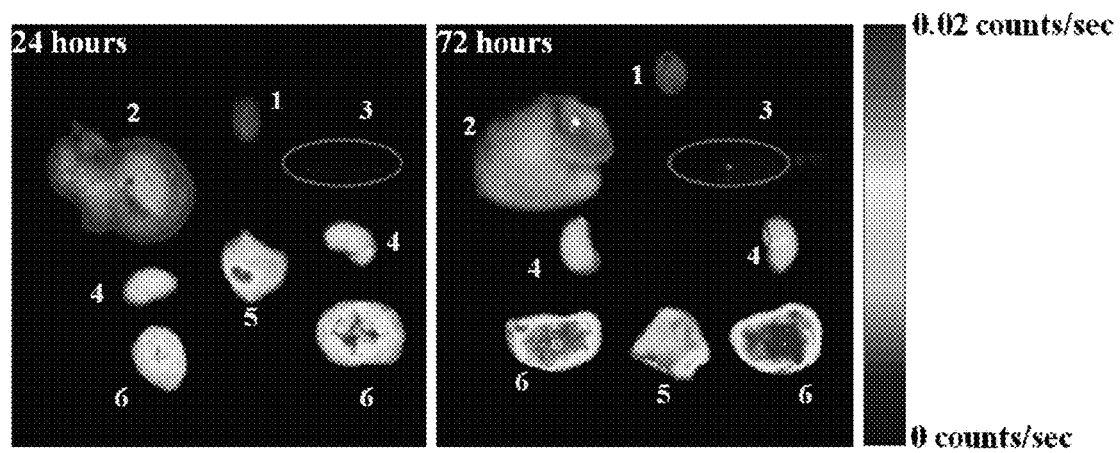
FIG. 39 shows the biodistribution and toxicity of DOX-loaded micelles after intravenous administration by (A) fluorescence images of tumor, 24 and 72 hours after injection (organs are labeled as 1: heart, 2: liver, 3: spleen, 4: kidney, 5: skin, 6: tumor); and (B) images of mouse skin, 25 days after intravenous injection of DOX-loaded micelles and DOXIL™.

The biodistribution and toxicity of DOX-loaded micelles after intravenous administration was examined. All animal experiments for intravenous administration were conducted under a protocol approved by the University of California, Davis, Institutional Animal Care and Use Committee (Davis, Calif.). NDL tumors were transplanted into the inguinal mammary fat fads of five to six week old FVB mice. Approximately after 3 weeks, when the size range of the NDL tumors was 5-10 mm, animals were anesthetized with isoflurane and received an intravenous (IV) injection of DOX-loaded micelles. Animals were injected with 150 µl of DOX-loaded micelles at a concentration of 12 mg/ml. Mice were euthanized with an IV injection of Euthasol (Western Medical Supply, CA) at 24 hours and 72 hours after administration. Blood was drawn and 50 ml of saline was perfused into the left ventricle. Organs of interest, such as heart (1), liver (2), spleen (3), kidneys (4), skin (5), and tumors (6), were harvested and scanned on a Maestro 2 imaging system (PerkinElmer, Mass.). Images were acquired at emission wavelength of 550 nm (FIG. 39A). For skin toxicity assay, DOX-loaded micelles (6 mg DOX/kg) were administered to mice intravenously two times per week. Images were taken at three weeks after treatment started.

Figure 39B:
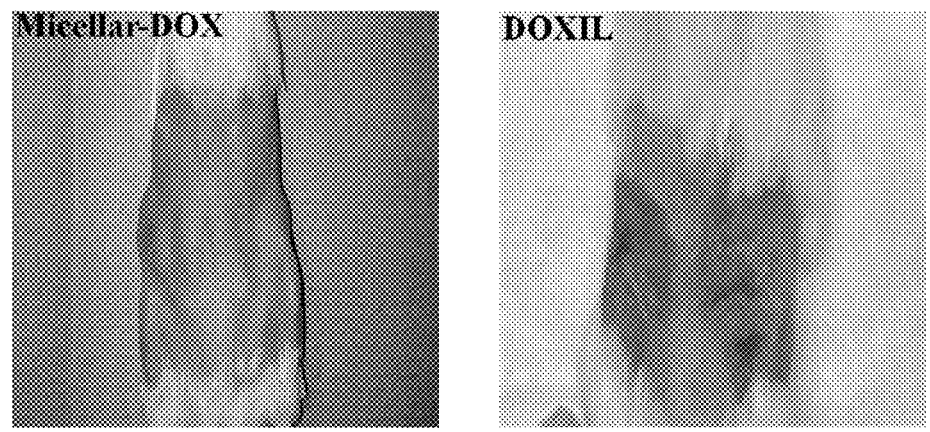

Time dependent PET imaging after tumor localization indicated that 3-helix micelles were highly mobile in tumor tissue, whereas liposomes did not show any detectable movement as function of time, which could be attributed to the significantly smaller size of 3-helix micelles compared to liposomes. FIG. 39A shows the fluorescence images from different organs, 24 and 72 h after injection of DOX-loaded micelles. Fluorescence in tumor confirms accumulation of DOX-loaded micelles due to EPR effect. Tumor fluorescence increases by 2.1 fold (p value=0.0028) from 24 to 72 h, whereas, very low fluorescence is detected for other organs during this time period. Fluorescence in different organs at these time points after free DOX injections cannot be detected as clearance time of DOX from blood circulation is on the order of tens of minutes. The selective fluorescence signal in tumor over extended time period indicates that distribution of DOX in tumor is favorably modified by encapsulation in 3-helix micelles, leading to longer tissue half-life. Thus, incorporation of DOX in 3-helix micelles increases the tumor exposure relative to free drug. Moreover, fluorescence in non-tumor sites including heart, at 24 and 72 h after injection was significantly lower. The fluorescent intensity in heart 24 hours after administration DOX-loaded 3-helix micelles was lower compared to intensity after Doxil administration as quantified previously. FIG. 39B depicts the images of mouse skin 25 days after administration of DOX-loaded micelles and Doxil. The absence of skin lesions is evident for the mouse treated with DOX-loaded micelles, which indicates that skin toxicity from DOX is significantly reduced after its formulation in 3-helix micelles.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

```
                    Sequence Listing

SEQ ID NO: 1
        EVEALEKKVAALECKVQALEKKVEALEHGW

SEQ ID NO: 2
        GGGEIWKLHEEFLCKFEELLKLHEERLKKM

SEQ ID NO: 3
        AYSSGAPPMPPF

SEQ ID NO: 4
        EGKAGEKAGAALKCGVQELEKGAEAGEGGW

SEQ ID NO: 5
        EVEALEKKVAALESKVQALEKKVEALEHGW

SEQ ID NO: 6
        EVEALEKKVAALECKVQALKKVEALEHGWG
```

What is claimed is:

1. A conjugate comprising:
   a first peptide having from 10 to 100 amino acids, wherein the peptide adopts a helical structure;
   a first polymer covalently linked to an amino acid residue of the peptide, other than the N-terminal and C-terminal amino acid residues;
   at least one second polymer covalently linked to the C-terminal amino acid residue of the peptide, wherein the first polymer and the second polymer each comprise a hydrophilic polymer, and wherein the second polymer is other than an amino acid polymer; and
   a hydrophobic moiety covalently linked to the N-terminus of the peptide, wherein the hydrophobic moiety comprises a third polymer or a lipid moiety.

2. The conjugate of claim 1, wherein the peptide is selected from the group consisting of SEQ ID NO: 1, SEQ ID NO: 2, SEQ ID NO: 4, SEQ ID NO:5 and SEQ ID NO: 6.

3. The conjugate of claim 1, wherein the first polymer and the second polymer each comprise polyethylene glycol.

4. The conjugate of claim 1, wherein the molecular weight of the first polymer is from 500 Da to 10,000 Da.

5. The conjugate of claim 4, wherein the molecular weight of the first polymer is from 1000 Da to 5000 Da.

6. The conjugate of claim 5, wherein the molecular weight of the first polymer is about 2000 Da.

7. The conjugate of claim 1, wherein the molecular weight of the second polymer is from 250 Da to 5000 Da.

8. The conjugate of claim 7, wherein the molecular weight of the second polymer is about 500 Da to 2000 Da.

9. The conjugate of claim 8, wherein the molecular weight of the second polymer is about 750 Da.

10. The conjugate of claim 1, wherein the third polymer comprises polybutadiene.

11. The conjugate of claim 1, wherein the lipid moiety comprises from 1 to 6 $C_{10-20}$ acyl groups.

12. The conjugate of claim 1, wherein the lipid moiety comprises 1, 2 or 4 $C_{10-20}$ acyl groups.

13. The conjugate of claim 1, wherein
   the first peptide comprises SEQ ID NO: 1;
   the first polymer comprises polyethylene glycol with a molecular weight of about 2000 Da;
   the second polymer is linked to the C-terminal residue of the peptide and comprises polyethylene glycol with a molecular weight of about 750 Da; and
   the hydrophobic moiety comprises the lipid moiety which comprises lysine and two $C_{18}$ acyl chains.

14. A helix bundle comprising from 2 to 6 conjugates of claim 1.

15. The helix bundle of claim 14, comprising 3 conjugates.

16. The helix bundle of claim 14, comprising 4 conjugates.

17. A particle comprising from 20 to 200 conjugates of claim 1.

18. The particle of claim 17, further comprising at least one additional agent, each independently selected from the group consisting of a therapeutic agent, a diagnostic agent, DNA, and an oligonucleotide.

19. The particle of claim 18, wherein each additional agent is independently selected from the group consisting of a fluorophore, a radionuclide, an anthracycline, a taxane, and a macrolide.

20. The particle of claim 19, wherein each additional agent is independently selected from the group consisting of doxorubicin, paclitaxel, and rapamycin.

21. The particle of claim 17, further comprising a PEGylated lipid.

22. The particle of claim 21, wherein the PEGylated lipid comprises DSPE-PEG2000.

23. A particle comprising:
   from 20 to 200 conjugates each comprising:
      a first peptide comprising SEQ ID NO:1;
      a first polymer comprising polyethylene glycol with a molecular weight of about 2000 Da;
      a second polymer covalently linked to the C-terminal residue of the peptide and comprising polyethylene glycol with a molecular weight of about 750 Da; and
      a hydrophobic moiety comprising a lipid moiety which comprises lysine and two $C_{18}$ acyl chains;
   and a therapeutic agent selected from the group consisting of doxorubicin, paclitaxel, and rapamycin.

24. The particle of claim 23, further comprising DSPE-PEG2000.

25. The particle of claim 24, wherein the ratio of the DSPE-PEG to the conjugates is about 1:1 by weight.

26. A method of forming a particle of claim 17, the method comprising maintaining a plurality of conjugates of claim 1 under conditions sufficient to allow the conjugates to self-assemble into the particles of claim 17.

27. The method of claim 26, wherein the conjugates are at a concentration of from 1 nM to 1 M.

28. The method of claim 26, further comprising adding a PEGylated lipid to the plurality of conjugates.

29. A method of treating cancer comprising administering to a human subject in need thereof, a therapeutically effective amount of a particle of claim 23 and at least one therapeutic agent.

30. The method of claim 29, wherein said cancer is selected from the group consisting of carcinomas, gliomas, mesotheliomas, melanomas, lymphomas, leukemias, adenocarcinomas, breast cancer, ovarian cancer, cervical cancer, glioblastoma, leukemia, lymphoma, prostate cancer, and Burkitt's lymphoma, brain and central nervous system, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, cervical cancer, vaginal cancer, uterine cancer, ovarian cancer, thyroid cancer, parathyroid cancer, adrenal cancer, pancreatic endocrine cancer, carcinoid cancer, bone cancer, skin cancer, retinoblastomas, Hodgkin's lymphoma, and non-Hodgkin's lymphoma.

31. The method of claim 29, wherein the at least one therapeutic agent is selected from the group consisting of doxorubicin, paclitaxel, and rapamycin.

32. The method of claim 31, wherein the at least one therapeutic agent is doxorubicin.

33. A method of treating a disease state in a human subject comprising administering a therapeutically effective amount of a particle of claim 23 and at least one therapeutic agent.

34. The method of claim 33, wherein the disease state is selected from the group consisting of cancer, autoimmune disorders, genetic disorders, infections, inflammation, neurologic disorders, and metabolic disorders.

* * * * *

SEQUENCE LISTING

<160> NUMBER OF SEQ ID NOS: 6

<210> SEQ ID NO 1
<211> LENGTH: 30
<212> TYPE: PRT
<213> ORGANISM: Artificial Sequence
<220> FEATURE:
<223> OTHER INFORMATION: synthetic de novo designed 3-helix bundle
      peptide 1coi, first peptide

<400> SEQUENCE: 1

Glu Val Glu Ala Leu Glu Lys Lys Val Ala Ala Leu Glu Cys Lys Val
1               5                   10                  15

Gln Ala Leu Glu Lys Lys Val Glu Ala Leu Glu His Gly Trp
            20                  25                  30

<210> SEQ ID NO 2
<211> LENGTH: 30
<212> TYPE: PRT
<213> ORGANISM: Artificial Sequence
<220> FEATURE:
<223> OTHER INFORMATION: synthetic 4-helix bundle heme-binding peptide

<400> SEQUENCE: 2

Gly Gly Gly Glu Ile Trp Lys Leu His Glu Glu Phe Leu Cys Lys Phe
1               5                   10                  15

Glu Glu Leu Leu Lys Leu His Glu Glu Arg Leu Lys Lys Met
            20                  25                  30

<210> SEQ ID NO 3
<211> LENGTH: 12
<212> TYPE: PRT
<213> ORGANISM: Artificial Sequence
<220> FEATURE:
<223> OTHER INFORMATION: synthetic second peptide covalently linked to
      C-terminus of first peptide

<400> SEQUENCE: 3

Ala Tyr Ser Ser Gly Ala Pro Pro Met Pro Pro Phe
1               5                   10

<210> SEQ ID NO 4
<211> LENGTH: 30
<212> TYPE: PRT
<213> ORGANISM: Artificial Sequence
<220> FEATURE:
<223> OTHER INFORMATION: synthetic control random-coil peptide

<400> SEQUENCE: 4

Glu Gly Lys Ala Gly Glu Lys Ala Gly Ala Ala Leu Lys Cys Gly Val
1               5                   10                  15

Gln Glu Leu Glu Lys Gly Ala Glu Ala Gly Glu Gly Gly Trp
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: synthetic helical peptide, first peptide

<400> SEQUENCE: 5

Glu Val Glu Ala Leu Glu Lys Lys Val Ala Ala Leu Glu Ser Lys Val
1               5                   10                  15

Gln Ala Leu Glu Lys Lys Val Glu Ala Leu Glu His Gly Trp

```
<210> SEQ ID NO 6
<211> LENGTH: 34
<212> TYPE: PRT
<213> ORGANISM: Artificial Sequence
<220> FEATURE:
<223> OTHER INFORMATION: synthetic de novo designed 3-helix bundle
      peptide 1coi, first peptide with modified C-terminus

<400> SEQUENCE: 6

Glu Val Glu Ala Leu Glu Lys Lys Val Ala Ala Leu Glu Cys Lys Val
  1               5                  10                  15

Gln Ala Leu Glu Lys Lys Val Glu Ala Leu Glu His Gly Trp Gly Gly
             20                  25                  30

Gly Lys
```